(12) United States Patent
Lelivelt et al.

(10) Patent No.: US 7,645,918 B2
(45) Date of Patent: Jan. 12, 2010

(54) **METHOD OF PLASTID TRANSFORMATION IN *ASTERACEAE*, VECTOR FOR USE THEREIN AND PLANTS THUS OBTAINED**

(75) Inventors: Cecilia Lucia Clara Lelivelt, Oud-Beijerland (NL); Jackie M. Nugent, County Kildare (IE); Matthew S. McCabe, County Kildare (IE)

(73) Assignee: Rijk Zwaan Zaadteelt En Zaadhandel B.V., De Lier (NL)

( * ) Notice: Subject to any disclaimer, the term of this patent is extended or adjusted under 35 U.S.C. 154(b) by 480 days.

(21) Appl. No.: 10/523,918

(22) PCT Filed: Aug. 8, 2003

(86) PCT No.: PCT/EP03/08948

§ 371 (c)(1),
(2), (4) Date: Oct. 18, 2005

(87) PCT Pub. No.: WO2004/016793

PCT Pub. Date: Feb. 26, 2004

(65) Prior Publication Data

US 2006/0248608 A1    Nov. 2, 2006

(30) Foreign Application Priority Data

Aug. 8, 2002    (EP) .................................. 02078273

(51) Int. Cl.
*C12N 15/82*    (2006.01)
(52) U.S. Cl. ....................................... 800/278; 800/288
(58) Field of Classification Search ........................ None
See application file for complete search history.

(56) References Cited

U.S. PATENT DOCUMENTS 5,451,513 A    9/1995  Maliga et al.
5,877,402 A *  3/1999  Maliga et al. ............... 800/298
6,376,744 B1   4/2002  Maliga et al.
6,388,168 B1 * 5/2002  Maliga et al. ............... 800/278

FOREIGN PATENT DOCUMENTS

| CN | 01145165 | | 7/2003 |
| WO | WO 99/05265 A3 | | 2/1999 |
| WO | WO99/10513 | * | 3/1999 |

OTHER PUBLICATIONS

Koop et al (1996, Planta 199:193-201).*
Hibberd Julian M. et al, Transient Expression of Green Fluorescent Protein in Various Plastid Types Following Microprojectile Bombardment;The Plant Journal(1998),16(5) 627-632.
McCabe M. et al., Developing the Lettuce Plastid as an Edible Vaccine Production System; Annual EU 5th Framework Meeting(2002), 10-13.
Van Bel Aart Je. et al., Novel Approach In Plastid Transformation; CurrentOpinion in Biotechnology(2001), 12:144-149.
Kofer Waltraud et al., Review Peg-Mediated Plastid Transformation in Higher Plants; In Vitro Cell Dev Biol.-Plant(1998), 34:303-309.
Svab Zora et al., Stable Transformation of Plastids in Higher Plants; Proc. Natl. Acad. Sci.(1990), 87:8526-8530.

* cited by examiner

*Primary Examiner*—Anne Kubelik
(74) *Attorney, Agent, or Firm*—Frommer Lawrence & Haug LLP; Thomas J. Kowalski; Russell A. Garman

(57) ABSTRACT

The present invention relates to a method for the transformation of plastid genomes of plant species, in particular *Asteraceae* plant species, comprising the steps of providing a transformation vector carrying a DNA sequence of interest; subjecting a plant material, which comprises plastids, to a transformation treatment in order to allow the plastids to receive the transformation vector; placing the thus treated plant material for a period of time into contact with a culture medium without selection agent; subsequently placing the plant material into contact with a culture medium comprising a selection agent; and refreshing the culture medium comprising a selection agent to allow plant material comprising plastids that have acquired the DNA of interest to grow into transformants.

4 Claims, 32 Drawing Sheets

Fig. 1-1

SEQ ID NO:1

```
GTTCAAGAATCAGTTTTCTTTTTATAAGGGCTAAAATCACTTATTTTGGCTTTTTTACCCCATATTGTAGGGTG
GATCTCGAAAGATATGAAAGATCTCCCTCCAAGCCGTACATACGACTTTCATCGAATACGGCTTTCCGCAGAAT
TCTATATGTATCTATGAGATCGAGTATGGAATTCTGTTTACTCACTTTAAATTGAGTATCCGTTTCCCTCCTTT
TCCTGCTAGGATTGGAAATCCTGTATTTTACATATCCATACGATTGAGTCCTTGGGTTTCCGAAATAGTGTAAA
AAGAAGTGCTTCAAATCATTGCTATTTGACTCGGACCTGTTCTAAAAAGTCGAGGTATTTCGAATTGTTTGTTG
ACACGGACAAAGTCAGGGAAAACCTCTGAAATTTTTTCAATATTGAACCTTGGACATATAATAGTTCCGAATCG
AATCTCTTTAGAAAGAAGATCTTTTGTCTCATGGTAGCCTGCTCCAGTCCCCTTACGAAACTTTCGTTATTGGG
TTAGCCATACACTTCACATGTTTCTAGCGATTCACATGGCATCATCAAATGATACAAGTCTTGGATAAGAATCT
ACAACGCACTAGAACGCCCTTGTTGACGATCCTTTACTCCGACAGCATCTAGGGTTCCTCGAACAATGTGATAT
CTCACACCGGGTAAATCCTTAACCCTCCCCCCTCTTACTAAGACTACAGAATGTTCTTGTGAATTATGGCCAAT
ACCGGGTATATAAGCAGTGATTTCAAATCCAGAGGTTAATCGTACTCTGGCAACTTTACGTAAGGCAGAGTTTG
GTTTTTTTGGGGTGATAGTGGAAAAGTTGACAGATAAGTCACCCTTACTGCCACTCTACAGAACCGTACATGAG
ATTTTCACCTCATACGGCTCCTCGTTCAATTCTTTCGAAGTTATTGGATCCTTTTCCGCGTTCGAGAATCCCCT
CCCTTCTTCCACTCCGTCCCGAAGAGTAACTAGGACCAATTTAGTCACGTTTTCATGTTCCAATTGAACACTTT
CCGTTTTTGATTATTCTCTTTACCAAACATATGCGGATCCAATCACGATCTTATAATAAGAACAAGAGATCTTT
CTCGATCAATCCCCTTGCCCCTCATTCTTCGAGAATCAGAAAGATCCTTTTCAAGTTTGAATTTGTTCATTTGG
AATCTGAGTTCTTCTACTTCATTATTTATTTAATATCAATATTTTTGCCTCTCTTTTTTTTATATTATTCCTTA
AGTCCCATAGGTTTGATCCTTTAGAATTGGACTCATTTTCTCATTGAGCGAAGGGTACGAAATAAATCAGATTG
ATTAAAAGCACTATGTGAAATATTCGGTTTTTTCCTCTTCCTCTATCCCATAGGTACAGTGTTTGAATCAATCG
AGAACCTTTTCTTCTGTCTGAATCGATATTATTCCATTCCAATTCCTTCCCGATACCTCTCAAGGAAAATCTCG
AATTGGATCCTAAATTGACGGGTTAGTGTGAGCTTATCCATGCGGTTATGCACTCTTCGAATAGGAATCCATTT
TCTGAAAGATCCTGGCTTTCGTGCTTTGGTGGGTCTCCGAGATCCTTTCGATGACCTATGTTGTGTTTGTTGAA
GGGATATCTATATAATACGATCGATTGCGTAAAGCCCGCGGTAGCAGTGGAACCGGGGAAAGTATACAGAAAAG
ACAGTTCTTTTCTATTATATATTATATTAGTCTTTTCTATTTAATTCATATTAGATTAGTCTTAGTTAGTGATC
CCGGCTTAGTGAGTCCTTTCTTCCGTGATGAACTGTTGGCGCCAGTCCTACATTTTGTCTCTGTGGACAGAGGA
GAAAAGGGGCTCCGCGGGAAGAGGATTGTACCGTGAGAGAAGCAAGGAGGTCAACCTCTTTCAAATATACAACA
TGGATTCTGGCAATGCAATGTACTTGGACTCTCATGTCGATCCGAATGAATCATCCTTTCCACGGAGGCAAATC
TTTGCCTGTTAGGTAACAGGATAGCAAGTTACAAACTCTGTCTCGGTAGGACATGGATCTCTATTACTATGAAT
TTCATAAATGAAGTAGTGAATGGTGGGGTTACCATTATCCTTTTTGTAGTGACGAATCCTGTATGTGTTCCTAA
GAAAAGGAATTTGTACATTTTTCGGGATCTCAAAGGAGCGTGGAAACACATAAGAACTCTTGAATGGAAATGGA
AAAGAGATGGAACTCCAGTTCCTTCGGAAATGGTAAGATCTTTGGCGCAAAAAAAGGGGTTGATCCGTATCATC
TTGACTTGGTTCTGCTTCCTCTATTTTTTAATAATACCGGGTCGGGTTCTTCTCCTACCCGTATCGAATAGAA
CACGCTGAGCCAAATCTTCTTCATGTAAAACCTGCTTGATTTAGATCGGGAAAATCGTGTGGTTTTATGAAACC
ATGTGCTATGGCTCGAATCCGTAGTCAATCCTATTTCCGATAGGGACAGTTGACAACTGAATCCTATTTTCCCA
TTATTTTCATATCCGTAATAGTGCGAAAAAAAAGATTAATTAAGGCGCGCCAGGCCCGGCCCCAAGTTGTTCAA
GAATAGTGTCGTTGAGTTTCTCGACCCTTTGCCTTAGGATTAATCAGTTCTATTTCTCGATGGGGCAGGGAAG
GGATATAACTCACCGGTAGAGTGTCACCCTTGACGTGGTGGAAGTCATCAGTTCGAGCCTGATTATCCCTAAAC
CCAATGTGAGTTTTGATATTTTGATTTGCTACCCCGCCGTGATTGAATGAGAATGGATAAGAGGCTCGTGGGAT
TGACGTGAGGGGGCAGGGATGGCTATATTCTGGGAGCGAACTCCGGGCGAATATGAAGCGCATGGATACAAGT
TAGGCCTTGGAATGAAAGACAATTCCGAATCCGCTTTGTCTACGAACAAGGAAGCTATAAGTAATGCAACTATG
AATCTCATGGAGAGTTCGATCCTGGCTCAGGATGAACGCTGGCGGCATGCTTAACACATGCAAGTCGGACGGGA
AGTGGTGTTTCCAGTGGCGGACGGGTGAGTAACGCGTAAGAACCTGCCCTTGGGAGGGGAACAACAGCTGGAAA
CGGCTGCTAATACCCCGTAGGCTGAGGAGCAAAAGGAGGAATCCGCCCGAGGAGGGGCTCGCGTCTGATTAGCT
AGTTGGTGAGGTAATAGCTTACCAAGGCGATGATCAGTAGCTGGTCCGAGAGGATGATCAGCCACACTGGGACT
GAGACACGGCCCAGACTCCTACGGGAGGCAGCAGTGGGGAATTTTCCGCAATGGGCGAAAGCCTGACGGAGCAA
TGCCGCGTGGAGGTAGAAGGCCCACGGGTCATGAACTTCTTTTCCCGGAGAAGAAGCAATGACGGTATCTGGGA
ATAAGCATCGGCTAACTCTGTGCCAGCAGCCGCGGTAATACAGAGGATGCAAGCGTTATCCGGAATGATTGGG
CGTAAAGCGTCTGTAGGTGGCTTTTTAAGTCCGCCGTCAAATCCCAGGGCTCAACTCTGGACAGGCGGTGGAAA
CTACCAAGCTGGAGTACGGTAGGGGCAGAGGGAATTTCCGGTGGAGCGGTGAAATGCGTAGAGATCGGAAAGAA
CACCAACGGCCAAAGCACTCTGCTGGGCCCACACTGACACTGAGAGACGAAAGCTAGGGAGCGAATGGGATTA
```

Fig. 1-2

(continued)
GATACCCCAGTAGTCCTAGCCGTAAACGATGGATACTAGGCGCTGTGCGTATCGACCCGTGCAGTGCTGTAGCT
AACGCGTTAAGTATCCCGCCTGGGGAGTACGTTCGCAAGAATGAAACTCAAAGGAATTGACGGGGGCCCGCACA
AGCGGTGGAGCATGTGGTTTAATTCGATGCAAAGCGAAGAACCTTACCAGGGCTTGACATGCCGCGAATCCTCT
TGAAAGAGAGGGGTGCCTTCGGGAACGCGGACACAGGTGGTGCATGGCTGTCGTCAGCTCGTGCCGTAAGGTGT
TGGGTTAAGTCCCGCAACGAGCGCAACCCTCGTGTTTAGTTGCCATCATTGAGTTTGGAACCCTGAACAGACTG
CCGGTGATAAGCCGGAGGAAGGTGAGGATGACGTCAAGTCATCATGCCCCTTATGCCCTGGGCGACACACGTGC
TACAATGGCCGGGACAAAGGGTCGCGATCCCGCGAGGGTGAGCTAACCCCAAAAACCCGTCCTCAGTTCGGATT
GCAGGCTGCAACTCGCCTGCATGAAGCCGGAATCGCTAGTAATCGCCGGTCAGCCATACGGCGGTGAATCCGTT
CCCGGGCCTTGTACACACCGCCCGTCACACTATGGGAGCTGGCCATGCCCGAAGTCGTTACCTTAACCGCAAGG
AGGGGGATGCCGAAGGCAGGGCTAGTGACTGGAGTGAAGTCGTAACAAGGTAGCCGTACTGGAAGGTGCGGCTG
GATCACCTCCTTTTCAGGGAGAGCTAATGCTTGTTGGGTATTTTGGTTTGACACTGCTTCACACCCAAAAAAGA
AGGGAGCTACGTCTGAGTTAAACTTGGAGATGGAAGTCTTCATTTCGTTTCTCGACAGTGAAGTAAGACCAAG

Fig. 3-1

```
LCV1 (SEQ ID NO:2):       1  gttcaagaatcagttttcttttttataagggctaaaatcacttattttggcttttttaccc   60
                             ||||||||||||||||||||||||||||||||||||||||||||||||||||||||||||
tobac (SEQ ID NO:3):  100021  gttcaagaatcagttttcttttttataagggctaaaatcacttattttggcttttttaccc  100080
ribosomal protein S12    80                                                       ^^^  K   P   K   K   V   G
(SEQ ID NO:41)

LCV1:                    61  catattgtagggtggatctcgaaagatatgaaagatctccctccaagccgtacatacgac  120
                             ||||||||||||||||||||||||||||||||||||||||||||||||||||||||||||
tobac:               100081  catattgtagggtggatctcgaaagatatgaaagatctccctccaagccgtacatacgac  100140
ribosomal protein S12    78   Y   K~~~~~~~~~~~~~~~~~~~~~~~~~~~~~~~~~~~~~~~~~~~~~~~~~~~~~~~~

LCV1:                   121  tttcatcgaatacggctttccgcagaattctatatgtatctatgagatcgagtatggaat  180
                             ||||||||||||||||||||||||||||||||||||||||||||||||||||||||||||
tobac:               100141  tttcatcgaatacggctttccgcagaattctatatgtatctatgagatcgagtatggaat  100200
ribosomal protein S12     1  ~~~~~~~~~~~~~~~~~~~~~~~~~~~~~~~~~~~~~~~~~~~~~~~~~~~~~~~~~~~~

LCV1:                   181  tctgtttactcactttaaattgagtatccgtttccctcctttcctgctaggattggaaa  240
                             ||||||||||||||||||||||||||||||||||| ||||||||||||||||||||||||
tobac:               100201  tctgtttactcactttaaattgagtatccgtttccctcccttttcctgctaggattggaaa  100260
ribosomal protein S12     1  ~~~~~~~~~~~~~~~~~~~~~~~~~~~~~~~~~~~~~~~~~~~~~~~~~~~~~~~~~~~~

LCV1:                   241  tcctgtattttacatatccatacgattgagtccttgggtttccgaaatagtgtaaaaaga  300
                             ||||||||||||||||||||||||||||||||||||||||||||||||||||||||||||
tobac:               100261  tcctgtattttacatatccatacgattgagtccttgggtttccgaaatagtgtaaaaaga  100320
ribosomal protein S12     1  ~~~~~~~~~~~~~~~~~~~~~~~~~~~~~~~~~~~~~~~~~~~~~~~~~~~~~~~~~~~~

LCV1:                   301  agtgcttcaaatcattgctatttgactcggacctgttctaaaaa-gtcgaggtatttcga  359
                             ||||||||  ||||||||||||||||||||||||||||||||||  ||||||||||||||
tobac:               100321  agtgcttcgaatcattgctatttgactcggacctgttctaaaaaagtcgaggtatttcga  100380
ribosomal protein S12     1  ~~~~~~~~~~~~~~~~~~~~~~~~~~~~~~~~~~~~~~~~~~~~~~~~~~~~~~~~~~~~

LCV1:                   360  attgtttgttgacacggacaaagtcagggaaaacctctgaaatttttcaatattgaacc  419
                             |||||||||||||||||||||||||||||||||||||||||||| |||||||||||||||
tobac:               100381  attgtttgttgacacggacaaagtcagggaaaacctctgaaattatttcaatattgaacc  100440
ribosomal protein S12     1  ~~~~~~~~~~~~~~~~~~~~~~~~~~~~~~~~~~~~~~~~~~~~~~~~~~~~~~~~~~~~

LCV1:                   420  ttggacatataatagttccgaatcgaatctctttagaaagaagatcttttgtctcatggt  479
                             |||||||||| |||||||||||||||||||||||||||||||||||||||||||||||||
tobac:               100441  ttggacatataagagttccgaatcgaatctctttagaaagaagatcttttgtctcatggt  100500
ribosomal protein S12     1  ~~~~~~~~~~~~~~~~~~~~~~~~~~~~~~~~~~~~~~~~~~~~~~~~~~~~~~~~~~~~

LCV1:                   480  agcctgctccagtcccttacgaaactttcgttattgggttagccatacacttcacatgt  539
                             ||||||||||||||||||||||||||||||||||||||||||||||||||||||||||||
tobac:               100501  agcctgctccagtcccttacgaaactttcgttattgggttagccatacacttcacatgt  100560
ribosomal protein S12     1  ~~~~~~~~~~~~~~~~~~~~~~~~~~~~~~~~~~~~~~~~~~~~~~~~~~~~~~~~~~~~

LCV1:                   540  ttctagcgattcacatggcatcatcaaatgatacaagtcttggataagaatctacaacgc  599
                             ||||||||||||||||||||||||||||||||||||||||||||||||||||||||||||
tobac:               100561  ttctagcgattcacatggcatcatcaaatgatacaagtcttggataagaatctacaacgc  100620
ribosomal protein S12     1  ~~~~~~~~~~~~~~~~~~~~~~~~~~~~~~~~~~~~~~~~~~~~~~~~~~~~~~~~~~~~

LCV1:                   600  actagaacgcccttgttgacgatcctttactccgacagcatctagggttcctcgaacaat  659
                             ||||||||||||||||||||||||||||||||||||||||||||||||||||||||||||
tobac:               100621  actagaacgcccttgttgacgatcctttactccgacagcatctagggttcctcgaacaat  100680
ribosomal protein S12    59   ~~  S   R   G   Q   Q   R   D   K   V   G   V   A   D   L   T   G   R   V   I
```

```
LCV1:             660  gtgatatctcacaccgggtaaatccttaaccctcccccctcttactaagactacagaatg 719
                       ||||||||||||||||||||||||||||||| ||||||||||||||||||||||||||||
tobac:         100681  gtgatatctcacaccgggtaaatccttaacccttcccccctcttactaagactacagaatg 100740
ribosomal protein S12 39    H  Y  R  V  G  P  L  D  K  V  R  G  G  R  V  L  V  V  S  H LCV1:             720  ttcttgtgaattatggccaataccgggtatataagcagtgatttcaaatccagaggttaa 779
                       ||||||| ||||||||||||||||||||||||||||||||||||||||||||||||||||
tobac:         100741  ttcttgtaaattatggccaataccgggtatataagcagtgatttcaaatccagaggttaa 100800
ribosomal protein S12 19    E  Q  L  N  H  G  I  G  P  I  Y  A  T  I  E  F  G  S  T  L LCV1:             780  tcgtactctggcaactttacgtaaggcagagtttggttttttgggggtgatagtggaaaa 839
                       ||||||||||||||||||||||||||||||||||||       |||||||||||||||||
tobac:         100801  tcgtactctggcaactttacgtaaggcagagtttggttttttgggggtgatagtggaaaa 100860
ribosomal protein S12 1    R  V  R  A  V  K  R  L  A  S  N  P  K  K  P  T  I  T LCV1:             840  gttgacagataagtcacccttactgccactctacagaaccgtacatgagattttcacctc 899
                       ||||||||||||||||||||||||||||||||||||||||||||||||||||||||||||
tobac:         100861  gttgacagataagtcacccttactgccactctacagaaccgtacatgagattttcacctc 100920

LCV1:             900  atacggctcctcgttcaattctttcgaagttattggatccttttccgcgttcgagaatcc 959
                       |||||||||||||||||||||||||| |||||||||||||  |||||||||||||||||
tobac:         100921  atacggctcctcgttcaattctttcgaattcattggatcc-tttccgcgttcgagaatcc 100979

LCV1:             960  cctcccttcttccactccgtcccgaagagtaactaggaccaatttagtcacgttttcatg 1019
                       || ||||||||||||||||| |||||||||||||||||||||||||||||||||||||||
tobac:         100980  cc-ccttcttccactccgccccgaagagtaactaggaccaatttagtcacgttttcatg 101038

LCV1:            1020  ttccaattgaacactttccgtttt------------------
                       |||||||||||||| ||| |||||
tobac:         101039  ttccaattgaacactgtccattttgattattctcaaaggataa 101082

LCV1:   1045  gattattctctttaccaaacatatgcggatccaatcacgatcttata----ataagaaca 1100
              |||||||||||||||||||||||||||||||||||||||||||||    |  |||||||
tobac: 101083  gattattctctttaccaaacatatgcggatccaatcacgatcttatatataagaagaaca 101142

LCV1:   1101  agagatctttctcgatcaatcccttgccctcattcttcgagaatcagaaagatccttt 1160
              | |||||||||| |||||||||||| ||||||||||||  ||||| || |||||||||
tobac: 101143  aaagatctttcttgatcaatccctttgccctcattcttcaagaataaggaagatccttt 101202

LCV1:   1161  tcaagtttgaatttgttcatttggaatctgagttcttctacttcattatttatttaatat 1220
              |||||||||||||||||||||||||||||| |||||||||||||| ||||||||||||||
tobac: 101203  tcaagtttgaatttgttcatttggaatctgggttcttctacttcat-atttatttaatat 101261

LCV1:   1221  caatattttgcctctcttttttttatattattccttaagtcccataggtttgatcctt 1280
              ||||||||  ||||||       ||||  |||||||||||||||||||||||||||||| |
tobac: 101262  gaatatttc-cctctctttttttatatcattccttaagtcccataggtttgatcctgt 101320

LCV1:   1281  agaattggactcattttctcattgagcgaagggtacgaaataaatcagattgattaaaag 1340
              ||||| ||| ||||||||||||||| ||| |||||||||||||||||||||||| |||||
tobac: 101321  agaatttgacccattttctcattgaacgaaaggtacgaaataaatcagattgat-aaaag 101379
```

```
LCV1:    1341 cactatgtgaaatattcggtttttt-----tcctcttcctctatcccataggt-----aca 1390
              || |||||||||| ||||||||||     |||||  |||||||||||||||     |||
tobac: 101380 taccatgtgaaatcttcggttttttcccccttcctcgatccctatcccataggttaggtaca 101439

LCV1:    1391 gtgtttgaatcaatcgagaaccttttcttctgtctgaatcgatattattccattccaatt 1450
              ||||||||||||||  |||||||||||||||||| || |||||||||||||||||||| |
tobac: 101440 gtgtttgaatcaatagagaaccttttcttctgtatgaatcgatattattccattccaaat 101499

LCV1:    1451 ccttcccgatacctctcaaggaaaatctcgaatt-ggatcctaaattgacgggttagtgt 1509
              |||||||||||||| ||||||||||||||||||| ||||||| |||||||||||||||||
tobac: 101500 ccttcccgatacctcccaaggaaaatctcgaatttggatcccaaattgacgggttagtgt 101559

LCV1:    1510 gagcttatccatgcggttatgcactcttcgaataggaatccatttttctgaaagatcctgg 1569
              |||||||||||||||||||||||||| |||||||||||||||||||||| |||||||||||||
tobac: 101560 gagcttatccatgcggttatgcactctttgaataggaatccgttttctgaaagatcctgg 101619

LCV1:    1570 ctttcgtgctttggtgggtctccgagatcctttcgatgacctatgttgtgtttgttgaag 1629
              |||||| ||||||||||||||||||||||||||||||||||||||||         ||||||
tobac: 101620 ctttcgtactttggtgggtctccgagatcctttcgatgacctatg---------ttgaag 101670

LCV1:    1630 ggatatctatataatacgatcgattgcgtaaagcccgcggtagcagtggaaccggggaaa 1689
              |||||||||| ||||  ||||||||||||||||||||||||||||| ||||||||||||||
tobac: 101671 ggatatctatctaatccgatcgattgcgtaaagcccgcggtagcaacggaaccggggaaa 101730

LCV1:    1690 gtatacagaaaagacagttctttctattatat 1722
              ||||||||||||||||||||||||||||||||
tobac: 101731 gtatacagaaaagacagttctttctattatat 101763

LCV1:    1723 attatattagtcttttctatttaattc                       1749
                                             |||||||||
tobac: 101764 tagta         ttttctattatattaagatatattagactatt    101799

LCV1:         1750 atattagattagtcttagttagtgatcccggcttagtgagtcctttcttccgtgatgaac 1809
                   |||||||||||| ||||||||||||||||||  ||||||||||              |||||||
tobac:      101800 atattagattagtattagttagtgatcccgacttagtgagtc----------tgatgaat 101849

LCV1:         1810 tgttggcgccagtcctacattttgtctctgtggacagaggagaaaaggggctccgcggga 1869
                   ||||||| ||||||||||||||||||||||||||||| |||||||||||||||| ||||||
tobac:      101850 tgttggcaccagtcctacattttgtctctgtggaccgaggagaaaaggggctcggcggga 101909

LCV1:         1870 agaggattgtaccgtgagagaagcaaggaggtcaacctctttcaaatatacaacatggat 1929
                   |||||| ||||||  |||||||||||||||||||||||||||||||||||||||||||||
tobac:      101910 agaggagtgtaccatgagagaagcaaggaggtcaacctctttcaaatatacaacatggat 101969
hypothetical protein 127                                  ^^^ I  Y  L  M  S
(SEQ ID NO:4)

LCV1:         1930 tctggcaatgcaatgtacttggactctcatgtcgatccgaatgaatcatcctttccacgg 1989
                   ||||||||||     || |||||||||||||||||||||||||||||||||||||||||
tobac:      101970 tctggcaatg-----tagttggactctcatgtcgatccgaatgaatcatcctttccacgg 102024
hypothetical protein 123  E  P  L  T        T  P  S  E  H  R  D  S  H  I  M  R  E  V  S
```

```
LCV1:                  1990   aggcaaatctttgcctgttaggtaacaggatagcaagttacaaactctgtctcggtagga 2049
                              ||| ||||||||||||| |||| || ||||||||||||| |||| |||||||||||||||
tobac:               102025   aggtaaatctttgcctgctaggcaagaggatagcaagttccaaattctgtctcggtagga 102084
hypothetical protein 88         T  F  R  Q  R  S  P  L  L  I  A  L  E  L  N  Q  R  P  L  V LCV1:                  2050   catggatctctattactatgaatttcataaatgaagtagtgaatggtggggttaccatta 2109
                              |||| || |||||||||||||||| ||||||||||||||| ||||| |||||||||||||
tobac:               102085   catgtatttctattactatgaaattcataaatgaagtagttaatggtagggttaccatta 102144
hypothetical protein 1                        M  K  F  I  N  E  V  V  N  G  R  V  T  I
(SEQ ID NO:5)
hypothetical protein 68        H  I  E  I  V  I  F  N  M  F  S  T  T  L  P  L  T  V  M  I LCV1:                  2110   tccttttgtagtgacgaatcctgtatgtgttcctaagaaaaggaatttgtacattttc 2169
                              ||||||||||||||||||||||| |||||||||||||||||||||||||||| |||||||
tobac:               102145   tccttttgtagtgacgaatcttgtatgtgttcctaagaaaaggaatttgtccattttc 102204
hypothetical protein 15    I  L  F  V  V  T  N  L  V  C  V  P  K  K  R  N  L  S  I  F
hypothetical protein 48      R  K  T  T  V  F  R  T  H  T  G  L  F  L  F  K  D  M  K  R LCV1:                  2170   gggatctcaaaggagcgtggaaacacataagaactcttgaatggaaatggaaaagagatg 2229
                              ||| ||||||||| |||||||||||| |||||||||||      ||||||||||||||||
tobac:               102205   ggggtctcaaaggggcgtggaaacgcataagaactcttg------aatggaaaagagatg 102258
hypothetical protein 35    R  G  L  K  G  A  W  K  R  I  R  T  L        E  W  K  R  D
hypothetical protein 35      P  R  L  P  A  H  F  R  M  L  V  R  S        H  F  L  S  T LCV1:                  2230   gaactccagttccttcggaaatggtaagatctttggcgcaaaaaaggggttgatccgta 2289
                              |||||||||||||||||
tobac:               102259   taactccagttccttcg-------------------------------------------- 102275
hypothetical protein 24    V  G  T  G  E
hypothetical protein 53    V  T  P  V  P  S LCV1                   2290   tcatcttgacttggttctgcttcctctatttttttaataataccgggtcgggttcttctc 2349
Tobac:                        -----------------------------------------------------------

LCV1                   2350   ctacccgtatcgaatagaacacgctgagccaaatcttcttcatgtaaaacctgcttgatt 2409
Tobac:                        -----------------------------------------------------------

LCV1                   2410   tagatcgggaaaatcgtgtggttttatgaaaccatgtgctatggctc 2456
Tobac:                        -----------------------------------------------

LCV1:                  2457   gaatccgtagtcaatcctatttccgatagggacagttgacaactgaatcctatttt-ccc 2515
                              ||||| |||||||||||||||||||||||||| ||||||| |||| ||||||| |||  ||
tobac:               102276   gaatcggtagtcaatcctatttccgatagggcagttgacaattgaatccgattttgacc 102335
hypothetical protein 6       S  D  T  T  L  G  I  E  S  L  P  L  Q  C  N  F  G  I  K  V
hypothetical protein 59      E  S  V  V  N  P  I  S  D  R  G  S  ^^^
                                                                            PacI/AscI
LCV1:                  2516   attatttcatatccgtaatagtgcgaaaaaaaagattaattaaggcgcgcc 2567
                              |||||||||||||||||||||||||||||||| |
tobac:               102336   attatttcatatccgtaatagtgcgaaaaga-------------------- 102367
hypothetical protein 1        M  I  K  M
```

Fig. 3-5

```
(continued)
LCV1:    2568  aggcccggccccaagttgttcaagaatagtgtcgttgagtttctcgaccctttgccttag  2627
                |||||||||| |||||||||||||||||||| |||||||||||||||||||||| |||||
tobac: 102368  aggcccggctccaagttgttcaagaatagtggcgttgagtttctcgaccctttgacttag 102427

LCV1:    2628  gattaatcagttctatttctcgatgggggcagggaagggatataactcaccggtagagtg 2687
                |||||  |||||||||||||||||||||| ||||||||||||||||||| ||||||||||
tobac: 102428  gattagtcagttctatttctcgatgggg-cggggaagggatataactcagcggtagagtg 102486

LCV1:    2688  tcacccttgacgtggtggaagtcatcagttcgagcctgattatccctaaacccaatgtga 2747
                |||||  ||||||||||||||||||||||||||||||||||||||||||  |||||||||
tobac: 102487  tcacc-ttgacgtggtggaagtcatcagttcgagcctgattatccctaagcccaatgtga 102545

LCV1:    2748  gttttgatattttgatttgctaccccgccgtgattgaatgagaatggataagaggctcgt 2807
                |||||  || || |||||||||  |||||||| ||  ||||||||||||||||||||||
tobac: 102546  gtttttctagttggatttgctcccccgccgtcgttcaatgagaatggataagaggctcgt 102605

LCV1:    2808  gggattgacgtgaggggggcagggatggctatatttctgggagcgaactccgggcgaatat 2867
                ||||||||||||||||||||||||||||||||||||||||||||||||||||||||||||
tobac: 102606  gggattgacgtgaggggggcagggatggctatatttctgggagcgaactccgggcgaatat 102665

LCV1:    2868  gaagcgcatggatacaagttaggccttggaatgaaagacaattccgaatccgctttgtct 2927
                ||||||||||||||||||||||  ||||||||||||||||||||||||||||||||||||
tobac: 102666  gaagcgcatggatacaagttatgccttggaatgaaagacaattccgaatccgctttgtct 102725

LCV1:    2928  acgaacaaggaagctataagtaatgcaactatgaatctcatggagagttcgatcctggct 2987
                ||||||||||||||||||||||||||||||||||||||||||||||||||||||||||||
tobac: 102726  acgaacaaggaagctataagtaatgcaactatgaatctcatggagagttcgatcctggct 102785

LCV1:    2988  caggatgaacgctggcggcatgcttaacacatgcaagtcggacgggaagtggtgtttcca 3047
                ||||||||||||||||||||||||||||||||||||||||||||||||||||||||||||
tobac: 102786  caggatgaacgctggcggcatgcttaacacatgcaagtcggacgggaagtggtgtttcca 102845

LCV1:    3048  gtggcggacgggtgagtaacgcgtaagaacctgcccttgggagggaacaacagctggaa  3107
                ||||||||||||||||||||||||||||||||||||||||||||||||||||||||||||
tobac: 102846  gtggcggacgggtgagtaacgcgtaagaacctgcccttgggagggaacaacagctggaa  102905

LCV1:    3108  acggctgctaataccccgtaggctgaggagcaaaaggaggaatccgcccgaggagggggct 3167
                ||||||||||||||||||||||||||||||||||||||||||||||||||||||||||||
tobac: 102906  acggctgctaataccccgtaggctgaggagcaaaaggaggaatccgcccgaggagggggct 102965

LCV1:    3168  cgcgtctgattagctagttggtgaggtaatagcttaccaaggcgatgatcagtagctggt 3227
                ||||||||||||||||||||||||| ||||||||||||||||||||||||||||||||||
tobac: 102966  cgcgtctgattagctagttggtgaggcaatagcttaccaaggcgatgatcagtagctggt 103025

LCV1:    3228  ccgagaggatgatcagccacactgggactgagacacggcccagactcctacgggaggcag 3287
                ||||||||||||||||||||||||||||||||||||||||||||||||||||||||||||
tobac: 103026  ccgagaggatgatcagccacactgggactgagacacggcccagactcctacgggaggcag 103085

LCV1:    3288  cagtggggaattttccgcaatgggcgaaagcctgacggagcaatgccgcgtggaggtaga 3347
                ||||||||||||||||||||||||||||||||| ||||||||||||||||||||||||||
tobac: 103086  cagtggggaattttccgcaatgggcgaaagc-tgacggagcaatgccgcgtggaggtaga 103144
```

Fig. 3-6

```
(continued)
LCV1:    3348 aggcccacgggtcatgaacttcttttcccggagaagaagcaatgacggtatctggggaat 3407
              ||||||||||||| ||||||||||||||||||||||||||||||||||||||||||||||
tobac: 103145 aggcccacgggtcgtgaacttcttttcccggagaagaagcaatgacggtatctggggaat 103204

LCV1:    3408 aagcatcggctaactctgtgccagcagccgcggtaatacagaggatgcaagcgttatccg 3467
              ||||||||||||||||||||||||||||||||||||||||||||||||||||||||||||
tobac: 103205 aagcatcggctaactctgtgccagcagccgcggtaatacagaggatgcaagcgttatccg 103264

LCV1:    3468 gaatgattgggcgtaaagcgtctgtaggtggcttttttaagtccgccgtcaaatcccaggg 3527
              ||||||||||||||||||||||||||||||||||||||||||||||||||||||||||||
tobac: 103265 gaatgattgggcgtaaagcgtctgtaggtggcttttttaagtccgccgtcaaatcccaggg 103324

LCV1:    3528 ctcaactctggacaggcggtggaaactaccaagctggagtacggtaggggcagagggaat 3587
              ||||||  ||||||||||||||||||||||||||||||||||||||||||||||||||||
tobac: 103325 ctcaaccctggacaggcggtggaaactaccaagctggagtacggtaggggcagagggaat 103384

LCV1:    3588 ttccggtggagcggtgaaatgcgtagagatcggaaagaacaccaacggccaaagcactct 3647
              ||||||||||||||||||||||||||||||||||||||||||||||||   |||||||||
tobac: 103385 ttccggtggagcggtgaaatgcgtagagatcggaaagaacaccaacggcgaaagcactct 103444

LCV1:    3648 gctgggcccacactgacactgagagacgaaagctaggggagcgaatgggattagataccc 3707
              ||||||| ||||||||||||||||||||||||||||||||||||||||||||||||||||
tobac: 103445 gctgggccgacactgacactgagagacgaaagctaggggagcgaatgggattagataccc 103504

LCV1:    3708 cagtagtcctagccgtaaacgatggatactaggcgctgtgcgtatcgacccgtgcagtgc 3767
              ||||||||||||||||||||||||||||||||||||||||||||||||||||||||||||
tobac: 103505 cagtagtcctagccgtaaacgatggatactaggcgctgtgcgtatcgacccgtgcagtgc 103564

LCV1:    3768 tgtagctaacgcgttaagtatcccgcctggggagtacgttcgcaagaatgaaactcaaag 3827
              ||||||||||||||||||||||||||||||||||||||||||||||||||||||||||||
tobac: 103565 tgtagctaacgcgttaagtatcccgcctggggagtacgttcgcaagaatgaaactcaaag 103624

LCV1:    3828 gaattgacggggggcccgcacaagcggtggagcatgtggtttaattcgatgcaaagcgaag 3887
              ||||||||||||||||||||||||||||||||||||||||||||||||||||||||||||
tobac: 103625 gaattgacggggggcccgcacaagcggtggagcatgtggtttaattcgatgcaaagcgaag 103684

LCV1:    3888 aaccttaccagggcttgacatgccgcgaatcctcttgaaagagagggggtgccttcgggaa 3947
              ||||||||||||||||||||||||||||||||||||||||||||||||||||||||||||
tobac: 103685 aaccttaccagggcttgacatgccgcgaatcctcttgaaagagagggggtgccttcgggaa 103744

LCV1:    3948 cgcggacacaggtggtgcatggctgtcgtcagctcgtgccgtaaggtgttgggttaagtc 4007
              ||||||||||||||||||||||||||||||||||||||||||||||||||||||||||||
tobac: 103745 cgcggacacaggtggtgcatggctgtcgtcagctcgtgccgtaaggtgttgggttaagtc 103804

LCV1:    4008 ccgcaacgagcgcaaccctcgtgtttagttgccatcattgagtttggaaccctgaacaga 4067
              |||||||||||||||||||||||||||||||||||| |||||||||||||||||||||||
tobac: 103805 ccgcaacgagcgcaaccctcgtgtttagttgccatcgttgagtttggaaccctgaacaga 103864

LCV1:    4068 ctgccggtgataagccggaggaaggtgaggatgacgtcaagtcatcatgccccttatgcc 4127
              ||||||||||||||||||||||||||||||||||||||||||||||||||||||||||||
tobac: 103865 ctgccggtgataagccggaggaaggtgaggatgacgtcaagtcatcatgccccttatgcc 103924
```

Fig. 3-7

```
(continued)
LCV1:      4128 ctgggcgacacacgtgctacaatggccgggacaaagggtcgcgatcccgcgagggtgagc 4187
                ||||||||||||||||||||||||||||||||||||||||||||||||||||||||||||
tobac:   103925 ctgggcgacacacgtgctacaatggccgggacaaagggtcgcgatcccgcgagggtgagc 103984

LCV1:      4188 taacccccaaaaacccgtcctcagttcggattgcaggctgcaactcgcctgcatgaagccg 4247
                ||||||||||||||||||||||||||||||||||||||||||||||||||||||||||||
tobac:   103985 taacccccaaaaacccgtcctcagttcggattgcaggctgcaactcgcctgcatgaagccg 104044

LCV1:      4248 gaatcgctagtaatcgccggtcagccatacggcggtgaatccgttcccgggccttgtaca 4307
                |||||||||||||||||||||||||||||||||||||||||| |||||||||||||||||
tobac:   104045 gaatcgctagtaatcgccggtcagccatacggcggtgaattcgttcccgggccttgtaca 104104

LCV1:      4308 caccgcccgtcacactatgggagctggccatgcccgaagtcgttaccttaaccgcaagga 4367
                ||||||||||||||||||||||||||||||||||||||||||||||||||||||||||||
tobac:   104105 caccgcccgtcacactatgggagctggccatgcccgaagtcgttaccttaaccgcaagga 104164

LCV1:      4368 gggggatgccgaaggcagggctagtgactggagtgaagtcgtaacaaggtagccgtactg 4427
                ||||||||||||||||||||||||||||||||||||||||||||||||||||||||||||
tobac:   104165 gggggatgccgaaggcagggctagtgactggagtgaagtcgtaacaaggtagccgtactg 104224

LCV1:      4428 gaaggtgcggctggatcacctccttttcagggagagctaatgcttgttgggtattttggt 4487
                ||||||||||||||||||||||||||||||||||||||||||||||||||||||||||||
tobac:   104225 gaaggtgcggctggatcacctccttttcagggagagctaatgcttgttgggtattttggt 104284

LCV1:      4488 ttgacactgcttcacaccc----aaaaaagaagggagctacgtctgagttaaacttggag 4543
                |||||||||||||||||||    ||||||||||||||||||||||||||||||||||||
tobac:   104285 ttgacactgcttcacaccccccaaaaaaaagaagggagctacgtctgagttaaacttggag 104344

LCV1:      4544 atggaagtcttcatttcgtttctcgacagtgaagtaagaccaag 4587
                ||||||||||| |||| ||||||||| ||||||||||||||||
tobac:   104345 atggaagtcttc-tttcctttctcgacggtgaagtaagaccaag 104387
```

LCV1A-5'ATGAGCTCGTTCAAGAATCAGTTTTCTT3' (100021-100040 in TCG) (SEQ ID NO:6)
LCV1B-5'GGCGCGCCTTAATTAATCTTTTTTTTCGCACTATTACGGATAT3' (102345-102367 in TCG) (SEQ ID NO:7)
LCV1C-5'TTAATTAAGGCGCGCCAGGCCCGGCCCCAAGTT3' (102368-102384 in TCG) (SEQ ID NO:8)
LCV1D-5'ATGGTACCCTTGGTCTTACTTCACTGTCGA3' (104366-104387 in TCG) (SEQ ID NO:9)

Fig. 5

SEQ ID NO:10

TCGACAGTGAAGTAAGACCAAGCTCATGAGCTTATTATCTCAGGTCGGAACAAGTTGATAGGATCCCCCTTTTT
ACGTCCCCATGCCCCCTGTGTGGCGACATGGGGGCGAAAAAAGGAAAGAGAGAGATGGGGTTTCTCTCGCTTTT
GGCATAGTGGGCCCCCAGTGGGGGGCTCGCACGACGGGCTATTAGCTCAGTGGGTAGAGCGCGCCCCTGATAAT
TGCGTCGTTGTGCCTGGGCTGTGAGGGCTCTCAGCCACATGGATAGTTCAATGTGCTCATCGGCGCCTGACCCT
GAGATGTGGATCATCCAAGGCACATTAGCATGGCGTACTCCTCCTGTTCGAACCGGGGTTTGAAACCAAACTTC
TCCTCAGGAGGATAGATGGGGCGATTCAGGTGAGATCCAATGTAGATCCAACTTTCGATTCACTCGTGGGATCC
GGGCGGTCCGGGGGGGACCACCATGGCTCCTCTCTTCTCGAGAATCCATACATCCCTTATCAGTGTATGGACAG
CTATCTCTCGAGCACAGGTTTAGGTTCGGCCTCAATGGGAAAATAAAATGGAGCACCTAACAACGCATCTTCAC
AGACCAAGAACTACGAGATCACCCCTTTCATTCTGGGGTGACGGAGGGATCATACCATTCGAGCCTTTTTTTTT
CATGCTTTTCCCCGAGGTCTGGAGAAAGCTGAAATCAATAGGATTTCCCTAATCCTCCCTTACCGAAAGGAAGA
GCGTGAAATTCTTTTTCCTTTCCGCAGGGACCAGGAGATTGGATCTAGCCGTAAGAAGAATGCTTGGTATAAAT
AACTCACTTCTTGGTCTTCGACCCCCGCAGTCACTACGAACGCCCCCGATCAGTGCAATGGGATGTGTCTATTT
ATCTATCTCTTGACTCGAAATGGGAGCAGGTTTGAAAAAGGATCTTAGAGTGTCTAGGGTTGGGCCAGGAGGGT
CTCTTAACGCCTTCTTTTTTCTTCTCATCGGAGTTATTTCACAAAGACTTGCCATGGTAAGGAAGAAGGGGGGA
ACAGGCACACTTGGAGAGCGCAGTACAACGGAGAGTTGTATGCTGCGTTCGGGAAGGATGAATCGCTCCCGAAA
AGGAATCTATTGATTCTCTCCCAATTGGTTGGACCGTAGGTGCGATGATTTACTTCACGGGCGAGGTCTCTGGT
TCAAGTCCAGGATGGCCCAGCTGCGCCAGGGAAAAGAATAGAAGAAGCGTCAGACTA<u>TTAATTAAGGCGCGCCC</u>
ATGCATGCTCCACTTGGCTCGGGGGATATAGCTCAGTTGGTAGAGCTCCGCTCTTGCAATTGGGTCGTTGCGA
TTACGGGTTGGATGTCTAATTGTCCAGGCGGTAATGATAGTATCTTGTACCTGAACCGGTGGCTCACTTTTCT
AAGTAATGGGGAAGAGGACCGAAACATGCCACTGAAAGACTCTACTGAGACAAAGATGGGCTGTCAAGAACGTC
AAGAACGTAGAGGAGGTAGGATGGGCAGTTGGTCAGATCTAGTATGGATCGTACATGGACGGTAGTTGGAGTCG
GCGGCTCTCCTAGGGTTCCCTTATCGGGGATCCCTGGGGAAGAGGATCAAGTTGGCCCTTGCAACAGCTTGAT
GCACTATCTCCCTTCAACCCTTTGAGCGAAATGCGGCAAAAGGAAGGAAAATCCATGGACCGACCCCATCATCT
CCACCCCGTAGGAACTACGAGATTACCCCAAGGACGCCTTCGGCATCCAGGGGTCACGGACCGACCATAGAACC
CTGTTCAATAAGTGGAACGCATTAGCTGTCCGCTCTCAGGTTGGGCAGTAAGGGTCGGAGAAGGGCAATCACTC
ATTCTTAAAACCAGCGTTCTTAAGGCCAAAGAGTCGGCGGAAAAGGGGGAAAGCTCTCCGTTCCTGGTTTCCT
GTAGCTGGATCCTCCGGAACCACAAGAATCCTTAGTTAGAATGGGATTCCAACTCAGCACCTTTTGAGTGAGAT
TTTGAGAAGAGTTGCTCTTTGGAGAGCACAGTACGATGAAAGTTGTAAGCTGTGTTCGGGGGGAGTTATTGTC
TATCGTTGGCCTCTATGGTAGAATCAGTCGGGGACCTGAGAGGCGGTGGTTTACCCTGCGGCGGATGTCAGCG
GTTCGAGTCCGCTTATCTCCAACTCGTGAACTTAGCCGATACAAAGCTATATGACAGCACCCAATTTTTCCGAT
TTGGCGGTTCGATCTATGATTTATCATTCATG

Fig. 7-1

```
LCV2   :      1 tcgacagtgaagtaagaccaagctcatgagcttattatctcaggtcggaacaagttgata   60
SEQ ID NO:11    |||||  ||||||||||||||||||||||||||||||||||||  |||||||||||||||||
tobac: 104366 tcgacggtgaagtaagaccaagctcatgagcttattatcctaggtcggaacaagttgata 104425
SEQ ID NO:12

LCV2   :     61 ggatccccttttttacgtccccatg--ccccctgtgtggcgacatgggggcgaaaaaagg  118
                ||| ||||  |||||||||||||||  ||||| |||||||||||||||||||||||||||
tobac: 104426 ggacccccttttttacgtccccatgttccccc-gtgtggcgacatgggggcgaaaaaagg 104485

LCV2   :    119 aaagagagagatggggtttctctcgcttttggcatagtgggcccccagtgggggctcgc  178
                ||||||||  |||||||||||||||||||||||||| ||||||||||||||| |||||||
tobac: 104486 aaagagagggatggggtttctctcgcttttggcatagcgggcccccagtgggaggctcgc 104545

LCV2   :    179 acgacgggctattagctcagtgggtagagcgcgcccctgataattgcgtcgttgtgcctg  238
                ||||||||||||||||||||||||| ||||||||||||||||||||||||||||||||||
tobac: 104546 acgacgggctattagctcagtgg-tagagcgcgcccctgataattgcgtcgttgtgcctg 104604

LCV2   :    239 ggctgtgagggctctcagccacatggatagttcaatgtgctcatcggcgcctgaccctga  298
                ||||||||||||||||||||||||||||||||||||||||||||||||||||||||||||
tobac: 104605 ggctgtgagggctctcagccacatggatagttcaatgtgctcatcggcgcctgaccctga 104664

LCV2   :    299 gatgtggatcatccaaggcacattagcatggcgtactcctcctgttcgaaccggggtttg  358
                ||||||||||||||||||||||||||||||||||||||||||||||||||||||||||||
tobac: 104665 gatgtggatcatccaaggcacattagcatggcgtactcctcctgttcgaaccggggtttg 104724

LCV2   :    359 aaaccaaacttctcctcaggaggatagatggggcgattcaggtgagatccaatgtagatc  418
                ||||||||| ||||||||||||||||||||||||||||| ||||||||||||||||||||
tobac: 104725 aaaccaaactcctcctcaggaggatagatggggcgattcgggtgagatccaatgtagatc 104784

LCV2   :    419 caactttcgattcactcgtgggatccgggcggtccggggggaccaccatggctcctctc   478
                ||||||||||||||||||||||||||||||||||||||||||        |||||||| ||||||||||
tobac: 104785 caactttcgattcactcgtgggatccgggcggtccggggggaccaccacggctcctctc  104844

LCV2   :    479 ttctcgagaatccatacatcccttatcagtgtatggacagctatctctcgagcacaggtt  538
                ||||||||||||||||||||||||||||||||||||||||||||||||||||||||||||
tobac: 104845 ttctcgagaatccatacatcccttatcagtgtatggacagctatctctcgagcacaggtt 104904

LCV2   :    539 taggttcggcctcaatgggaaaataaaatggagcacctaacaacgcatcttcacagacca  598
                |||         ||||||||||||||||||||||||||||||||||||||||||||||||
tobac: 104905 tag---------caatgggaaaataaaatggagcacctaacaacgcatcttcacagacca 104955

LCV2   :    599 agaactacgagatcaccccttcattctggggtgacggagggatcataccattcgagcc   657
                |||||||||||||| |||||||||||||||||||||||||||| ||||||||||||||
tobac: 104956 agaactacgagatcgcccctttcattctggggtgacggagggatcgtaccattcgagcc 105014

LCV2   :    658 ttttttttcatgcttttccccgaggtctggagaaagctgaaatcaataggatttcccta  717
                |||||||
tobac: 105015 gtttttt----------------------------------------------------- 105021
atcctcccttaccgaaaggaagagcgtgaaattcttttccttccgcagggaccaggagattggatctagccgtaagaagaatgcttg
gtataaataactcacttcttggtcttcgaccccgcagtcactacgaacgcccccgatcagtgcaatgggatgtgtctatttatctatc
895
(231 bp present in lettuce maize, rice and soybean but not tobacco)
```

Fig. 7-2

```
(continued)
LCV2  :    896  tcttgactcgaaatgggagcaggtttgaaaaaggatcttagagtgtctagggttgggcca   955
                ||||||||||||||||||||||||||||||||||||||||||||||||||||||||||||
tobac: 105022  tcttgactcgaaatgggagcaggtttgaaaaaggatcttagagtgtctagggttgggcca 105081

LCV2  :    956  ggagggtctcttaacgccttcttttttcttctcatcggagttatttcacaaagacttgcc  1015
                ||||||||||||||||||||||||||||||||||||||||||||||||||||||||||||
tobac: 105082  ggagggtctcttaacgccttcttttttcttctcatcggagttatttcacaaagacttgcc 105141

LCV2  :   1016  atggtaaggaagaagggggggaacaggcacacttggagagcgcagtacaacggagagttgt  1075
                |  |||||||||||||||||||||| ||||||||||||||||||||||||||||||||||
tobac: 105142  agggtaaggaagaagggggggaacaagcacacttggagagcgcagtacaacggagagttgt 105201

LCV2  :   1076  atgctgcgttcgggaaggatgaatcgctcccgaaaaggaatctattgattctctcccaat  1135
                ||||||||||||||||||||||||||||||||||||||||||||||||||||||||||||
tobac: 105202  atgctgcgttcgggaaggatgaatcgctcccgaaaaggaatctattgattctctcccaat 105261

LCV2  :   1136  tggttggaccgtaggtgcgatgatttacttcacgggcgaggtctctggttcaagtccagg  1195
                ||||||||||||||||||||||||||||||||||||||||||||||||||||||||||||
tobac: 105262  tggttggaccgtaggtgcgatgatttacttcacgggcgaggtctctggttcaagtccagg 105321

PacI/AscI
LCV2  :   1196  atgcccagctgcgccagggaaaagaatagaagaagcgtcagactccttaattaaggcgcgcc 1258
                ||||||||||||||||||||||||||||||||||||||||| ||  |||| |||
tobac: 105322  atgcccagctgcgccagggaaaagaatagaagaagcatctgactactt-------------- 105370

LCV2  :   1259  catgcatgctccacttggctcggggggatatagctcagttggtagagctccgctcttgca  1318
                ||||||||||||||||||||||||||||||||||||||||||||||||||||||||||||
tobac: 105371  catgcatgctccacttggctcggggggatatagctcagttggtagagctccgctcttgca 105430

LCV2  :   1319  attgggtcgttgcgattacgggttggatgtctaattgtccaggcggtaatgatagtatct  1378
                ||||||||||||||||||||||||||||||||||||||||||||||||||||||||||||
tobac: 105431  attgggtcgttgcgattacgggttggatgtctaattgtccaggcggtaatgatagtatct 105490

LCV2  :   1379  tgtacctgaaccggtggctcacttttctaagtaatggggaagaggaccgaaacatgcca  1438
                |||||||||||||||||||||||||||||||||||||||||||||||||||||| |||||
tobac: 105491  tgtacctgaaccggtggctcacttttctaagtaatggggaagaggaccgaaacgtgcca 105550

LCV2  :   1439  ctgaaagactctactgagacaaagatgggctgtcaagaacgtcaagaacgtagaggaggt  1498
                |||||||||||||||||||||||||||||||||||||||||||        ||||||||||
tobac: 105551  ctgaaagactctactgagacaaagatgggctgtcaagaa---------cgtagaggaggt 105601

LCV2  :   1499  aggatgggcagttggtcagatctagtatggatcgtacatggacggtagttggagtcggcg  1558
                ||||||||||||||||||||||||||||||||||||||||||||||||||||||||||||
tobac: 105602  aggatgggcagttggtcagatctagtatggatcgtacatggacggtagttggagtcggcg 105661

LCV2  :   1559  gctctcctagggttcccttatcggggatccctggggaagaggatcaagttggcccttgcg  1618
                ||||||| ||||||||||  ||| | ||||  ||||||||||||||||||||||||||||
tobac: 105662  gctctcccagggttccctcatctgagatctctggggaagaggatcaagttggcccttgcg 105721

LCV2  :   1619  aacagcttgatgcactatctcccttcaacccctttgagcgaaatgcggc-----aaaagga 1673
                |||||||||||||||||||||||||||||||||||||||||||||||||     |||||||
tobac: 105722  aacagcttgatgcactatctcccttcaacccctttgagcgaaatgcggcaaagaaaagga 105781
```

Fig. 7-3

```
(continued)
LCV2  : 1674    aggaaaatccatggaccgaccccatcatctccaccccgtaggaactacgagattaccca  1733
                ||||||||||||||||||||||||||||||||||||||||||||||||||||| ||||||
tobac : 105782  aggaaaatccatggaccgaccccatcatctccaccccgtaggaactacgagatcacccca  105841

LCV2  : 1734    aggacgccttcggcatccaggggtcacggaccgaccatagaaccctgttcaataagtgga  1793
                ||||||||||||||||||||||||||||||||||||||||||||||||||||||||||||
tobac : 105842  aggacgccttcggcatccaggggtcacggaccgaccatagaaccctgttcaataagtgga  105901

LCV2  : 1794    acgcattagctgtccgctctcaggttgggcagtaagggtcggagaagggcaatcactcat  1853
                |||||||||||||||||||||||||||||||||||||| |||||||||||||| |||||
tobac : 105902  acgcattagctgtccgctctcaggttgggcagtcagggtcggagaagggcaatgactcat  105961

LCV2  : 1854    tctta  1858
                |
tobac : 105962  t----  105962

LCV21859aaaccagcgttcttaaggccaaagagtcggcggaaaagggggaaagctctccgttcctggtttcctgtagctggatcctc
cggaaccacaagaatc 1955   (97 bp sequence absent in tobacco but present in spinach, Solanum
nigrum, Arabidopsis, Soybean, rice and wheat)

LCV2  : 1956    cttagttagaatgggattccaactcagcacctttgagtgagattttgagaagagttgct  2015
                ||||||||||||||||||||||||||||||||||||||||||||||||||||||||||||
tobac : 105963  cttagttagaatgggattccaactcagcacctttgagtgagattttgagaagagttgct  106022

LCV2  : 2016    ctttggagagcacagtacgatgaaagttgtaagctgtgttcgggggggagttattgtcta  2075
                ||||||||||||||||||||||||||||||||||||||||||||||||||||||||||||
tobac : 106023  ctttggagagcacagtacgatgaaagttgtaagctgtgttcgggggggagttattgtcta  106082

LCV2  : 2076    tcgttggcctctatggtagaatcagtcgggggacctgagaggcggtggtttaccctgcgg  2135
                ||||||||||||||||||||||||||||||||||||||||||||||||||||||||||||
tobac : 106083  tcgttggcctctatggtagaatcagtcgggggacctgagaggcggtggtttaccctgcgg  106142

LCV2  : 2136    cggatgtcagcggttcgagtccgcttatctccaactcgtgaacttagccgatacaaagct  2195
                ||||||||||||||||||||||||||||||||||||||||||||||||||||||||||||
tobac : 106143  cggatgtcagcggttcgagtccgcttatctccaactcgtgaacttagccgatacaaagct  106202

LCV2  : 2196    atatgacagcacccaattttcgatttggcggttcgatctatgatttatcattcatg  2253
                ||||| ||||||||||||||||||| |||||||||||||||||||||||||||||
tobac : 106203  ttatgatagcacccaattttcgattcggcggttcgatctatgatttatcattcatg  106260
```

LCV2A  5' TCGACAGTGAAGTAAGACCAAG3'  (104366-104387 in TCG) (SEQ ID NO:13)
LCV2B  5' <u>GGCGCGCCTTAATTAA</u>GGAGTCAGACGCTTCTTCTATTC3'  (10346-105370 in TCG)
(SEQ ID NO:14)
LCV2C  5' <u>TTAATTAAGGCGCGCC</u>CATGCATGCTCCACTTGGCTCGG3' (105371-105393 in TCG)
(SEQ ID NO:15)
LCV2D  5' CATGAATGATAAATCATAGATCGAAC3'  (106234-106260 in TCG) (SEQ ID NO:16)

LCV1-MSK18 map (9,682bp)

P1  5'-ACTGGAAGGTGCGGCTGGAT-3'  (SEQ ID NO:17)
P2  5'-ACGAGCCGGATGATTAATTGTCAATTAATTAACTA-3'  (MSK18A comp)- (SEQ ID NO:18)
P3  5'-AAGTCACCATTGTTGTGCACG-3'  (starts at 259 bp on aadA CDS) (SEQ ID NO:19)
P4  5'-CTCGCCCTTAATTTTAAGGC-3'  (SEQ ID NO:20)

Fig. 14-1

P1-P2 left border fragment consensus sequence (SEQ ID NO:21)
Primer P1→
<u>actggaaggtgcggctggat</u>cacctccttttcagggagagctaatgcttgttgggtatttggtttgacac
tgcttcacacccaaaaaagaagggagctacgtctgagttaaacttggagatggaagtcttcatttcgtttc
Primer LCV2A→=LCV2A left border
<u>TCGACAGTGAAGTAA</u>GACCAAGCTCATGAGCTTATTATCTCAGGTCGGAACAAGTTGATAGGATCCCCCTT
TTTACGTCCCCATGCCCCCTGTGTGGCGACATGGGGGCGAAAAAAGGAAAGAGAGAGATGGGGTTTCTCTC
GCTTTTGGCATAGTGGGCCCCCAGTGGGGGGCTCGCACGACGGGCTATTAGCTCAGTGGGTAGAGCGCGCC
CCTGATAATTGCGTCGTTGTGCCTGGGCTGTGAGGGCTCTCAGCCACATGGATAGTTCAATGTGCTCATCG
GCGCCTGACCCTGAGATGTGGATCATCCAAGGCACATTAGCATGGCGTACTCCTCCTGTTCGAACCGGGGT
TTGAAACCAAACTTCTCCTCAGGAGGATAGATGGGGCGATTCAGGTGAGATCCAATGTAGATCCAACTTTC
GATTCACTCGTGGGATCCGGGCGGTCCGGGGGGACCACCATGGCTCCTCTCTTCTCGAGAATCCATACAT
CCCTTATCAGTGTATGGACAGCTATCTCTCGAGCACAGGTTTAGGTTCGGCCTCAATGGGAAAATAAAATG
GAGCACCTAACAACGCATCTTCACAGACCAAGAACTACGAGATCACCCCTTTCATTCTGGGGTGACGGAGG
GATCATACCATTCGAGCCTTTTTTTTTCATGCTTTTCCCCGAGGTCTGGAGAAAGCTGAAATCAATAGGAT
TTCCCTAATCCTCCCTTACCGAAAGGAAGAGCGTGAAATTCTTTTTCCTTTCCGCAGGGACCAGGAGATTG
GATCTAGCCGTAAGAAGAATGCTTGGTATAAATAACTCACTTCTTGGTCTTCGACCCCCGCAGTCACTACG
AACGCCCCGATCAGTGCAATGGGATGTGTCTATTTATCTATCTCTTGACTCGAAATGGGAGCAGGTTTGA
AAAAGGATCTTAGAGTGTCTAGGGTTGGGCCAGGAGGGTCTCTTAACGCCTTCTTTTTTCTTCTCATCGGA
GTTATTTCACAAAGACTTGCCATGGTAAGGAAGAAGGGGGAACAGGCACACTTGGAGAGCGCAGTACAAC
GGAGAGTTGTATGCTGCGTTCGGGAAGGATGAATCGCTCCCGAAAAGGAATCTATTGATTCTCTCCCAATT
GGTTGGACCGTAGGTGCGATGATTTACTTCACGGGCGAGGTCTCTGGTTCAAGTCCAGGATGGCCCAGCTG
                                                 PacI       trc promoter→    ←Primer P2
CGCCAGGGAAAAGAATAGAAGAAGCGTCTGACTCC[<u>TTAATTAA</u>][<u>TTGACAATTAATCATCCGGCTCGT</u>]

P3-P6 left border fragment consensus sequence (SEQ ID NO:22)
Primer P3→(aadA gene)
<u>AAGTCACCATTGTTGTGCACG</u>ACGACATCATTCCGTGGCGTTATCCAGCTAAGCGCGAACTGCAATTTGGA
GAATGGCAGCGCAATGACATTCTTGCAGGTATCTTCGAGCCAGCCACGATCGACATTGATCTGGCTATCTT
GCTGACAAAAGCAAGAGAACATAGCGTTGCCTTGGTAGGTCCAGCGGCGGAGGAACTCTTTGATCCGGTTC
CTGAACAGGATCTATTTGAGGCGCTAAATGAAACCTTAACGCTATGGAACTCGCCGCCCGACTGGGCTGGC
GATGAGCGAAATGTAGTGCTTACGTTGTCCCGCATTTGGTACAGCGCAGTAACCGGCAAAATCGCGCCGAA
GGATGTCGCTGCCGACTGGGCAATGGAGCGCCTGCCGGCCCAGTATCAGCCCGTCATACTTGAAGCTAGAC
AGGCTTATCTTGGACAAGAAGAAGATCGCTTGGCCTCGCGCGCAGATCAGTTGGAAGAATTTGTCCACTAC
                       aadA stop/psbA 3' UTR→
GTGAAAGGCGAGATCACCAAGGTAGTCGGCAAA<u>TAA</u>TGTCTAGAGCGATCCTGGCCTAGTCTATAGGAGGT
TTTGAAAAGAAAGGAGCAGTAATCATTTTCTTGTTCTATCAAGAGGGTGCTATTGCTCCTTTCTTTTTTTC
TTTTTATTTATTTACTAGTATTTTACTTACATAGACTTTTTGTTTACATTATAGAAAAAGAAGGAGAGGT
TATTTTCTTGCATTTATTCATGATTGAGTATTCTATTTTGATTTTGTATTTGTTTAAAATTGTAGAAATAG
AACTTGTTTCTCTTCTTGCTAATGTTACTATATCTTTTTGATTTTTTTTCCAAAAAAAAAATCAAATTTT
GACTTCTTCTTATCTCTTATCTTTGAATATCTCTTATCTTTGAAATAATAATATCATTGAAATAAGAAAGA
          AscI                                             trnA gene→
AGAGCTATATTCGA[<u>GGCGCGCC</u>]CATGCATGCTCCACTTGGCTCGGGGGGATATAGCTCAGTTGGTAGA
GCTCCGCTCTTGCAATTGGGTCGTTGCGATTACGGGTTGGATGTCTAATTGTCCAGGCGGTAATGATAGTA
TCTTGTACCTGAACCGGTGGCTCACTTTTTCTAAGTAATGGGGAAGAGGACCGAAACATGCCACTGAAAGA
CTCTACTGAGACAAAGATGGGCTGTCAAGAACGTCAAGAACGTAGAGGAGGTAGGATGGGCAGTTGGTCAG
ATCTAGTATGGATCGTACATGGACGGTAGTTGGAGTCGGCGGCTCTCCTAGGGTTCCCTTATCGGGGATCC

Fig. 14-2

(continued)
```
CTGGGGAAGAGGATCAAGTTGGCCCTTGCGAACAGCTTGATGCACTATCTCCCTTCAACCCTTTGAGCGAA
ATGCGGCAAAAGGAAGGAAAATCCATGGACCGACCCCATCATCTCCACCCCGTAGGAACTACGAGATTACC
CCAAGGACGCCTTCGGCATCCAGGGGTCACGGACCGACCATAGAACCCTGTTCAATAAGTGGAACGCATTA
GCTGTCCGCTCTCAGGTTGGGCAGTAAGGGTCGGAGAAGGGCAATCACTCATTCTTAAAACCAGCGTTCTT
AAGGCCAAAGAGTCGGCGGAAAAGGGGGGAAAGCTCTCCGTTCCTGGTTTCCTGTAGCTGGATCCTCCGGA
ACCACAAGAATCCTTAGTTAGAATGGGATTCCAACTCAGCACCTTTTGAGTGAGATTTTGAGAAGAGTTGC
TCTTTGGAGAGCACAGTACGATGAAAGTTGTAAGCTGTGTTCGGGGGGGAGTTATTGTCTATCGTTGGCCT
CTATGGTAGAATCAGTCGGGGGACCTGAGAGGCGGTGGTTTACCCTGCGGCGGATGTCAGCGGTTCGAGTC
        trnA end
CGCTTATCTCCAACTCGTGAACTTAGCCGATACAAAGCTATATGACAGCACCCAATTTTTCCGATTTGGCG
←Primer LCV2D = RB of LCV2
gttcgatctatgatttatcattcatggacgttgataagatccatccatttagcagcaccttaggatggcat
        ←Primer P6
agccttaaaattaagggcgag
```

LEC1 (dicistronic)

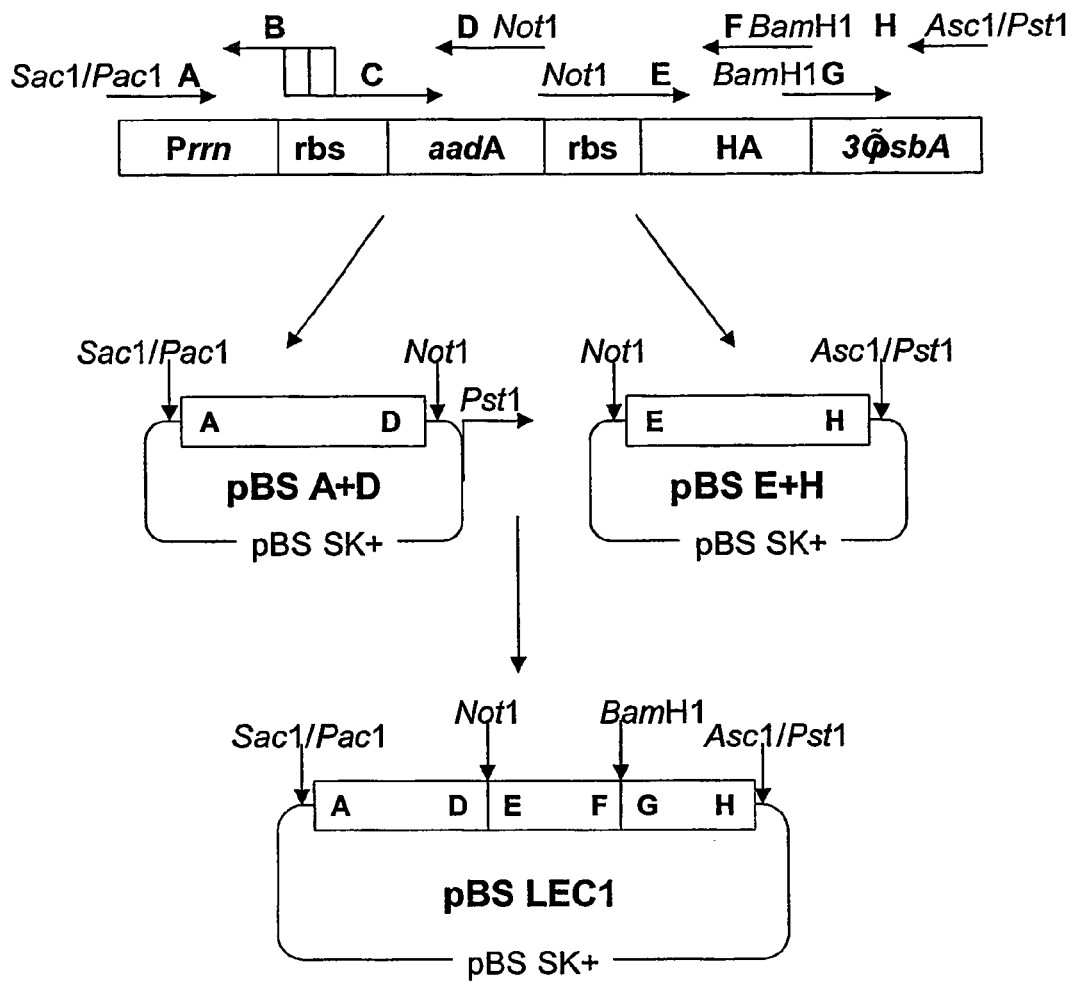

List of PCR primers used in LEC1 construction:

| | |
|---|---|
| LEC1 A | tcg agc tct aaa tta agc tac ccc gcc gtg att gaa tga gaa t (SEQ ID NO:23) |
| LEC1 B | aaa tcc ctc cct aca act gta tcc aag cgc ttc gta ttc gc (SEQ ID NO:24) |
| LEC1 C | gtt gta ggg agg gat tta tgg cag aag cgg tga tcg ccg aa (SEQ ID NO:25) |
| LEC1 D | tcg cgg ccg ctt att gca cga cta cct tgg tga t (SEQ ID NO:26) |
| LEC1 E | tcg cgg ccg cag ttg tag gga ggg att tat gca aaa act ccg gaa tga caa (SEQ ID NO:27) |
| LEC1 F | gga tcc tta gta tcc tga ctt cag ctc aac (SEQ ID NO:28) |
| LEC1 G | aac att aag gat cca gac ttt ggt ctt att gta att gta tag (SEQ ID NO:29) |
| LEC1 H | atc tgc agg gcg gcc atc cac ttg gct aca tcc gcc (SEQ ID NO:30) |

METHOD OF PLASTID TRANSFORMATION IN *ASTERACEAE*, VECTOR FOR USE THEREIN AND PLANTS THUS OBTAINED

FIELD OF THE INVENTION

The invention relates to methods of genetically transforming plant plastids, and more specifically to genetically transforming the plastid genomes of *Asteraceae* plant species. The invention further relates to vectors for use in the transformation of plastid genomes and to transplastomic plants thus obtained and their progeny.

BACKGROUND OF THE INVENTION

Plastids are self-replicating organelles containing their own DNA in a single circular chromosome, called their genome. Plastids are found in all plant cells. They are inherited maternally in most plants just like mitochondria in animals and plants. This is also called cytoplasmic inheritance since these organelles are present in the cytosol of the ova.

Plant plastids (e.g. chloroplasts, amyloplasts, elaioplasts, etioplasts, chromoplasts, leucoplasts and proplastids) are the organelles in which major biochemical processes (i.e. photosynthesis) take place. In general, plant cells contain between 100-10,000 copies of the small 120-160 kb circular plastid genome. Since each molecule has one inverted repeat it is theoretically possible to obtain plant cells with 20,000 copies of (a) gene(s) of interest, after plastid transformation.

The genetic transformation of the plastid genome (plastome) has major advantages over nuclear transformation. Firstly, because in most plant species, plastids are maternally inherited, out-crossing of transgenes to weeds or other crops is minimized. Thus, this form of genetic engineering of plants lowers the risk of dissemination of the transgene in the environment through pollen dispersal. Furthermore, the plastid genome is highly polyploid, enabling the introduction of many copies per cell which can lead to high accumulation levels of the desired protein(s). The fact that plastids are able to form disulfide bonds and to fold proteins, makes this technique in theory ready for the production of biopharmaceuticals in plants.

The principle of plastid transformation is insertion of sequences through homologous recombination. Plastid transformation vectors use two targeting DNA segments that flank the gene or genes of interest. By means of homologous recombination these segments can insert the foreign gene or genes at a precise, predetermined position in the plastid genome. Position effects and gene silencing, major problems in nuclear transformation experiments, have not as yet been observed in plastid transformation events.

However, successful chloroplast transformation of crop plants is described thus far only for Solanaceous crops like potato, tomato, tobacco (U.S. Pat. No. 5,451,513; Svab et al. (1990), Proc. Natl. Acad. Sci. USA 87:8526-8530) and *Brassicaceae*, like *Arabidopsis thaliana* (U.S. Pat. No. 6,376,744). It is not obvious that the techniques used for these species can be readily used for other species such as *Asteraceae*, in particular lettuce.

It is therefore the object of the invention to provide an alternative plastid transformation method that is in particular useful for transforming *Asteraceae* plant species, such as lettuce (*Lactuca sativa*). Lettuce is an agronomical important crop and a useful transformation method therefore is thus highly desirable.

SUMMARY OF THE INVENTION

The invention thus provides a method for the transformation of plastid genomes of plant species, in particular *Asteraceae* plant species, comprising the steps of:
  a) providing a transformation vector;
  b) subjecting a plant material, which comprises plastids, to a transformation treatment in order to allow the plastids to receive the transformation vector;
  c) placing the thus treated plant material for a period of time into contact with a culture medium without selection agent;
  d) subsequently placing the plant material into contact with a culture medium comprising a selection agent; and
  e) refreshing the culture medium comprising a selection agent to allow plant material comprising plastids that have acquired the DNA of interest to grow into transformants, in particular transplastomic plants or plant parts (i.e. plants or plant parts carrying one or more transgenes in their plastids).

The transformation vector may comprise:
  an expression cassette which comprises optionally a promoter active in the plastids of the plant species to be transformed, a DNA insertion site for receiving the transforming DNA of interest, optionally one or more selection markers conferring a selectable phenotype on cells having plastids that are transformed with the expression cassette, and optionally a DNA sequence encoding a transcription termination region active in the plastids of the plant species to be transformed,
  optionally a set of DNA targeting segments located on either side of the expression cassette that allow double homologous recombination of the expression cassette with the plastid genome of interest, and
  a DNA sequence of interest inserted into the insertion site of the expression cassette.

Preferably the vector comprises a promoter, a set of targeting segments and one or more selection markers. However, these elements may also be provided in another way. For example, the DNA of interest can be inserted at such a position in the plastome that it can use an already present promoter, such as in an operon. If no targeting segments are present the DNA of interest can integrate at a random position. The DNA of interest is preferably integrated in the plastid genome but can also exist outside the plastome.

The DNA of interest can be either stably integrated or transiently expressed.

It is surprising that when using the method of the invention no escapes are found in the transformation of plastids of lettuce. The results of plastid transformations thus far, mention the occurrence of escapes (due to nuclear or spontaneous mutants; Kofer et al. (1998) In Vitro Cell. Dev. Biol. Plant 34:303-309).

It was surprisingly found that not immediately starting the selection process but keeping the treated plant material in or on a culture medium for a few days highly improved the efficiency of transformation. In addition, the selection procedure should not be started too late in the culture process. Preferably, selection is started after a maximum of 2-5 days. The moment to start the selection process depends on the transformation method. Another important aspect of the invention is to keep the transformed cells into close contact with the selective agent for a period of time, preferably until regeneration. In addition, it is preferred to retain the concentration of the selective agent at an efficient level, such as 500 mg/l spectinomycin dihydrochloride. This is preferably achieved by using a liquid medium containing the selective agent.

DETAILED DESCRIPTION OF THE INVENTION

The invention provides methods and vectors for efficient and stable transformation of plastids of an *Asteraceae* plant species, in particular chloroplasts of a lettuce plant, and the plants thus obtained.

Other plastids that can be transformed by the method of the invention are selected from the group consisting of amyloplasts, elaioplasts, etioplasts, chromoplasts, leucoplasts and proplastids.

The vector that is used in the method of the invention has a vector backbone and in addition a DNA construct that optionally comprises one or more sets of targeting DNA segments that are homologous to a sequence in the plastid genome, optionally a promoter sequence, optionally a DNA sequence encoding the transforming gene inserted in an insertion site, optionally a terminator sequence, and optionally at least one DNA sequence encoding a selectable marker.

Preferably, the vector comprises the targeting DNA segments, the DNA sequence encoding the transforming gene, a promoter and a selectable marker.

The promoter is any promoter that is active in the plastids of the plant species to be transformed and for lettuce for example selected from the group of (lettuce or other plant species) chloroplast specific ribosomal RNA operon promoter rrn (16S rRNA), psbA, rbcL, trnV, or rps16. However, additional promoter regions, to enhance transcription, translation or both processes, can also be used for obtaining expression of the selectable marker and gene of interest in lettuce plastids. Also, bacterial promoters can be used for expressing genes in the plastids.

The terminator is any terminator that is active in the plant species to be transformed and for lettuce for example selected from the group consisting of the psb A termination sequence, rrn, rbcL, trnV, or rps16. These and other terminators may be specific for lettuce or other plant species. A terminator sequence need not always be present in bicistronic constructs, being two open reading frames behind one promoter. Additional UTR (untranslated region) sequences, fused to coding sequences of desired gene(s), can be used as leader and/or trailer, to minimize unwanted recombination.

The selection marker is for example selected from the group consisting of spectinomycin, streptomycin, kanamycin, hygromycin and chloramphenicol, or to plant herbicides like glyphosate or bialaphos. Of these markers the aadA gene is preferred because it is a non-lethal marker.

Alternatively a visual marker can be used, such as gfp (green fluorescence protein). In that case the selective agent is not a compound or composition but the means that is used to visualize the visual marker, such as the source of blue light that leads to fluorescence of the gfp.

When only such visual marker is used for selecting the transformants, steps d) and e) of the method can be performed without selective agent. The selection is then made visually by illuminating the putative transformants with an appropriate source of light and selecting the transformants that show fluorescence.

The DNA segments that allow double homologous recombination of the DNA of interest with the plastid genome of interest have a DNA sequence that is homologous to a part of the plastid genome. The segments are selected such that integration of the transforming gene takes place in a desired position in the genome. For lettuce, for instance, the set of DNA segments is selected from the trnI(oriA)/trnA region and the 16S/trnV/ORF70B region of the lettuce chloroplast genome. Preferably, the set of DNA segments is selected from LCV1 A-B and LCV1 C-D, and LCV2 A-B and LCV2 C-D as disclosed in the Examples. The advantage of these segments is that they were found to be particularly useful for lettuce.

The method of the invention can be used for the preparation of plants that can express any gene of interest. The inventive technology can be used for the transformation of plastids from any plant, but in particular for plants of the *Asteraceae* family, more in particular for lettuce. The invention can thus be used for the production of polypeptides that can be isolated from the plant or of polypeptides that are useful for the plant itself. An example of production of products that can be isolated from the plant lies for example in the field of biopharmaceuticals, i.e. pharmaceuticals produced in living organisms such as plants. The production in plants has high potential because it can lead to lower production costs as compared to production in animals or in microorganisms using Bioreactors.

A promising new field in which this invention can be used is the production of edible vaccines, but other pharmaceuticals, either therapeutic or prophylactic, can be envisaged as well as (poly)peptides that can be used in other fields.

In addition to using the plant as a factory for the production of peptides or polypeptides, the product expressed can also be of agronomical importance. Examples are herbicide resistance, insect resistance, fungal resistance, bacterial resistance, stress tolerance for instance to cold, high salt or minerals, yield, starch accumulation, fatty acid accumulation, photosynthesis.

According to the invention, the transformation treatment is selected from the group consisting of electroporation, particle gun transformation, polyethylene glycol transformation and whiskers technology. Polyethylene glycol transformation and particle gun are very advantageous since a high number of cells can be transformed simultaneously and an efficient selection of the transformed plastids within the cells can take place.

The essence of the whiskers technology is the microscopic needle-like silicon-carbide "whiskers" which are approximately 0.6 microns in diameter and vary from 5-80 microns in length. The process begins with the provision of a "transformation cocktail" consisting of DNA, silicon carbide "whiskers", and the appropriate plant target tissue. This cocktail is then stirred or mixed or shaken in a robust fashion by a variety of means (such as a Vortex Machine, a Dental Amalgam Mixer, or a Commercial Paint Shaker). The resulting collisions between plant cells and "whiskers" are hypothesized to result in the creation of very small openings in the plant cell wall and membrane. As a consequence, DNA can move into the targeted plant cells, followed by integration of the transforming DNA into the plastome. Ultimately, transplastomic plant material can be recovered.

The period of time during which the treated plant material is placed into contact with a culture medium without selection agent depends on the transformation treatment. For polyethylene glycol transformation the period of time is 1 to 14 days, preferably 3 to 7 days, more preferably about 6 days. For particle gun transformation, the period of time during which the treated plant material is placed into contact with a culture medium without selection agent is 1 to 14 days, preferably 1-5 days, more preferably about 2 days. "Without selection agent" is intended to mean "without an effective amount of the selection agent". During this period a low, i.e. ineffective amount of selective agent may be present.

The step of placing the treated plant material into contact with a culture medium without selection agent was found to be important for the transformation efficiency. In addition it is preferred for chloroplast transformation to keep the treated plant material in the dark during this step. This way no new and thus not transformed chloroplasts are produced thus leading to a higher efficiency.

The treated plant material is preferably kept into contact with a culture medium with the selection agent until regeneration of the plant or plant part from the transformed material.

The method of the invention is suitable for plant materials selected from plant tissue, separate cells, protoplasts, separate plastids.

It was surprisingly found that the transformation efficiency can be increased when the culture medium comprising the selection agent is a liquid medium. This way the cells to be transformed are in close contact with the selective agent. It was furthermore surprisingly found that no escapes were detected in the transformation experiments.

When the culture medium is refreshed after the selection procedure this may mean that fresh medium with selective agent is added (i.e. so that the selection medium is not diluted) or that the selection medium is changed for medium with selective agent.

The invention further relates to an expression vector for the transformation of plastid genomes of plant species, in particular *Asteraceae* plant species, which vector comprises:
- an expression cassette which comprises optionally a promoter active in the plastids of the plant species to be transformed, a DNA insertion site for receiving the transforming DNA of interest, optionally one or more selection markers conferring a selectable phenotype on cells having plastids that are transformed with the expression cassette, and optionally a DNA sequence encoding a transcription termination region active in the plastids of the plant species to be transformed,
- optionally a set of DNA targeting segments located on either side of the expression cassette that allow double homologous recombination of the expression cassette with the plastid genome of interest, and
- optionally a DNA sequence of interest inserted into the insertion site of the expression cassette.

In a preferred embodiment, the vector comprises the promoter, the one or more selection markers and the set of DNA targeting segments. Such vector comprises:
- an expression cassette which comprises a promoter active in the plastids of the plant species to be transformed, a DNA insertion site for receiving the transforming DNA of interest, one or more selection markers conferring a selectable phenotype on cells having plastids that are transformed with the expression cassette, and optionally a DNA sequence transcription termination region active in the plastids of the plant species to be transformed, and
- a set of DNA targeting segments located on either side of the expression cassette that allow double homologous recombination of the expression cassette with the plastid genome of interest.

The various elements of the vector are preferably as described above for the method. The invention relates both to the vector in which no gene to be transformed is incorporated as well as to the vector comprising any transformable gene.

The vectors of the invention provide stable transformation of plastids of multicellular structures, such as plants of lettuce.

The invention further relates to plants carrying in their cells plastids that are transformed, in particular to plants carrying plastids transformed by means of the method of the invention. In addition, the invention relates to progeny of these plants in which at least part of the transformed plastids are still present.

The invention will be further illustrated in the Examples that follows. In these examples, as explant material, lettuce plant mesophyl protoplasts are used and via PEG transformation transplastomic protoplast-derived colonies and regeneration of plants were obtained. Alternatively, transplastomic callus was obtained using particle bombardment of excised cotyledons of lettuce. The DNA constructs comprise an expression cassette containing the transforming DNA which is targeted to a pre-determined location in the plastid genome and inserted into the plastid genome by homologous recombination. The targeting segments in the cassette comprise preferred sequences of the lettuce DNA chloroplast genome, i.e. the trnI(oriA)/trnA region or the 16S/trnV/ORF70B region of the lettuce chloroplast genome. The DNA used for transformation further contains a non-lethal selectable marker gene which confers a selectable phenotype on cells having the plastids with the transforming DNA, in this case spectinomycin. The non-lethal selectable coding sequence preferred, is the coding region of aadA from *E. coli*, which encodes aminoglycoside-3'-adenylyltransferase to confer spectinomycin and streptomycin resistance. Furthermore, the DNA expression cassette comprises at least one additional DNA sequence, which is the DNA sequence of interest, such as a gene encoding a green fluorescent protein (gfp) (as a model system) or the influenza virus haemagglutinin gene (HA). The constructs furthermore are provided with a promoter and a terminator sequence functional in plant plastids.

In the Examples that follow reference is made to the following figures:

BRIEF DESCRIPTION OF THE DRAWINGS

FIG. 1. LCV1 lettuce chloroplast genome target sequence (not including backbone vector) (SEQ ID NO:1).

FIG. 3. LCV1 lettuce chloroplast genome target sequence (SEQ ID NO:2) aligned with tobacco chloroplast genome (GI Z00044) (SEQ ID NO:3). SEQ ID NO:4 and 5 are the hypothetical proteins. SEQ ID NO:41 is the ribosomal protein.

FIG. 5. LCV2 lettuce chloroplast genome target sequence (not including backbone vector) (SEQ ID NO:10).

FIG. 7. LCV2 lettuce chloroplast genome target sequence (SEQ ID NO:11) aligned with tobacco chloroplast genome (GI Z00044) (SEQ ID NO:12).

FIG. 9. Map of LCV1 MSK18 (9,682 bp).

Panel A: PCR products of the ATPase gene.
Lane 1. Marker,
 2. TRSL5-01016 pLCV2-MSK18-1,
 3. TRSL5-01016 pLCV2-MSK18-1

4. TRSL5-02002 pLCV2-MSK18-1-1,
5. TRSL5-02002 pLCV2-MSK18-1-2,
6. TRSL5-02002 pLCV2-MSK18-2-1,
7. TRSL5-02002 pLCV2-MSK18-2-1,
8. TRSL5-02002 pLCV2-MSK18-2-2,
9 and 10 untransformed callus,
11 and 12 pLCV2-MSK18

Panel B: PCR products of the AadA gene.
Lane 1. Marker,
2. TRSL5-01016 pLCV2-MSK18-1,
3. TRSL5-01016 pLCV2-MSK18-1
4. TRSL5-02002 pLCV2-MSK18-1-1,
5. TRSL5-02002 pLCV2-MSK18-1-2,
6. TRSL5-02002 pLCV2-MSK18-2-1,
7. TRSL5-02002 pLCV2-MSK18-2-1,
8. TRSL5-02002 pLCV2-MSK18-2-2,
9 and 10 untransformed callus,
11 and 12 pLCV2-MSK18

Panel C: PCR products of the trnI junction.
Lane 1. Marker,
2. TRSL5-01016 pLCV2-MSK18-1,
3. TRSL5-01016 pLCV2-MSK18-1
4. TRSL5-02002 pLCV2-MSK18-1-1,
5. TRSL5-02002 pLCV2-MSK18-1-2,
6. TRSL5-02002 pLCV2-MSK18-2-1,
7. TRSL5-02002 pLCV2-MSK18-2-1,
8. TRSL5-02002 pLCV2-MSK18-2-2,
9 untransformed callus Panel D: PCR products of the trnA junction.
Lane 1. Marker,
2. TRSL5-01016 pLCV2-MSK18-1,
3. TRSL5-01016 pLCV2-MSK18-1
4. TRSL5-02002 pLCV2-MSK18-1-1,
5. TRSL5-02002 pLCV2-MSK18-1-2,
6. TRSL5-02002 pLCV2-MSK18-2-1,
7. TRSL5-02002 pLCV2-MSK18-2-1,
8. TRSL5-02002 pLCV2-MSK18-2-2,
9 untransformed callus FIG. 14. Sequence of left border (P1-P2) (SEQ ID NO:21) and right border (P3-P6) (SEQ ID NO:22) integration junction fragments amplified by PCR from transplastomic lettuce DNA. Sequence in lower case is lettuce chloroplast DNA external to the LCV2 vector target region. Upper panel: P1-P2 left border fragment consensus sequence; Lower panel: P3-P6 left border fragment consensus sequence.

Figure 15:
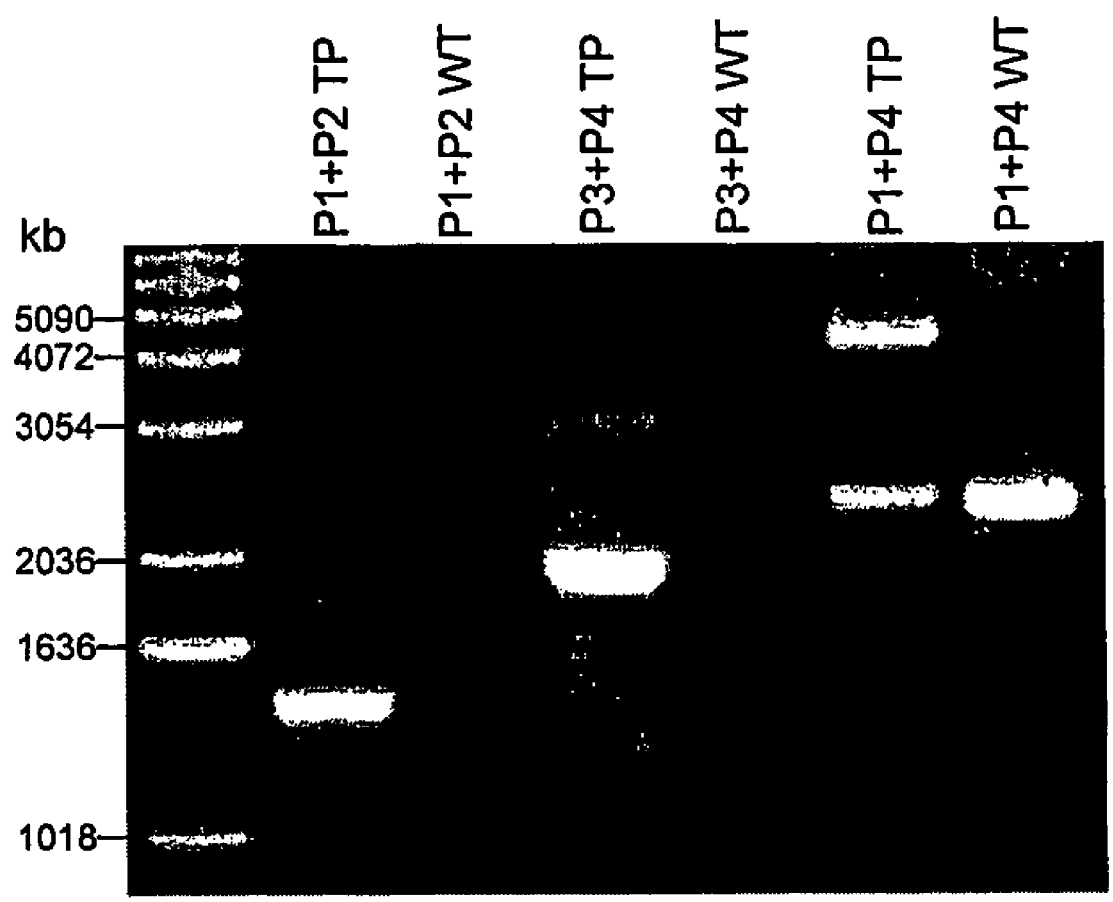

FIG. 15. Agarose gel electrophoresis of PCR products from reactions with primer pairs P1+P2, P3+P4 and P1+P4 and template DNA from spectinomycin resistant putative transplastomic callus sample B (TP) and non-transformed wild-type callus (WT).

Figure 16:
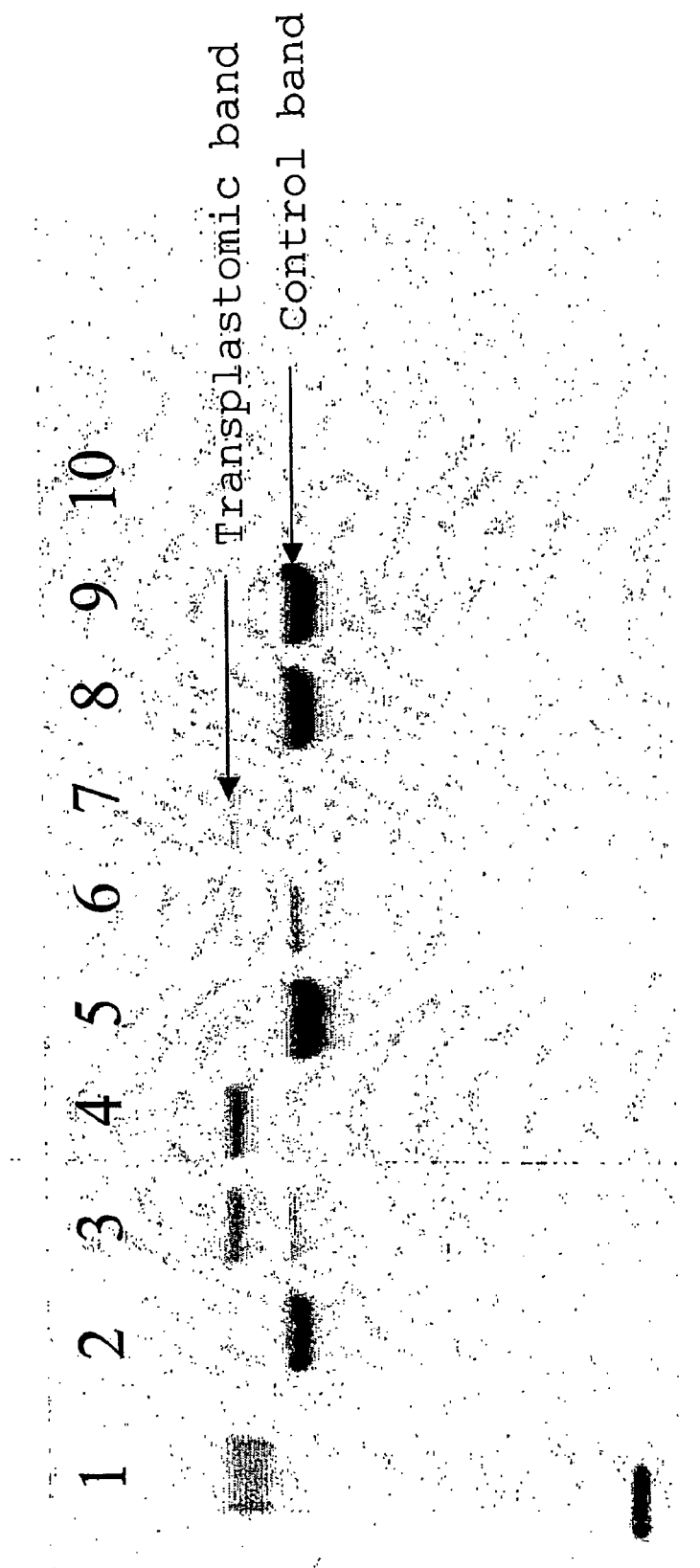

FIG. 16. PCR analysis on insert integration of pLCV2-MSK18 transformed calli. Lane 1: marker DNA, lanes 2-7: TRSL05-02002 pLCV2-MSK18-1-1, TRSL05-02002 pLCV2-MSK18-1-2, TRSL05-02002 pLCV2-MSK18-1-3, TRSL05-02002 pLCV2-MSK18-2-1, TRSL05-02002 pLCV2-MSK18-2-2, TRSL05-02001 pLCV2-MSK18-1-1, respectively; lane 8 and 9: control lettuce DNA, lane 10: plasmid DNA pLCV2-MSK18

Figure 17:
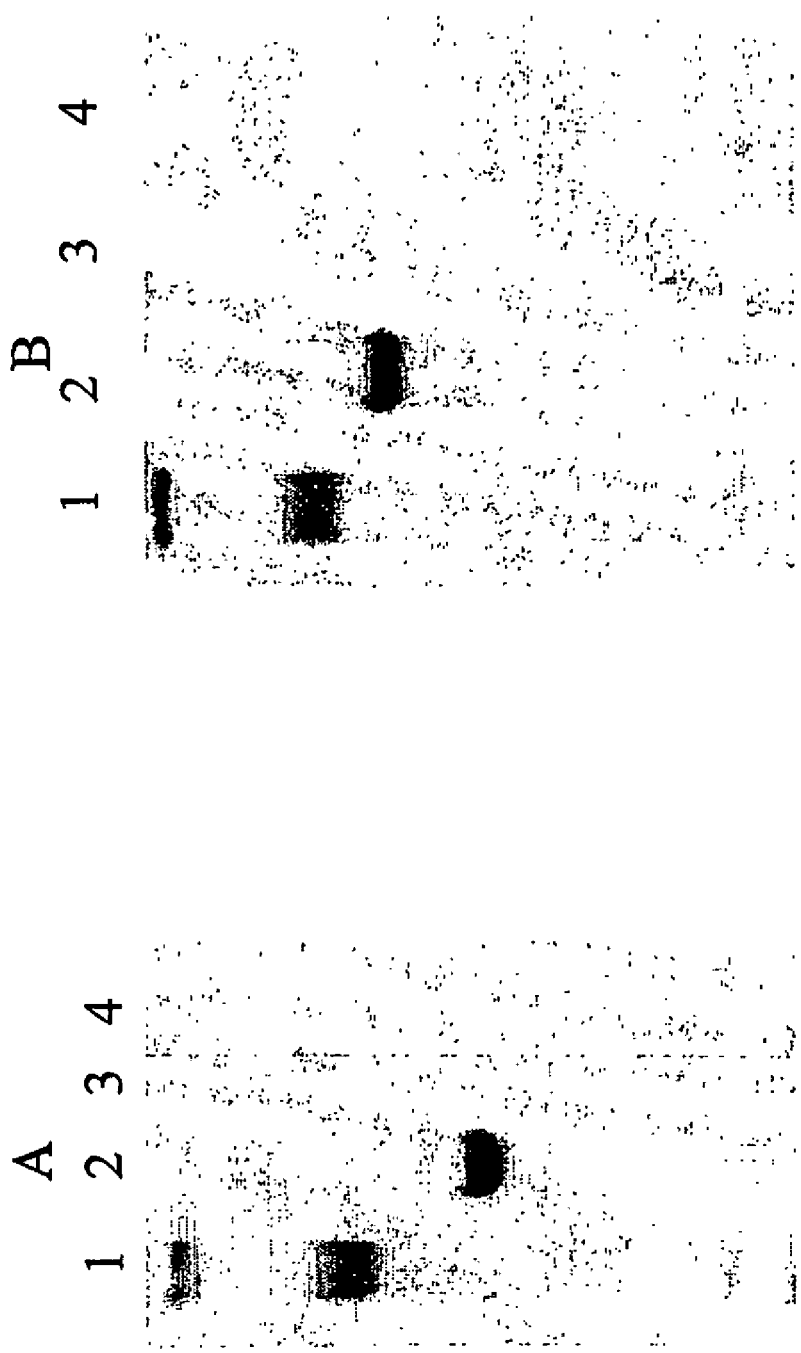

FIG. 17. PCR analysis of left and right border integration junction from callus, derived after particle bombardment transformation with plasmid pLCV2-MSK18. Panel A: trnI junction (left integration junction). Panel B: trnA junction (right border insertion). Lane 1: lambda marker, lane 2: spectinomycin resistant callus pLCV2-MSK18, lane 3: control lettuce, lane 4: plasmid pLCV2-MSK18.

Figure 18:
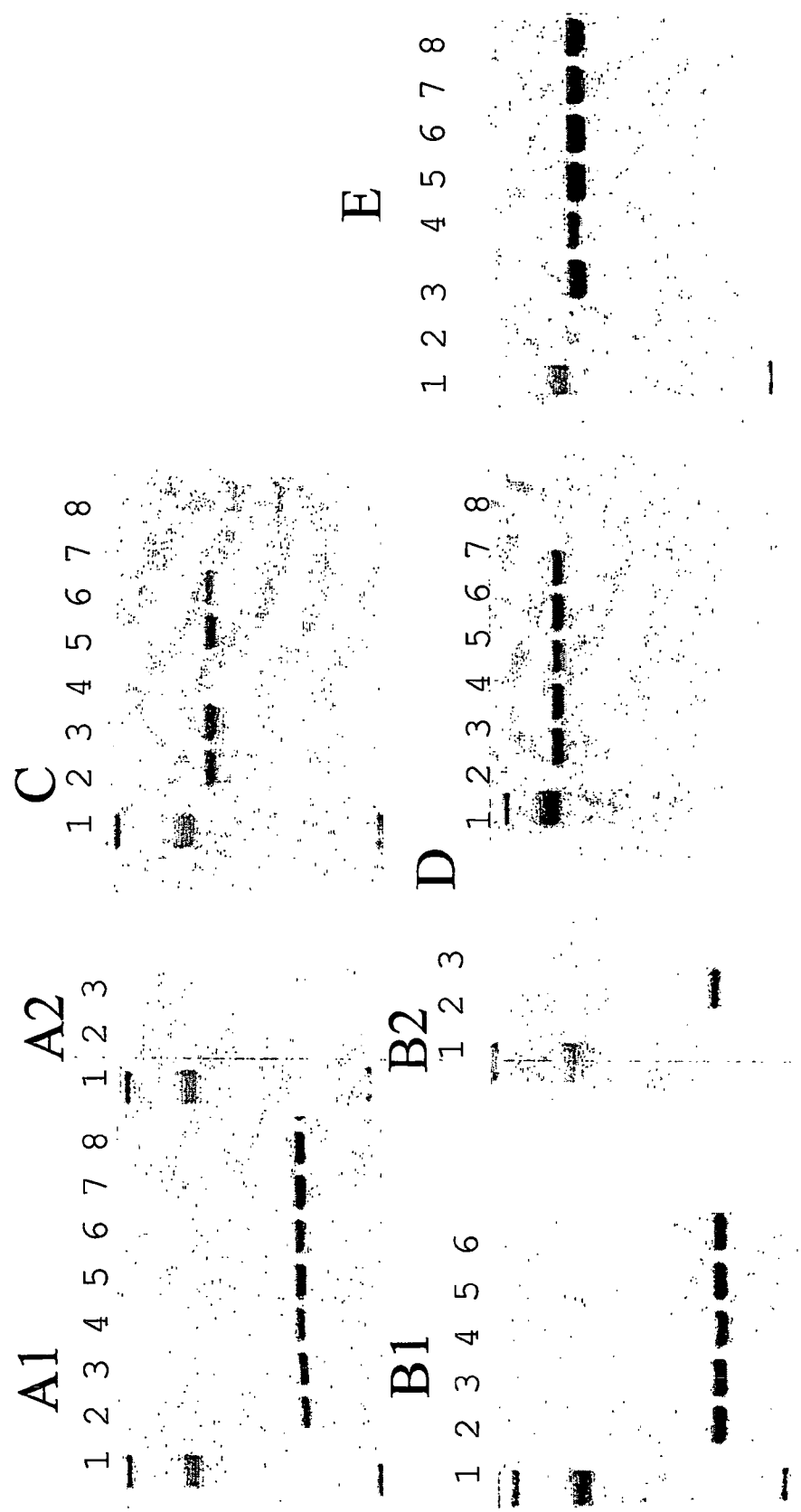

FIG. 18. PCR analysis of pLCV2-LEC1 callus lines and controls.

A1: PCR products of the ATPase gene.
Lane 1; marker
2: pLCV2-LEC1 1.1
3: pLCV2-LEC1 2.1
4: pLCV2-LEC1 2.2
5: pLCV2-LEC1 3.1
6: pLCV2-LEC1 3.2
7: control non-treated lettuce callus
8: control untransformed callus A2: PCR products of ATPase gene
Lane 1: marker
2: plasmid pLCV2-LEC1
3: water B1: PCR products of the AadA gene.
Lane 1; marker
2: pLCV2-LEC1 1.1
3: pLCV2-LEC1 2.1
4: pLCV2-LEC1 2.2
5: pLCV2-LEC1 3.1
6: pLCV2-LEC1 3.2

B2: PCR products of AadA gene
Lane 1: marker
2: plasmid pLCV2-LEC1
3: water

C: PCR products of trnI junction (left border)
Lane 1; marker
2: pLCV2-LEC1 1.1
3: pLCV2-LEC1 2.1
4: pLCV2-LEC1 2.2
5: pLCV2-LEC1 3.1
6: pLCV2-LEC1 3.2
7: control non-treated lettuce DNA
8: plasmid pLCV2-LEC1

D: PCR products of trnA junction (right border)
Lane 1; marker
2: pLCV2-LEC1 1.1
3: pLCV2-LEC1 2.1
4: pLCV2-LEC1 2.2
5: pLCV2-LEC1 3.1
6: pLCV2-LEC1 3.2
7: control non-treated lettuce DNA
8: plasmid pLCV2-LEC1

E: PCR products of insert
Lane 1; marker
2: pLCV2-LEC1 1.1
3: pLCV2-LEC1 2.1
4: pLCV2-LEC1 2.2
5: pLCV2-LEC1 3.1
6: pLCV2-LEC1 3.2
7: control non-treated lettuce callus
8: control untransformed callus FIG. 19. PCR analysis on insert integration in 24 different transplastomic regenerants, originated from 1 transplastomic callus TRSL05-02002 pLCV2-MSK18 1-2 (Lanes A-L and M-X) and 2 control lettuce plants (control lettuce)

Figure 20:
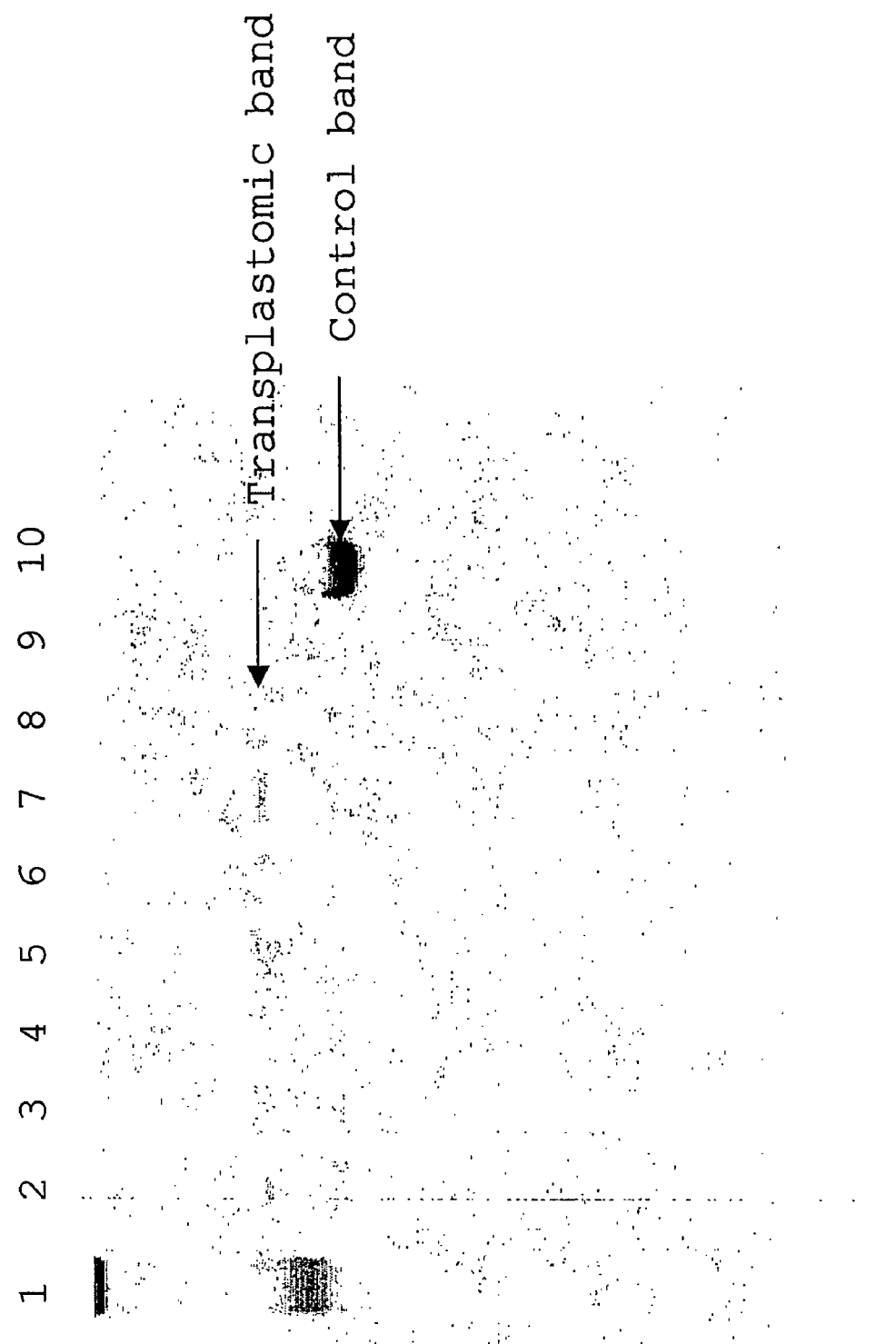

FIG. 20. PCR analysis on insert integration in 7 different transplastomic regenerants, originated from 1 transplastomic callus number pLCV2-LEC1 2.2. Lane 1: marker, lanes 2-8: pLCV2-LEC1 2.2 regenerated plants, lane 9: plasmid DNA pLCV2-LEC1, lane 10: control lettuce DNA.

Figure 21:

FIG. 21. Lettuce expression cassette LEC1. LPrrn—lettuce specific RNA operon promoter; L3' psbA—lettuce specific psbA terminator sequence.

FIG. 22. Schematic representation of the PCR and cloning strategy used for LEC1 construction together with primer sequences (SEQ ID NOS:23-30).

EXAMPLES

Example 1

Vector Constructions

2. Construction of LCV1

Figure 2:
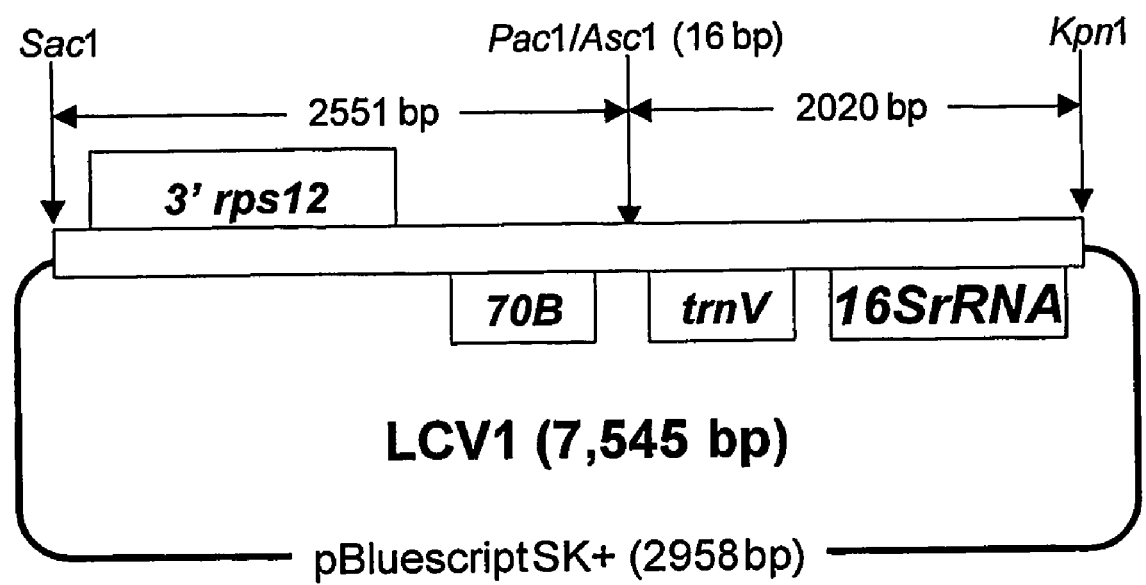
FIG. 2. Map of LCV1 (7,545 bp).
Figure 4:
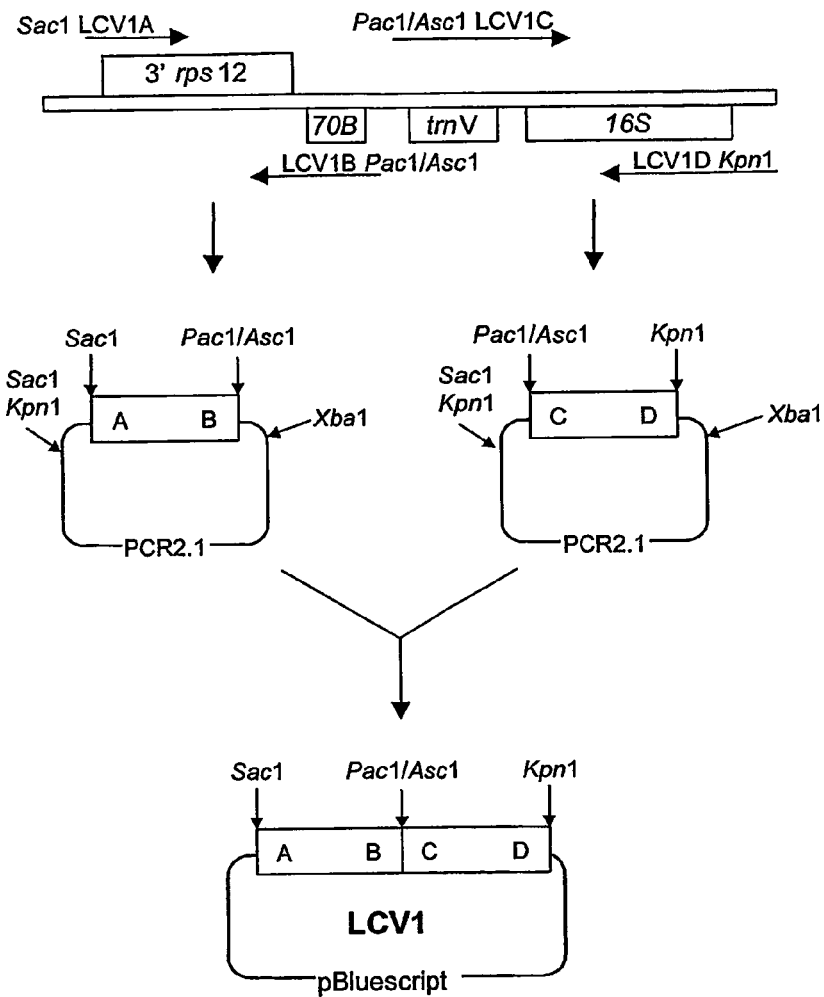
FIG. 4. Cloning steps and primers (SEQ ID NOS:6-9) for construction of LCV1. TCG=tobacco chloroplast genome.

The lettuce chloroplast vector LCV1 consists of 4571 bp of lettuce chloroplast genome sequence with a unique 16 bp Pac1/Asc1 site added (FIG. 1), cloned into Sac1/Kpn1 restriction sites on the polylinker of a pBluescript SK+ backbone vector (FIG. 2). The lettuce sequence spans from the rps7/3'-rps12 intergenic region to the 16SrRNA/trnI intergenic region and corresponds to nucleotide positions 100021-104387 in the tobacco chloroplast genome (GI accession number Z00044). An alignment of this lettuce sequence with the tobacco chloroplast genome sequence is given in FIG. 3. The following description of the construction of LCV1 is outlined in FIG. 4.

Four primers LCV1A, LCV1B, LCV1C and LCV1D were used to amplify this region in two halves (LCV1A-B and LCV1C-D) and to introduce a unique Pac1/Asc1 restriction site in the ORF70B/trnV intergenic region at the position corresponding to nt 102367 in the tobacco chloroplast genome sequence. DNA from clone 6 of the Sac1 library of the lettuce chloroplast genome (Jansen and Palmer, Current Genetics 11: 553-564 (1987)) was used as a template for the LCV1 vector. LCV1A and LCV1B amplified a 2575 bp fragment (2551 bp lettuce sequence+24 bp extension) LCV1A-B spanning from the rps7/3'-rps12 intergenic to the ORF70B/trnV intergenic region (corresponding to 100021-102367 in the tobacco chloroplast genome). Primer LCV1A contains a Sac1 site and LCV1B contains Pac1/Asc1 sites so that Sac1 and Pac1/Asc1 sites are incorporated at the 5' and 3' end, respectively, of the LCV1A-B fragment.

The LCV1 A-B fragment was cloned into the *E.coli* plasmid vector PCR2.1 to create PCR2.1 LCV1A-B. These clones were screened for orientation using Sac1 and Sac1+Xba1. The Sac1/Xba1 insert was cloned into the polylinker of pBluescript to create pBSLCV1 A-B.

Primers LCV1C and LCV1D amplified a 2042 bp fragment (2020 bp lettuce sequence+22 bp extension) LCV1 C-D. The LCV1C primer contains Pac1/Asc1 sites and the LCV1D primer contains a Kpn1 site so that a Pac1/Asc1 and a Kpn1 site are added to the 5' and 3' end, respectively, of the LCV1 C-D fragment. The LCV1 C-D fragment was cloned into PCR2.1 to create PCR2.1 LCV1 C-D. For the final cloning step, PCR2.1 LCV1 C-D was restricted with Asc1+Kpn1 to release a 2031 base pair insert that was ligated to pBS A-B, which was linearised with Asc1+Kpn1, creating LCV1.

2. Construction of LCV2

Figure 6:
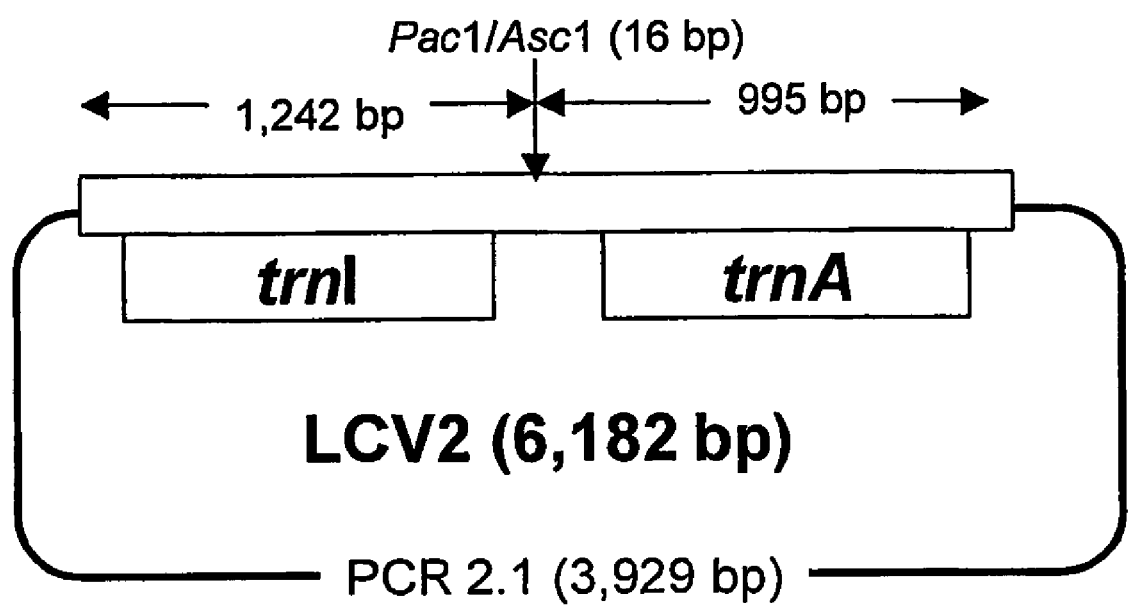
FIG. 6. Map of LCV2 (6,182 bp).
Figure 8:
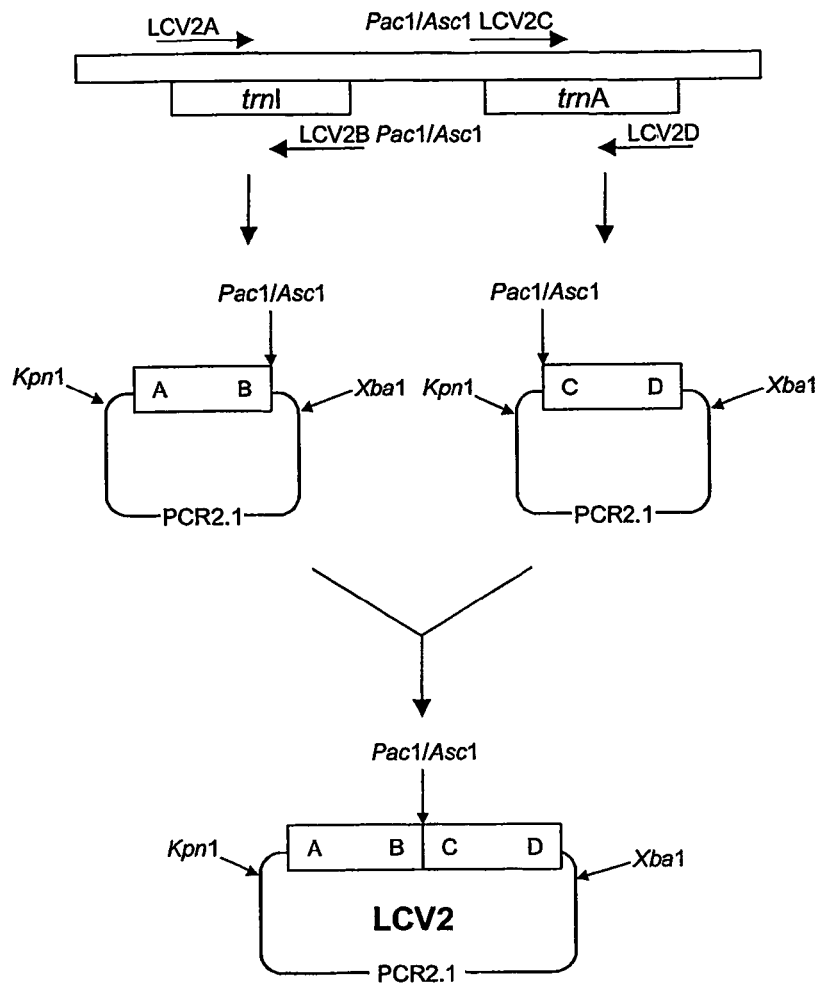
FIG. 8. Cloning steps and primers (SEQ ID NOS:13-16) for construction of LCV2. TCG=tobacco chloroplast genome.

LCV2 consists of a 2253 bp lettuce chloroplast genome sequence (FIG. 5) spanning from the 16S rRNA/trnI intergenic region to the trnA/23S rRNA intergenic region, cloned into the PCR2.1 (Invitrogen) backbone vector (FIG. 6). This sequence corresponds to nucleotide positions 104366-106260 in the tobacco chloroplast genome (GI accession number Z00044). An alignment of this lettuce sequence with the tobacco chloroplast genome sequence is given in FIG. 7. The following description of the construction of LCV2 is outlined in FIG. 8.

Four primers LCV2A, LCV2B, LCV2C and LCV2D were used to amplify this region in two halves (LCV2A-B and LCV2C-D) and to introduce unique Pac1/Asc1 restriction sites in the intergenic region between the trnI and trnA genes at the position corresponding to nucleotide 105370 in the tobacco chloroplast genome.

For the first half (A-B) of the vector, DNA from clone 6 of the Sac1 library of the lettuce chloroplast genome (Jansen and Palmer, Current Genetics 11: 553-564 (1987)) was used as a template. Primers LCV2A and LCV2B amplified a 1258 bp fragment (1242 bp lettuce sequence+16 bp extension) (LCV2A-B) spanning from 16SrRNA/trnI intergenic region to the trnI/trnA intergenic region. This fragment was cloned into the *E. coli* plasmid cloning vector PCR2.1 (Invitrogen) to create PCR2.1 LCV2A-B. Primer LCV2B contains Pac1/Asc1 sites so that the LCV2A-B fragment has Pac1/Asc1 sites at the 3'end. PCR2.1 LCV2 A-B clones were screened for orientation by digestion with Kpn1/Asc1, which releases a fragment of approximately 1300 bp, and Xba1/Asc1 which linearised clones with the correct orientation for subsequent cloning.

For the second half of the vector chloroplast DNA from lettuce cultivar Evola (Leen de Moss seeds) was used as a template because the entire trnA gene was not contained in a single clone in the lettuce chloroplast genome library. Primers LCV2C and LCV2D amplified a 1011 bp fragment (995 bp lettuce sequence+16 bp extension) LCV2C-D. This sequence spans from the trnI/trnA intergenic region to the trnA/23S rRNA intergenic region. Primer LCV2C contains Pac1/Asc1 sites so the fragment LCV2C-D has Pac1/Asc1 sites at its 5' end. This fragment was cloned into PCR2.1 to create PCR2.1 LCV2 C-D. These clones were screened for orientation using Kpn1+Asc1, which linearises clones with required orientation and Xba1+Asc1, which releases a fragment of approximately 1000 bp in clones with the required orientation. To generate LCV2, the 1.3 kb Asc1+Xba1 insert from PCR2.1 LCV2C-D was subcloned into PCR2.1 LCV2A-B linearised with Asc1+Xba1.

3. Construction of LCV1-MSK18 and LCV2-MSK18

Figure 9:
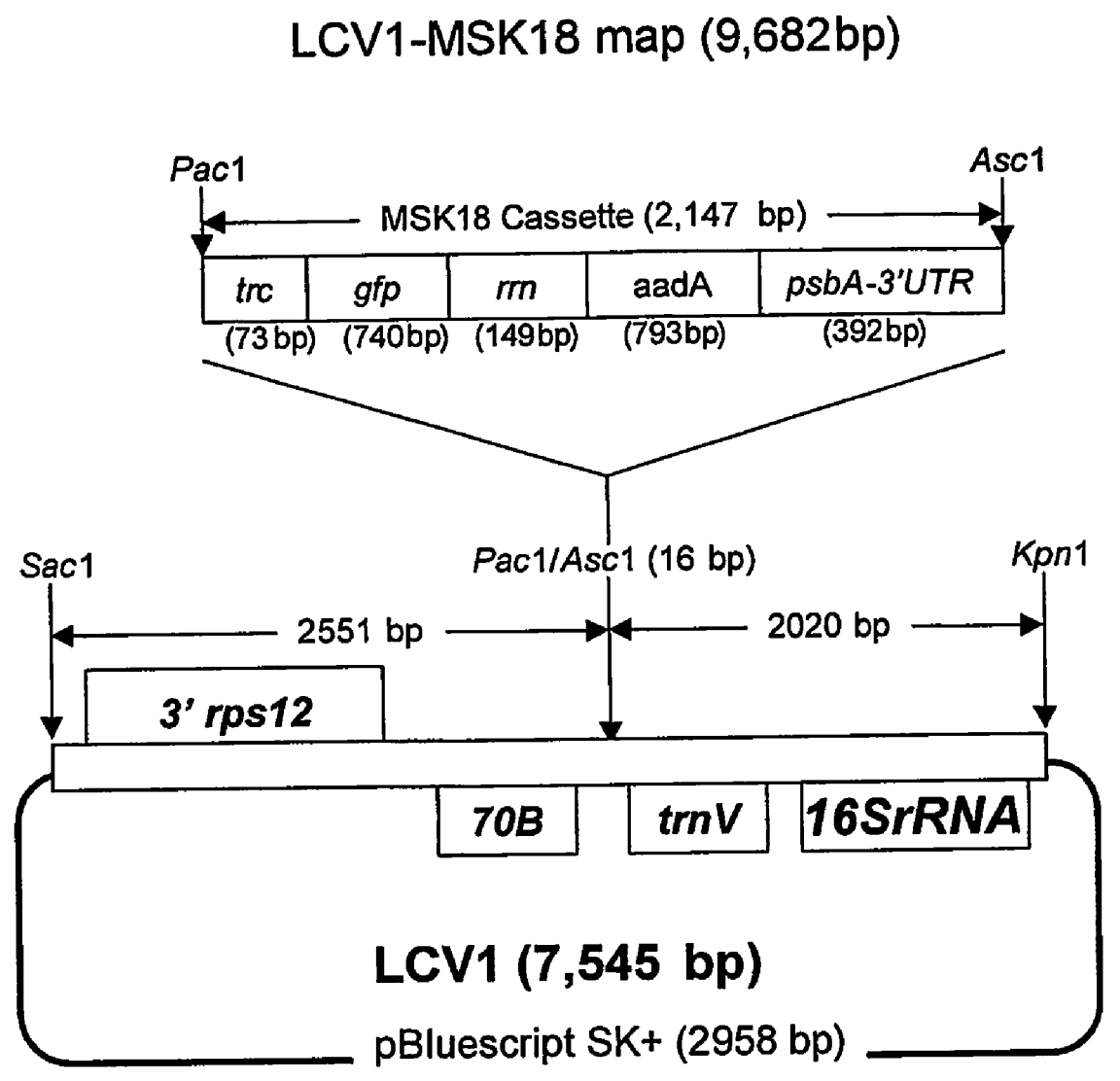

MSK18 is an expression cassette adapted from pMSK18 (Hibberd et al., The Plant Journal 16, 627-632 (1998)). Plasmid MSK18 was a gift from John Gray (Dept. Plant Sciences, University of Cambridge, Downing Street, Cambridge CB2 3EA, UK). Full details of the construction of pMSK18 have been described previously (Hibberd et al. 1998, supra). The MSK18 expression cassette consists of the mGFP coding region (Haseloff et al., Trends in Genetics 11, 328-329 (1997)) fused to a bacterial trc promoter (Amman and Brosius, Gene 40, 183-190 (1985)), and an aadA coding region, derived from pUC-atpX-AAD (Goldschmidt-Clermont, Nucleic Acids Research 19, 4083-4089 (1991)) fused to a tobacco rrn promoter derived from pZS197 (Svab and Maliga, Proc. Natl. Acad. Sci USA 90, 913-917 (1993)). A tobacco psbA 3' UTR derived from pSZ197 (Svab and Maliga, 1993 supra) is fused to the 3' end of the aadA gene (FIG. 9).

Figure 10:
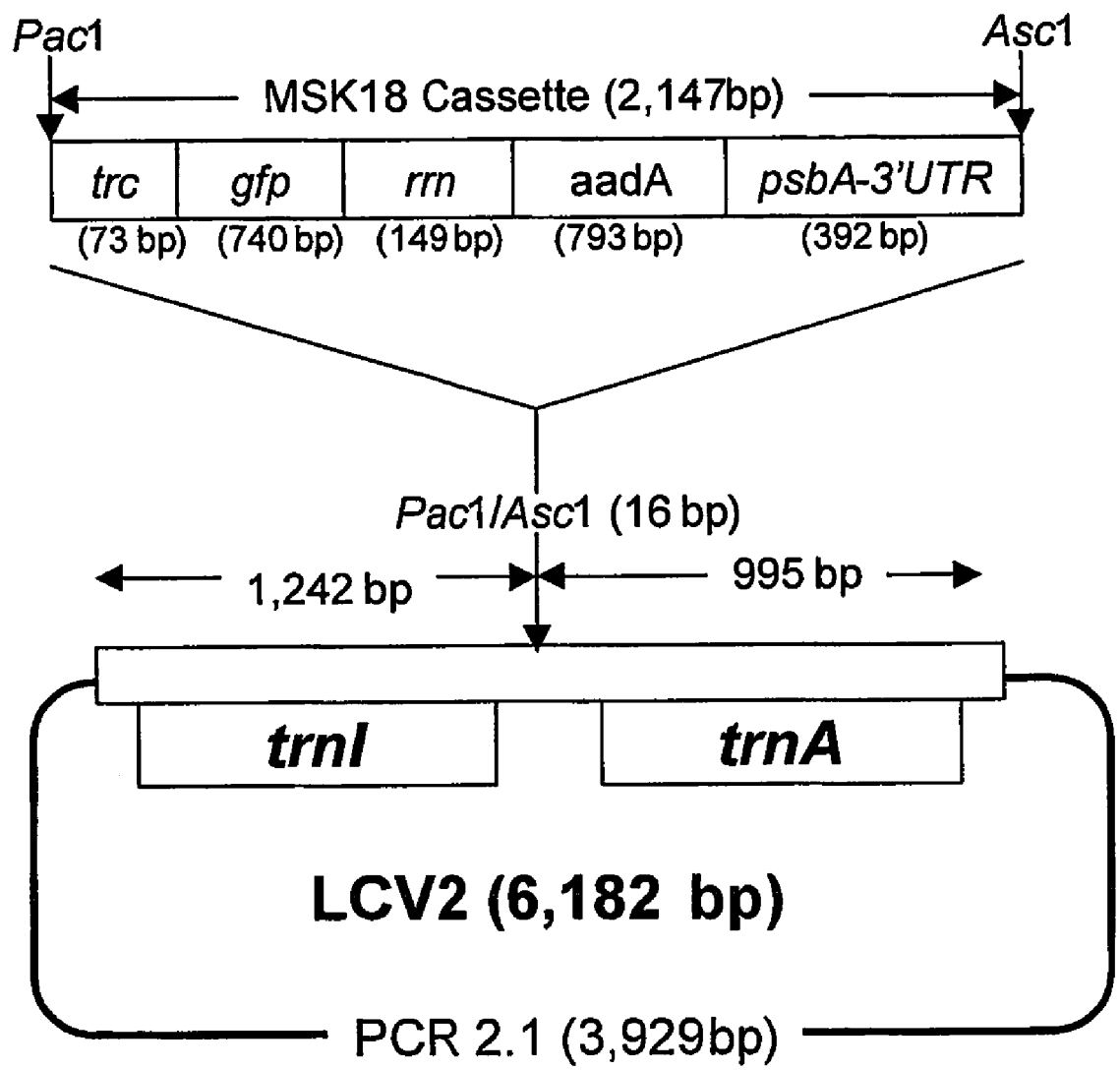
FIG. 10. Map of LCV2-MSK18 (8,329 bp).

Using pMSK18 as a template, Pac1 and Asc1 sites were added by PCR amplifying the cassette with primers containing Pac1 (5') and Asc1 (3') restriction sites to 5' and 3' ends of the of the MSK18 expression cassette. The primers used for this were MSK18 A (Forward) 5'-tag ttaattaaTTGACAATTAATCATCCGGCTCGT-3' (SEQ ID NO:31) and MSK18 B (Reverse) 5'-tag ggcgcgccTCGAATATAGCTCTTCTTTCTTA-3' (SEQ ID NO:32). The MSK18 A-B PCR product was cloned into PCR2.1 to create PCR2.1 MSK18. PCR2.1 MSK18 was restricted with PacI/AscI to release the MSK18 insert that was cloned into the PacI/AscI sites in LCV1 and LCV2 to create LCV1-MSK18 (FIG. 9) and LCV2-MSK18 (FIG. 10).

Example 2

Construction of LCV2-LEC1

Lettuce expression cassette 1 (LEC1; FIG. 21) contains the aadA gene, which confers spectinomycin and streptomycin resistance in plants, and the influenza virus haemagglutinin gene (HA) that codes for a potential influenza sub-unit vaccine. Both genes are under the control of a single lettuce specific promoter (Prrn) and terminator sequence (3' psbA). A chloroplast ribosome-binding site also precedes both genes. The expression cassette was assembled in three pieces using a combination of PCR amplification and overlap extension (FIG. 22).

The lettuce chloroplast specific ribosomal RNA operon promoter (Prrn) was amplified from lettuce chloroplast DNA (SacI fragment 6 from the Jansen cpDNA library; Jansen and Palmer, (Current Genetics 11: 553-564 (1987)) using PCR primers A and B. The aadA gene and upstream ribosome-binding site (rbs) was amplified from the tobacco chloroplast transformation vector pZS197 using PCR primers C and D. The HA gene and upstream rbs was amplified from an in-house HA gene construct (HA con3) using PCR primers E and F. A lettuce specific psbA termination sequence (3'psbA) was amplified from lettuce chloroplast DNA (cv. Evola) using PCR primers G and H. PCR products A+B and C+D were fused by overlap extension using PCR primers A and D.

The resulting PCR product A+D was cloned into the Sac1/NotI sites of pBS SK+ to create pBS A+D. PCR product E+F was cloned into the NotI/BamHI sites of pBS SK+ to create pBS E+F. PCR product G+H was cloned into the BamHI/PstI sites of pBS E+F to create pBS E+H. The complete insert (E+H) was excised by restriction with NotI/PstI and cloned into the NotI/PstI sites on pBS A+D to create pBS SK+ LEC1.

Expression of aadA and HA in pBS SK+ LEC1 was tested in *E.coli*. Transformed *E.coli* cells were resistant to streptomycin indicating that the aadA gene was expressed. Western analysis of HA expression with anti-HA sera showed expression of HA in *E.coli*. The entire expression cassette (Prrn/aadA/HA/psbA) was excised from pBS SK+ LEC1 using the restriction enzymes PacI and AscI and cloned into the PacI/AscI sites on the lettuce chloroplast transformation vector LCV2 to create LCV2-LEC1.

Example 3

Obtaining Seedlings and an in vitro Stock of Plants

Protoplasts of plants are isolated from leaf material of donor plants. In this example the obtaining of leaf shoot cultures is given.

Seeds are sterilized by subsequent washing in 70% ethanol, 0.7% NaOCl solution during 20 minutes and three times washing with sterile demineralized water. Seeds are sown on Murashige and Skoog (Murashige and Skoog, Physiol. Plant., 15: 473-497 (1962)) medium with saccharose 2%, without hormones. Preferably, seeds can be cultured at 15° C. for 2 days in the dark, after which the seeds are transferred to 25° C. in the light (approximately 3000 lux, photo period 16 hr light/8 hr dark TL FTD 840). When first true leaves appear, shoot tips are transferred to Murashige and Skoog based medium with 3% saccharose, without hormones. These sterile shoot cultures are grown under similar growth conditions.

Example 4

Isolation of Protoplasts

Three week old shoot cultures are used for isolation of protoplasts. Leaves are cut into small pieces and preplasmolysed during 1 hr in the dark in PG solution (54.66 g/l sorbitol and 7.35 g/l $CaCL_2.2H_2O$). The PG solution is then replaced by an enzyme solution with 1% cellulase and 0.25% macerozym. Incubation takes place during 16 hrs in the dark at 25° C.

Subsequently, the suspension is filtered through a nylon mesh filter (41 μm) en washed with a third of a volume of CPW16S solution (Frearson et al., Developmental Biology 33:130-137 (1973)) by centrifugation at 700 rpm during 8 minutes. In this way, intact protoplasts are collected on the surface of the supernatant. Protoplasts are washed in W5 solution (9 g/l NaCl, 18.38 g/l $CaCl_2.2H_2O$, 0.37 g/l KCl, 0.99 g/l glucose, 0.1 g/l Morpholinoethanesulfonide buffer (MES)) by centrifugation at 600 rpm during 5 minutes. With the procedure described, a protoplast yield of approximately 10-15×$10^6$ protoplasts per gram leaf material can be obtained.

Example 5

Selection of Protoplast Derived Calli on Spectinomycin Resistance

Protoplasts of lettuce, derived as described in example 4, are diluted in culture medium ½ B5 (Gamborg et al. Exp. Cell Res. 50:151 (1968)): 375 mg/l $CaCl_2.2H_2O$, 18.35 mg/l NaFeEDTA, 270 mg/l sodium succinate, 103 g/l saccharose, 0.1 mg/l 2,4 dichlorophenoxyacetic acid (2,4-D), 0.3 mg/l 6-benzylaminopurin (BAP) and 0.1 g/l MES and set to a culture density of 6×$10^4$ protoplasts per ml.

The protoplast suspension is mixed 1:1 with ½ B5 culture medium with agarose. The agarose beads are plated in larger petri dishes with liquid ½ B5 culture medium on top of it.

The petri dishes are taped with parafilm and cultured at 25° C. in the dark. One week after initiation of culture the culture medium is diluted with fresh liquid ½ B5 culture medium and 0.1 g/l MES. The cultures are transferred to the light (approx. 3000 lux, photo period 16 hours light/8 hours dark, TL FTD 840).

When calli are about 0.5 mm in size they are transferred to callus growth medium SH2 (Schenk & Hildebrandt, Can. J. Bot. 50:199-204 (1972)) with 30 g/l saccharose, 5 g/l agarose, 0.1 mg/l 1-naphtalene acetic acid (NAA) and 0.1 mg/l benzylaminopurin (BAP), and the selecting agent spectinomycin dihydrochloride at concentrations of 0-1000 mg/l. It was found that the optimal concentration of selection is 500 mg/l. The non-resistant calli appear as white calli. They also grow slower as compared to the control calli. The culture conditions are as described above for the above protoplast calli.

Example 6

Transformation of Protoplasts with Polyethylene Glycol and Selection for aadA Encoded Antibiotic Resistance Protoplasts of lettuce, derived as described in example 4, are set to a density of approximately 1-1.5×$10^6$ protoplasts/0.4-0.6 ml in transformation buffer (0.4 M mannitol, 15 mM $MgCl_2$, 1% (w/v) MES, pH 5.8). Subsequently, 10 μl of plasmid suspension (1 μg DNA/ill sterile $H_2O$) is added to the protoplasts as well as 0.4-0.6 ml PEG solution (40% w/v PEG 6000, 2.36 g/l Ca(NO$_3$)$_2$.4H$_2$O and 7.28 g/100 ml mannitol). Incubation is performed at room temperature for 5-30 minutes. Protoplasts are washed and resuspended in culture medium ½ B5 (Gamborg et al., Exp. Cell Res. 50:151 (1968)): 375 mg/l CaCl$_2$.2H$_2$O, 18.35 mg/l NaFeEDTA, 270 mg/l sodium succinate, 103 g/l saccharose, 0.1 mg/l 2,4 dichlorophenoxyacetic acid (2,4-D) and 0.3 mg/l 6-benzyl aminopurin (BAP).

The protoplast suspension is mixed 1:1 with ½ B5 culture medium with agarose. The agarose beads are plated in larger petri dishes with liquid ½ B5 culture medium on top of it.

The petri dishes are taped with parafilm and cultured at 25° C. After 6 days selection of the microcalli is performed by adding 500 mg/l of the selective agent spectinomycin dihydrochloride (final concentration). One week after initiation of culture the culture medium is diluted with fresh liquid ½ B5 culture medium, with addition of spectinomycin dihydrochloride and cultured in the light (approx. 3000 lux, photo period 16 hours light/8 hours dark, TL FTD 840).

When calli are about 0.5 mm in size they are transferred to callus growth medium SH2 (Schenk & Hildebrandt, 1972, supra) with 30 g/l saccharose, 5 g/l agarose, 0.1 mg/l 1-naphtalene acetic acid (NAA) and 0.1 mg/l benzylaminopurin (BAP), and the selecting agent spectinomycin dihydrochloride at concentrations described above. Culture conditions are as described above.

After 2 weeks calli are transferred to regeneration medium SHreg (Schenk and Hildebrandt, 1972, supra) with 15 g/l saccharose, 15 g/l maltose, 0.1 mg/l NAA and 0.1 mg/l BAP and spectinomycin dihydrochloride in concentrations described above. Spectinomycin resistant calli appear as green calli amongst white (non-resistant) calli.

Regenerating plants appear after approximately 6 weeks and furtheron, and are transferred to rooting medium (Schenk and Hildebrandt, supra) with 30 g/l saccharose and 8 g/l agar with the concentrations of spectinomycin dihydrochloride mentioned above. Alternatively, in transformation vectors where gfp (green fluorescent protein) is added as the gene of interest, gfp fluorescence is detected using an inverted microscope with the proper filter combinations. Green calli were detected 4-5 weeks after initiation of each experiment.

Table 1 gives an overview of the results obtained in protoplast transformation experiments with three different plasmids. Spectinomycin resistant calli were obtained after transformation of protoplasts with the plasmids PLCV2-MSK18 and PLCV2-LECI. Approximately 40-50% of the protoplasts did survive the PEG treatment. Callus lines of each individual event are maintained on medium SHreg with the selective agent spectinomycin dihydrochloride and yielded regenerated plants from plasmids pLCV2-MSK18 and pLCV2-LEC1 (Table 1). Also, ploidy differences were observed between individual calli.

TABLE 1

Selection of plastid transformants

| Treatment/Experiment | # pps treated | # green calli | # regenerating calli |
|---|---|---|---|
| control | none | 0 | |
| control + PEG | $1.26 \times 10^6$ | 0 | |
| pLCV1-MSK18 | $1.26 \times 10^6$ | 0 | |
| pLCV2-MSK18/exp 1 | $1.26 \times 10^6$ | 1 | 0 |
| pLCV2-MSK18/exp 2 | $2.40 \times 10^6$ | 1 | 0 |
| pLCV2-MSK18/exp 3 | $4.80 \times 10^6$ | 5 | 2 (1++, 1+/−) |
| pLCV2-LEC1/exp 1 | $3.60 \times 10^6$ | 5 | 3 (1++, 2+/−) |

The transgenic callus has been obtained using vectors with specific lettuce chloroplast DNA homologous sequences. Selection of transformed cells with the non-lethal selective agent spectinomycin has been successful. The optimal transformation frequency for lettuce, determined as the number of green calli to the number of surviving protoplasts is about 1 in 3-6. $10^5$ protoplasts (Table 1).

Figure 11:
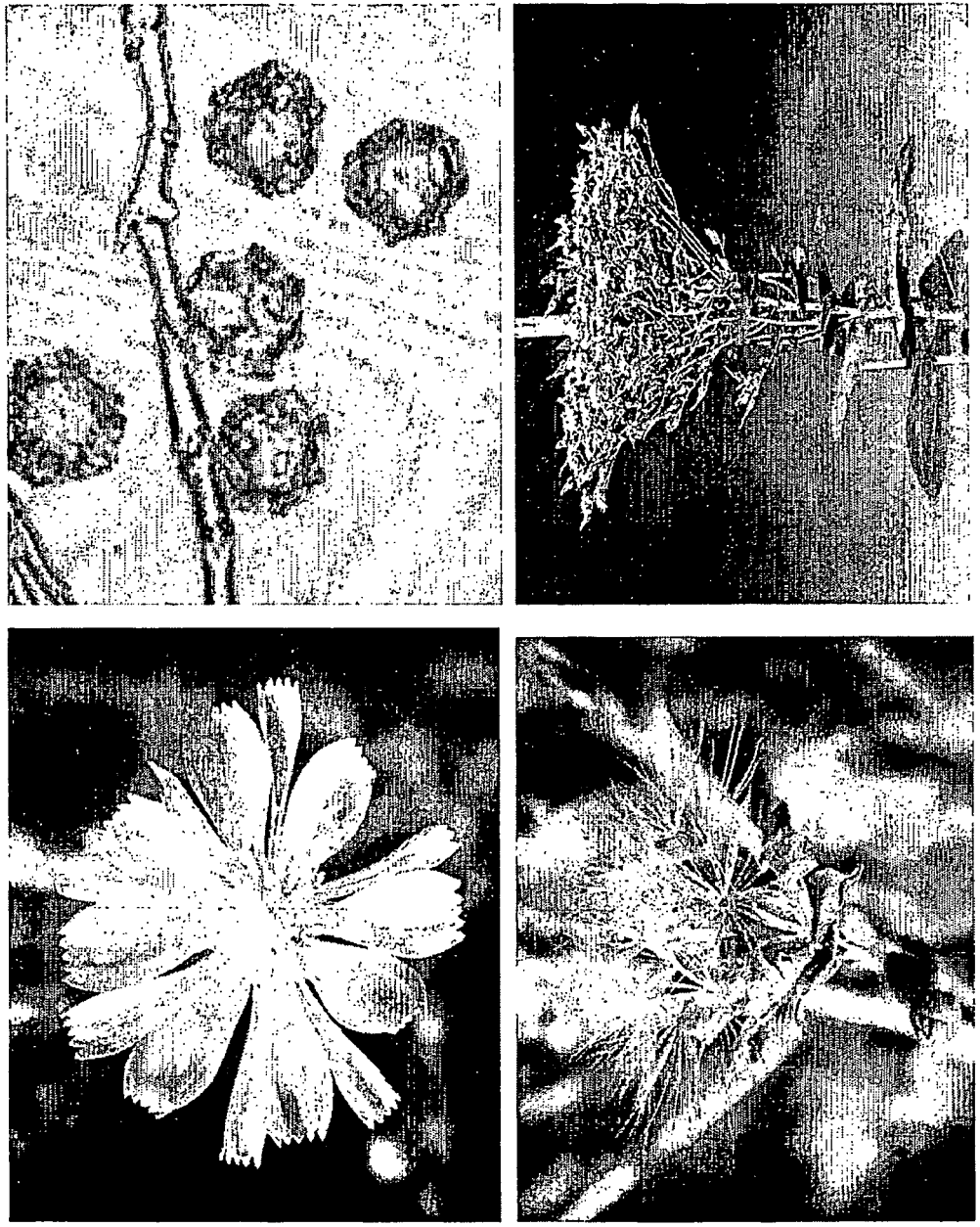
FIG. 11. Diploid Transplastomic lettuce pLCV2-LEC1 plants at stages of flowering (left upper panel), microspores (right upper panel) and seed set (right upper and lower panel)

The plants obtained from transformation experiments with pLCV2-LEC1 were found to have a normal, diploid ploidy level and showed a normal growth. Seed-set after selfing was obtained from these plants (FIG. 11).

Example 7

Transformation of Protoplasts via Electroporation and Selection on aadA Encoded Antibiotic Resistance Protoplasts, derived as described in example 4, are suspended in transformation buffer HBS (150 mM KCl, 4 mM CaCl$_2$.2H$_2$O, 10 mM HEPES (pH 7.2)), and enough mannitol to osmotically balance the protoplasts. This is dependent on the genotype but it can easily be found out experimentally. Aliquots of $1 \times 10^6$ protoplasts/0.5 ml HBS buffer and mannitol are put into a conical centrifuge tube, and plasmid DNA solution is added. Plasmid DNA concentrations in the transformation buffer should preferably be in the range of 10-100 μg/ml. The protoplast-DNA suspension is transferred to the electroporation chamber and electroporated using a single electric pulse (e.g. 325 μF, 300 V) The optimal setting can vary with species and cell type, and should be determined in preliminary experiments. The most efficient parameters are set by finding the pulse settings that result in 50% protoplast death by 24 h after the shocks. More details of the method are described by G. W. Bates (Plant transformation via protoplast electroporation. From: Methods in Molecular Biology Vol 111: Plant cell Culture Protocols, Pp 359-366 (1999)).

After electroporation, protoplasts culture and selection is performed as described in example 6.

Example 8

Adjustment of Spectinomycin Threshold Levels in Cotyledons

For the adjustment of the optimal concentration of spectinomycin, for selection of cells with chloroplasts/plastids, which are transformed with constructs having the aadA gene as selectable marker, 4-10 day old cotyledons were plated with the abaxial side onto MS medium (Murashige and Skoog, supra) with 0.8% agar, 30 g/l saccharose, 100-200 mg/l carbenicillin, 0.1 mg/l benzylaminopurin (BAP), 0.1 mg/l 1-naphtalene acetic acid (1-NAA) at pH 5.8, and with various concentrations of spectinomycin dihydrochloride. The cotyledons were obtained as described in Example 3, and cultured at 25° C. in the light (approx. 3000 lux, photo period 16 hours light/8 hours dark, TL FTD 840). It was found that a concentration of 0.5-1 g/l spectinomycin dihydrochloride was sufficient for efficient selection, leading to complete bleaching and loss of growth and regeneration of control cotyledons.

Example 9

Transformation of Plant Material via Biolistics and Selection for aadA Encoded Antibiotic Resistance For bombardment of cotyledons, seeds were sown as described in example 3. Alternatively, leaf pieces can be used as explant material for shooting, under similar conditions. Cotyledons (3 to 12 days old) or leaf pieces from 10-14 days old seedlings are placed with the abaxial side onto MS medium (Murashige and Skoog, supra) with 0.8% agar, 0.3 mg/l BAP and 0.1 mg/l 2,4-D (pH 5.8) and preincubated for 1-6 days before transformation with a particle gun.

The cotyledons are cultured at 25° C. in the light (approx. 3000 lux, photo period 16 hours light/8 hours dark, TL FTD 840).

Gold particles (0.6 to 1.6 µm) were prepared for transformation by mixing 50 µl of suspension (60 mg/ml 50% glycerol) with 5 µg DNA (1 µg/µl $H_2O$), 50 µl $CaCl_2$ (2.5 M) and 20 µl spermidine (0.1 M base). The particle-DNA mixture was incubated at room temperature for 1-3 minutes and centrifuged for 3-10 sec. in an Eppendorf centrifuge. After removal of the supernatant, the coated particles are washed and diluted in 48-60 µl ethanol. The particles (6-8 µl per carrier) are applied to the macrocarrier holders and the bombardment is performed with PDS-1000/He Biolistic particle delivery system (BioRad).

The explants are placed at approximately 6 cm target distance and bombarded using a 1100 p.s.i rupture disc. Details of the procedure has been described by Klein et al. (Bio/Technology 6: 559-563 (1988)).

Two to fourteen days after bombardment, the cotyledons are transferred to MS1 liquid medium (Murashige and Skoog, supra) with 30 g/l saccharose and supplemented with 100-200 mg/l carbenicillin, 0.1 mg/l benzylaminopurin (BAP) and 0.1 mg/l 1-naphtalene acetic acid (1-NAA) at pH 5.8 as described above with the addition of a selective agent (e.g. spectinomycin dihydrochloride at concentration of 500 mg/l). They are incubated in liquid medium at 25° C. in the light (approx. 3000 lux, photo period 16 hours light/8 hours dark, TL FTD 840) for about 1-8 days, after which they are transferred to solid MS1 medium (see above with the addition of 8 g/l agar). Cultures are transferred onto fresh medium every 2 weeks.

When green callus or shoots appear, they are transferred to medium MS1 without carbenicillin, but including the selective agent spectinomycin dihydrochloride.

Table 2 presents results from transformation experiments with pLCV2-MSK18. It was found that green, spectinomycin resistant callus was formed on bombarded cotyledons, approximately 2.5 months after initiation of the experiment. The spectinomycin resistant callus was maintained on MS1 medium with the selective agent.

TABLE 2

Results of particle bombardment experiments with pLCV2-MSK18 using cotyledons or leaf pieces.

| Explant type/treatment | Number of bombarded explants | Number of explants with spectinomycin resistant callus |
|---|---|---|
| Cotyledon, bombarded selection | 180 | 1 |
| Cotyledon control selection | 30 | 0 |
| Leaf bombarded selection | 96 | 0 |
| Leaf control selection | 16 | 0 |

Example 10

Molecular Analysis of Spectinomycin Resistant Calli of Lettuce

Spectinomycin resistance of plant cells may be the result, apart from transformation with the vector LCV2-MSK18, of spontaneous mutation of chloroplast DNA or insertion of the DNA into the nuclear genome. Therefore, the callus and regenerated plants were screened for the integration of the right and left homologous border segment as is described in this Example. Additionally, it was determined whether the aadA gene, the gfp and HA gene were correctly integrated in the chloroplast DNA.

1. Analysis of Calli Derived from PEG Protoplast Transformations with pLCV2-MSK18

Spectinomycin resistant callus of lettuce was analysed by PCR using different primer combinations to confirm the integration of the plasmid pLCV2-MSK18 in the genome of the chloroplast.

As an endogenous control for chloroplast DNA amplification, PCR analysis of the ATPase gene (Accession: AF162208) was carried out using the forward primer 5'-ACTAATAGTGGACAAATTGGC-31 (SEQ ID NO:33) and the reverse primer 5'-TTGCTTGATTGTATTTACTCG-3' (SEQ ID NO:34). To detect the presence of the selectable marker gene AadA, the following primer combination was used: forward 5'-AAGTCACCATTGTTGTGCACG-3' (SEQ ID NO:35) and reverse 5'-TATGACGGGCTGATACTGGGC-3' (SEQ ID NO:36). In order to demonstrate the physical integration of the plasmid into the chloroplast genome 2 primer combinations were developed which amplify hybrid regions of the plasmid and the chloroplast genome (see FIG. 12). The first primer combination consisting of P1 and P2 amplifies the junction containing the trnI sequence of the chloroplast genome (left border integration). The second primer combination consisting of P3 and P4 amplifies the junction containing the trnA sequence of the chloroplast genome (right border integration).

Total DNA was isolated from spectinomycin resistant callus using a commercially available DNA isolation kit from Sigma (Genelute Plant Genome DNA Kit). The PCR reaction was carried out using a total amount of 30 ng DNA after which the reaction products were analysed on a 1% agarose gel.

Figure 13:
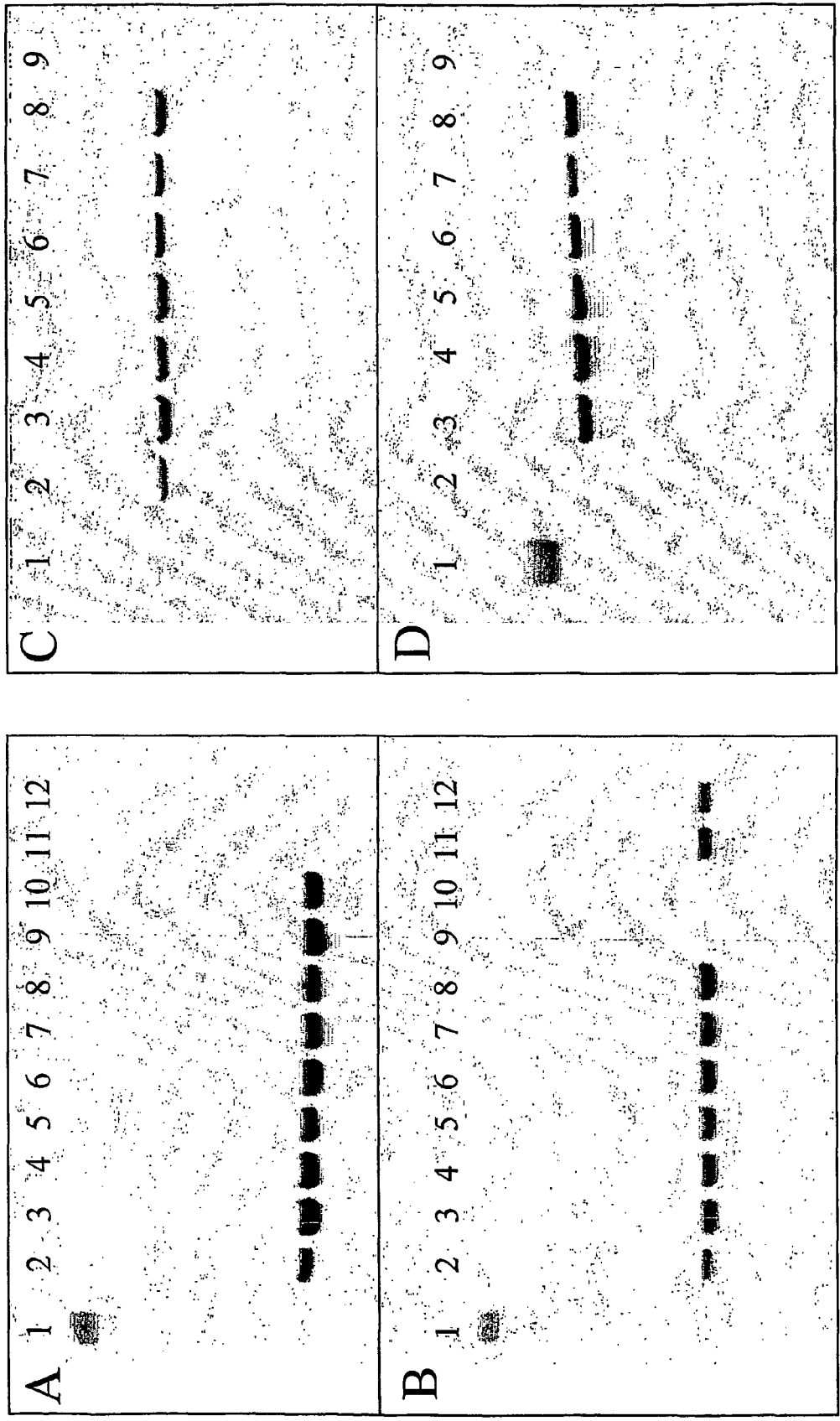
FIG. 13. Molecular analysis of spectinomycin resistant lettuce calli.

The result of the analysis of 5 independent spectinomycin resistant calli derived from PEG protoplast transformations is shown in FIG. 13 (data of 2 calli not shown but identical to the other 5). The ATPase fragment of about 424 bp is only present in callus material and leaf material of lettuce, and as expected not visible for the pLCV MSK18 DNA (FIG. 13A). PCR amplification of the aadA gene gave the expected fragment of approximately 413 bp for the transgenic callus and the plasmid pLCV2-MSK18 (FIG. 13B).

To confirm the integration of the pLCV2-MSK18 vector into the lettuce chloroplast genome, the two primer combinations were used which specifically detect either one of the two junctions which emerge after integration of the plasmid by homologous recombination. The integration on trnI junction was investigated using the PCR primers indicated above, which resulted in an expected band of approximately 2000 bp as well (FIG. 13C). FIG. 13D shows the amplification of the trnA junction which results in an expected band of approx. 1500 bp in the spectinomycin resistant callus. The results of this analysis confirm the transplastomic nature of the obtained spectinomycin resistant pLCV2-MSK18 lettuce calli, and no escapes were found.

For further confirmation of integration, the left and right integration junctions were amplified by PCR using primer pairs P1+P2 and P3+P4. The PCR products from one spectinomycin resistant callus sample were cloned into PCR2.1 and sequenced using M13 forward and M13 reverse primers. These sequences confirmed that LCV2-MSK18 was integrated in the lettuce chloroplast genome (FIG. 14).

Figure 12:
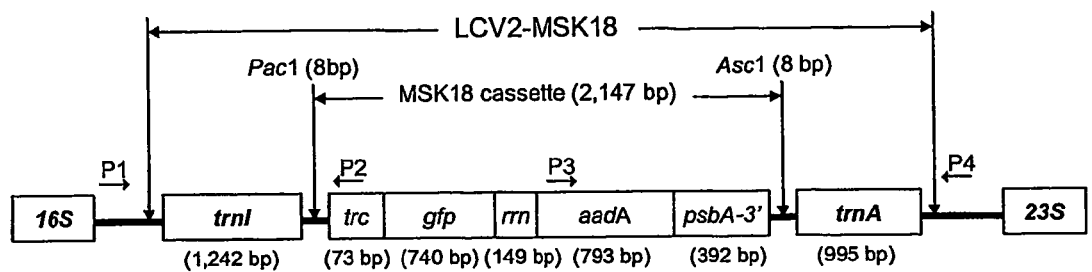
FIG. 12. Primer combinations (SEQ ID NOS:17-20) used in PCR analysis of transplastomic lettuce callus.

To eliminate the possibility of amplification of unintegrated LCV2-MSK18 plasmid DNA, primers P1 and P4 were designed from lettuce chloroplast sequences external to the vector target region (FIG. 12). PCR analysis was carried out on DNA isolated from 6 putatively transformed calli. In all cases, P1 and P4 give two PCR products, a 2476 bp band corresponding to the expected size of a product amplified from an untransformed wild-type chloroplast genome, and a 4623 bp band corresponding to the size of a PCR product expected from a transformed chloroplast genome. FIG. 15 shows the results in detail for one callus, and FIG. 16 shows the PCR results on insert integration for 6 independent calli.

2. Molecular Analysis of Spectinomycin Resistant Callus, Derived After Biolistic Transformation with pLCV2-MSK18

Similar primer combinations, as used for the spectinomycin resistant callus out of PEG protoplast experiments were used to evaluate the transplastomic nature of the callus derived from bombarded tissue. FIG. 17 shows the products of the trnI and trnA junction, respectively. It was verified that the callus was of a transplastomic nature.

3. Molecular Analysis of Putative Transplastomic Callus, Derived from PEG Protoplast Transformation Experiments with pLCV2-LEC1.

For the analysis of the calli, obtained by protoplast transformation experiments with pLCV2-LEC1, similar primer combinations as for the pLCV2-MSK18 plasmid transformations could be used for the aadA gene, the endogenous control and the insert integration P1+P4 (See FIG. 13). Furthermore, PCR analysis on left border integration was performed by using the forward primer 5'-ACTGGAAGGTGCGGCTG-GAT-3' (SEQ ID NO:37) and the reverse primer 5'TAT-GACGGGCTGATACTGGGC-3' (SEQ ID NO:38). Right border integration was performed by using the forward primer 5'-ATGCAAAAACTTCCCGGAAAT-3' (SEQ ID NO:39) and reverse primer 5'-CTCGCCCTTAATTT-TAAGGC-3' (SEQ ID NO:40).

Results of these analyses are shown in FIG. 18. It is clear that all 5 independent calli are true transplastomic ones, and no escapes were found.

4. Molecular Analysis of Regenerated Plants from Transplastomic Callus, Derived from PEG Protoplast Transformation Experiments with pLCV2-MSK18 and LEC1

Figure 19:
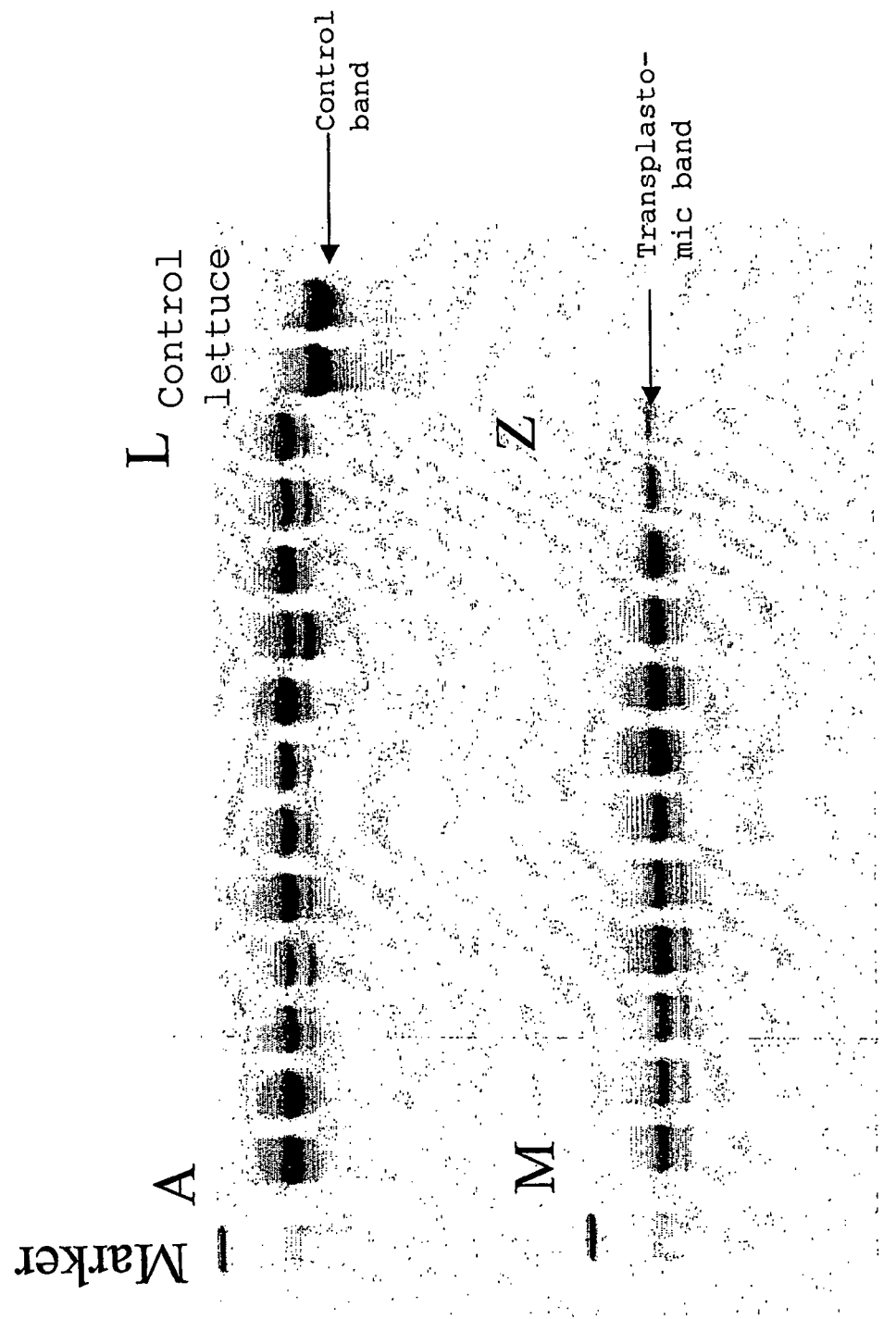

FIG. 19 shows the PCR results from DNA derived from several plants regenerated from one transplastomic pLCV2-MSK18 callus. FIG. 20 shows PCR analysis of pLCV2-LEC1 regenerated plants. It is clear that both types of plants are truly transplastomic.

The invention claimed is:

1. A method for the transformation of plastid genomes, comprising the steps of:
   a) providing a transformation vector carrying a DNA sequence of interest and a selection marker;
   b) subjecting a plant material derived from *Asteraceae*, which comprises plastids, to a transformation treatment in order to allow the plastids to receive the transformation vector;
   c) placing the thus treated plant material for a period of time into contact with a liquid culture medium without a selection agent;
   d) subsequently placing the plant material into contact with a liquid culture medium and adding a selection agent to the culture medium comprising the plant material, wherein the selection marker is a visual marker; and
   e) refreshing the liquid culture medium comprising a selection agent to allow plant material comprising plastids that have acquired the DNA of interest to grow into transformants.

2. A method for the transformation of plastid genomes of a plant species, comprising the steps of:
   a) providing a transformation vector carrying a DNA sequence of interest, and one or more selection markers;
   b) subjecting a plant material derived from *Asteraceae*, which comprises plastids, to a transformation treatment in order to allow the plastids to receive the transformation vector;
   c) placing the thus treated plant material for a period of time into contact with a culture medium without a selection agent;
   d) illuminating the treated and cultured plant material with an appropriate light source corresponding to the selection marker, wherein the selection marker is a visual marker; and
   e) selecting the plant material that shows the visual marker.

3. The method as claimed in claim 1, wherein the visual marker is a fluorescent marker.

4. The method as claimed in claim 3, wherein the fluorescent marker is green fluorescence protein.

* * * * *

UNITED STATES PATENT AND TRADEMARK OFFICE
CERTIFICATE OF CORRECTION

| | | |
|---|---|---|
| PATENT NO. | : 7,645,918 B2 | Page 1 of 1 |
| APPLICATION NO. | : 10/523918 | |
| DATED | : January 12, 2010 | |
| INVENTOR(S) | : Lelivelt et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 579 days.

Signed and Sealed this

Sixteenth Day of November, 2010

David J. Kappos
*Director of the United States Patent and Trademark Office*

SEQUENCE LISTING

<160> NUMBER OF SEQ ID NOS: 41

<210> SEQ ID NO 1
<211> LENGTH: 4587
<212> TYPE: DNA
<213> ORGANISM: Lactuca sativa

<400> SEQUENCE: 1

```
gttcaagaat cagttttctt tttataaggg ctaaaatcac ttattttggc ttttttaccc      60
catattgtag ggtggatctc gaaagatatg aaagatctcc ctccaagccg tacatacgac     120
tttcatcgaa tacggctttc cgcagaattc tatatgtatc tatgagatcg agtatggaat     180
tctgtttact cactttaaat tgagtatccg tttccctcct tttcctgcta ggattggaaa     240
tcctgtattt tacatatcca tacgattgag tccttgggtt tccgaaatag tgtaaaaaga     300
agtgcttcaa atcattgcta tttgactcgg acctgttcta aaaagtcgag gtatttcgaa     360
ttgtttgttg acacggacaa agtcagggaa aacctctgaa attttttcaa tattgaacct     420
tggacatata atagttccga atcgaatctc tttagaaaga agatcttttg tctcatggta     480
gcctgctcca gtcccttac gaaactttcg ttattgggtt agccatacac ttcacatgtt     540
tctagcgatt cacatggcat catcaaatga tacaagtctt ggataagaat ctacaacgca     600
ctagaacgcc cttgttgacg atcctttact ccgacagcat ctagggttcc tcgaacaatg     660
tgatatctca caccgggtaa atccttaacc ctcccccctc ttactaagac tacagaatgt     720
tcttgtgaat tatggccaat accgggtata taagcagtga tttcaaatcc agaggttaat     780
cgtactctgg caactttacg taaggcagag tttggttttt tggggtgat agtggaaaag     840 ttgacagata agtcacccctt actgccactc tacagaaccg tacatgagat tttcacctca     900
tacggctcct cgttcaattc tttcgaagtt attggatcct tttccgcgtt cgagaatccc     960
```

```
ctcccttctt ccactccgtc ccgaagagta actaggacca atttagtcac gttttcatgt    1020
tccaattgaa cactttccgt ttttgattat tctctttacc aaacatatgc ggatccaatc    1080
acgatcttat aataagaaca agagatcttt ctcgatcaat ccccttgccc ctcattcttc    1140
gagaatcaga aagatccttt tcaagtttga atttgttcat ttggaatctg agttcttcta    1200
cttcattatt tatttaatat caatattttt gcctctcttt tttttatatt attccttaag    1260
tcccataggt ttgatccttt agaattggac tcattttctc attgagcgaa gggtacgaaa    1320
taaatcagat tgattaaaag cactatgtga aatattcggt ttttcctct tcctctatcc     1380 cataggtaca gtgtttgaat caatcgagaa ccttttcttc tgtctgaatc gatattattc    1440
cattccaatt ccttcccgat acctctcaag gaaaatctcg aattggatcc taaattgacg    1500
ggttagtgtg agcttatcca tgcggttatg cactcttcga ataggaatcc attttctgaa    1560
agatcctggc tttcgtgctt tggtgggtct ccgagatcct ttcgatgacc tatgttgtgt    1620
ttgttgaagg gatatctata taatacgatc gattgcgtaa agcccgcggt agcagtggaa    1680
ccggggaaag tatacagaaa agacagttct tttctattat atattatatt agtcttttct    1740
atttaattca tattagatta gtcttagtta gtgatcccgg cttagtgagt cctttcttcc    1800
gtgatgaact gttggcgcca gtcctacatt ttgtctctgt ggacagagga gaaaaggggc    1860
tccgcgggaa gaggattgta ccgtgagaga agcaaggagg tcaacctctt tcaaatatac    1920
aacatggatt ctggcaatgc aatgtacttg gactctcatg tcgatccgaa tgaatcatcc    1980
tttccacgga ggcaaatctt tgcctgttag gtaacaggat agcaagttac aaactctgtc    2040
tcggtaggac atggatctct attactatga atttcataaa tgaagtagtg aatggtgggg    2100
ttaccattat ccttttttgta gtgacgaatc ctgtatgtgt tcctaagaaa aggaatttgt    2160
acatttttcg ggatctcaaa ggagcgtgga aacacataag aactcttgaa tggaaatgga    2220
aaagagatgg aactccagtt ccttcggaaa tggtaagatc tttggcgcaa aaaaggggt     2280 tgatccgtat catcttgact tggttctgct tcctctattt ttttaataat accgggtcgg    2340
gttcttctcc tacccgtatc gaatagaaca cgctgagcca aatcttcttc atgtaaaacc    2400
tgcttgattt agatcgggaa aatcgtgtgg ttttatgaaa ccatgtgcta tggctcgaat    2460
ccgtagtcaa tcctatttcc gatagggaca gttgacaact gaatcctatt ttcccattat    2520
tttcatatcc gtaatagtgc gaaaaaaaag attaattaag gcgcgccagg cccggcccca    2580
agttgttcaa gaatagtgtc gttgagtttc tcgacccttt gccttaggat taatcagttc    2640
tatttctcga tgggggcagg gaagggatat aactcaccgg tagagtgtca cccttgacgt    2700
ggtggaagtc atcagttcga gcctgattat ccctaaaccc aatgtgagtt ttgatatttt    2760
gatttgctac cccgccgtga ttgaatgaga atggataaga ggctcgtggg attgacgtga    2820
gggggcaggg atggctatat ttctgggagc gaactccggg cgaatatgaa gcgcatggat    2880
acaagttagg ccttggaatg aaagacaatt ccgaatccgc tttgtctacg aacaaggaag    2940
ctataagtaa tgcaactatg aatctcatgg agagttcgat cctggctcag gatgaacgct    3000
ggcggcatgc ttaacacatg caagtcggac gggaagtggt gtttccagtg gcggacgggt    3060
gagtaacgcg taagaacctg cccttgggag gggaacaaca gctggaaacg gctgctaata    3120
ccccgtaggc tgaggagcaa aaggaggaat ccgcccgagg aggggctcgc gtctgattag    3180
ctagttggtg aggtaatagc ttaccaaggc gatgatcagt agctggtccg agaggatgat    3240
cagccacact gggactgaga cacggcccag actcctacgg gaggcagcag tggggaattt    3300
tccgcaatgg gcgaaagcct gacggagcaa tgccgcgtgg aggtagaagg cccacgggtc    3360
```

-continued

```
atgaacttct tttcccggag aagaagcaat gacggtatct ggggaataag catcggctaa    3420
ctctgtgcca gcagccgcgg taatacagag gatgcaagcg ttatccggaa tgattgggcg    3480
taaagcgtct gtaggtggct ttttaagtcc gccgtcaaat cccagggctc aactctggac    3540
aggcggtgga aactaccaag ctggagtacg gtaggggcag agggaatttc cggtggagcg    3600
gtgaaatgcg tagagatcgg aaagaacacc aacggccaaa gcactctgct gggcccacac    3660
tgacactgag agacgaaagc taggggagcg aatgggatta gatacccag tagtcctagc     3720 cgtaaacgat ggatactagg cgctgtgcgt atcgacccgt gcagtgctgt agctaacgcg    3780
ttaagtatcc cgcctgggga gtacgttcgc aagaatgaaa ctcaaaggaa ttgacggggg    3840
cccgcacaag cggtggagca tgtggtttaa ttcgatgcaa agcgaagaac cttaccaggg    3900
cttgacatgc cgcgaatcct cttgaaagag agggtgcct tcgggaacgc ggacacaggt     3960
ggtgcatggc tgtcgtcagc tcgtgccgta aggtgttggg ttaagtcccg caacgagcgc    4020
aaccctcgtg tttagttgcc atcattgagt ttggaaccct gaacagactg ccggtgataa    4080
gccggaggaa ggtgaggatg acgtcaagtc atcatgcccc ttatgccctg ggcgacacac    4140
gtgctacaat ggccgggaca aagggtcgcg atcccgcgag ggtgagctaa ccccaaaaac    4200
ccgtcctcag ttcggattgc aggctgcaac tcgcctgcat gaagccggaa tcgctagtaa    4260
tcgccggtca gccatacggc ggtgaatccg ttcccgggcc ttgtacacac cgcccgtcac    4320
actatgggag ctggccatgc ccgaagtcgt taccttaacc gcaaggaggg ggatgccgaa    4380
ggcagggcta gtgactggag tgaagtcgta acaaggtagc cgtactggaa ggtgcggctg    4440
gatcacctcc ttttcaggga gagctaatgc ttgttgggta ttttggtttg acactgcttc    4500
acacccaaaa aagaagggag ctacgtctga gttaaacttg gagatggaag tcttcatttc    4560
gtttctcgac agtgaagtaa gaccaag                                        4587
```

<210> SEQ ID NO 2
<211> LENGTH: 4587
<212> TYPE: DNA
<213> ORGANISM: Lactuca sativa

<400> SEQUENCE: 2

```
gttcaagaat cagttttctt tttataaggg ctaaaatcac ttattttggc ttttttaccc      60
catattgtag ggtggatctc gaaagatatg aaagatctcc ctccaagccg tacatacgac     120
tttcatcgaa tacggctttc cgcagaattc tatatgtatc tatgagatcg agtatggaat     180
tctgtttact cactttaaat tgagtatccg tttcctcct tttcctgcta ggattggaaa      240
tcctgtattt tacatatcca tacgattgag tccttgggtt ccgaaatag tgtaaaagaa      300 agtgcttcaa atcattgcta tttgactcgg acctgttcta aaaagtcgag gtatttcgaa    360
ttgtttgttg acacggacaa agtcagggaa aacctctgaa attttttcaa tattgaacct    420
tggacatata atagttccga atcgaatctc tttagaaaga agatcttttg tctcatggta     480
gcctgctcca gtcccttac gaaactttcg ttattgggtt agccatacac ttcacatgtt     540
tctagcgatt cacatggcat catcaaatga tacaagtctt ggataagaat ctacaacgca    600
ctagaacgcc cttgttgacg atcctttact ccgacagcat ctagggttcc tcgaacaatg    660
tgatatctca caccgggtaa atccttaacc ctccccctc ttactaagac tacagaatgt     720
tcttgtgaat tatggccaat accgggtata taagcagtga tttcaaatcc agaggttaat    780
cgtactctgg caactttacg taaggcagag tttggttttt ttggggtgat agtggaaaag    840
```

```
ttgacagata agtcacccectt actgccactc tacagaaccg tacatgagat tttcacctca    900
tacggctcct cgttcaattc tttcgaagtt attggatcct tttccgcgtt cgagaatccc    960
ctcccttctt ccactccgtc ccgaagagta actaggacca atttagtcac gttttcatgt   1020
tccaattgaa cactttccgt ttttgattat tctctttacc aaacatatgc ggatccaatc   1080
acgatcttat aataagaaca agagatcttt ctcgatcaat ccccttgccc ctcattcttc   1140
gagaatcaga aagatccttt tcaagtttga atttgttcat ttggaatctg agttcttcta   1200
cttcattatt tatttaatat caatattttt gcctctcttt tttttatatt attccttaag   1260
tcccataggt ttgatccttt agaattggac tcatttctc attgagcgaa gggtacgaaa    1320
taaatcagat tgattaaaag cactatgtga aatattcggt ttttcctct cctctatcc     1380
cataggtaca gtgtttgaat caatcgagaa ccttttcttc tgtctgaatc gatattattc   1440
cattccaatt ccttcccgat acctctcaag gaaaatctcg aattggatcc taaattgacg   1500
ggttagtgtg agcttatcca tgcggttatg cactcttcga ataggaatcc attttctgaa   1560
agatcctggc tttcgtgctt tggtgggtct ccgagatcct ttcgatgacc tatgttgtgt   1620
ttgttgaagg gatatctata taatacgatc gattgcgtaa agcccgcggt agcagtggaa   1680
ccggggaaag tatacagaaa agacagttct tttctattat atattatatt agtcttttct   1740
atttaattca tattagatta gtcttagtta gtgatcccgg cttagtgagt cctttcttcc   1800
gtgatgaact gttggcgcca gtcctacatt ttgtctctgt ggacagagga gaaaaggggc   1860
tccgcgggaa gaggattgta ccgtgagaga agcaaggagg tcaacctctt tcaaatatac   1920
aacatggatt ctggcaatgc aatgtacttg gactctcatg tcgatccgaa tgaatcatcc   1980
tttccacgga ggcaaatctt tgcctgttag gtaacaggat agcaagttac aaactctgtc   2040
tcggtaggac atggatctct attactatga atttcataaa tgaagtagtg aatggtgggg   2100
ttaccattat ccttttttgta gtgacgaatc ctgtatgtgt tcctaagaaa aggaatttgt   2160
acattttcg ggatctcaaa ggagcgtgga aacacataag aactcttgaa tggaaatgga    2220
aaagagatgg aactccagtt ccttcggaaa tggtaagatc tttggcgcaa aaaaggggt    2280
tgatccgtat catcttgact tggttctgct tcctctattt ttttaataat accgggtcgg   2340
gttcttctcc tacccgtatc gaatagaaca cgctgagcca atcttcttc atgtaaaacc    2400
tgcttgattt agatcgggaa aatcgtgtgg ttttatgaaa ccatgtgcta tggctcgaat   2460
ccgtagtcaa tcctatttcc gatagggaca gttgacaact gaatcctatt ttcccattat   2520
tttcatatcc gtaatagtgc gaaaaaaaag attaattaag gcgcgccagg cccggcccca   2580
agttgttcaa gaatagtgtc gttgagtttc tcgacccttt gccttaggat taatcagttc   2640
tatttctcga tgggggcagg gaaggatat aactcaccgg tagagtgtca cccttgacgt    2700
ggtggaagtc atcagttcga gcctgattat ccctaaaccc aatgtgagtt ttgatatttt   2760
gatttgctac cccgccgtga ttgaatgaga atggataaga ggctcgtggg attgacgtga   2820
gggggcaggg atggctatat ttctgggagc gaactccggg cgaatatgaa gcgcatggat   2880
acaagttagg ccttggaatg aaagacaatt ccgaatccgc tttgtctacg aacaaggaag   2940
ctataagtaa tgcaactatg aatctcatgg agagttcgat cctggctcag gatgaacgct   3000
ggcggcatgc ttaacacatg caagtcggac gggaagtggg gtttccagtg gcggacgggt   3060
gagtaacgcg taagaacctg cccttgggag gggaacaaca gctggaaacg gctgctaata   3120
ccccgtaggc tgaggagcaa aaggaggaat ccgcccgagg aggggctcgc gtctgattag   3180
ctagttggtg aggtaatagc ttaccaaggc gatgatcagt agctggtccg agaggatgat   3240
```

```
cagccacact gggactgaga cacggcccag actcctacgg gaggcagcag tggggaattt    3300
tccgcaatgg gcgaaagcct gacggagcaa tgccgcgtgg aggtagaagg cccacgggtc    3360
atgaacttct tttcccggag aagaagcaat gacggtatct ggggaataag catcggctaa    3420
ctctgtgcca gcagccgcgg taatacagag gatgcaagcg ttatccggaa tgattgggcg    3480
taaagcgtct gtaggtggct ttttaagtcc gccgtcaaat cccagggctc aactctggac    3540
aggcggtgga aactaccaag ctggagtacg gtaggggcag agggaatttc cggtggagcg    3600
gtgaaatgcg tagagatcgg aaagaacacc aacggccaaa gcactctgct gggcccacac    3660
tgacactgag agacgaaagc taggggagcg aatgggatta gatccccag tagtcctagc     3720 cgtaaacgat ggatactagg cgctgtgcgt atcgacccgt gcagtgctgt agctaacgcg    3780
ttaagtatcc cgcctgggga gtacgttcgc aagaatgaaa ctcaaaggaa ttgacggggg    3840
cccgcacaag cggtggagca tgtggtttaa ttcgatgcaa agcgaagaac cttaccaggg    3900
cttgacatgc cgcgaatcct cttgaaagag agggggtgcct tcgggaacgc ggacacaggt    3960
ggtgcatggc tgtcgtcagc tcgtgccgta aggtgttggg ttaagtcccg caacgagcgc    4020
aaccctcgtg tttagttgcc atcattgagt ttggaaccct gaacagactg ccggtgataa    4080
gccggaggaa ggtgaggatg acgtcaagtc atcatgcccc ttatgccctg ggcgacacac    4140
gtgctacaat ggccgggaca aagggtcgcg atcccgcgag ggtgagctaa ccccaaaaac    4200
ccgtcctcag ttcggattgc aggctgcaac tcgcctgcat gaagccggaa tcgctagtaa    4260
tcgccggtca gccatacggc ggtgaatccg ttcccgggcc ttgtacacac cgcccgtcac    4320
actatgggag ctggccatgc ccgaagtcgt taccttaacc gcaaggaggg ggatgccgaa    4380
ggcagggcta gtgactggag tgaagtcgta acaaggtagc cgtactggaa ggtgcggctg    4440
gatcacctcc ttttcaggga gagctaatgc ttgttgggta ttttggtttg acactgcttc    4500
acacccaaaa aagaagggag ctacgtctga gttaaacttg gagatggaag tcttcatttc    4560
gtttctcgac agtgaagtaa gaccaag                                        4587
```

<210> SEQ ID NO 3
<211> LENGTH: 4367
<212> TYPE: DNA
<213> ORGANISM: Nicotiana tabacum

<400> SEQUENCE: 3

```
gttcaagaat cagttttctt tttataaggg ctaaaatcac ttattttggc tttttacc       60 catattgtag ggtggatctc gaaagatatg aaagatctcc ctccaagccg tacatacgac    120
tttcatcgaa tacggctttc cgcagaattc tatatgtatc tatgagatcg agtatggaat    180
tctgtttact cactttaaat tgagtatccg tttccctccc tttcctgcta ggattggaaa    240
tcctgtattt tacatatcca tacgattgag tccttgggtt tccgaaatag tgtaaaaga    300 agtgcttcga atcattgcta tttgactcgg acctgttcta aaaaagtcga ggtatttcga    360
attgtttgtt gacacggaca aagtcaggga aaacctctga aattatttca atattgaacc    420
ttggacatat aagagttccg aatcgaatct ctttagaaag aagatctttt gtctcatggt    480
agcctgctcc agtcccctta cgaaactttc gttattgggt tagccataca cttcacatgt    540
ttctagcgat tcacatggca tcatcaaatg atacaagtct tggataagaa tctacaacgc    600
actagaacgc cctgttgac gatccttac tccgacagca tctagggttc ctcgaacaat     660
gtgatatctc acaccgggta aatccttaac ccttccccct cttactaaga ctacagaatg    720
```

```
ttcttgtaaa ttatggccaa taccgggtat ataagcagtg atttcaaatc cagaggttaa      780
tcgtactctg gcaactttac gtaaggcaga gtttggtttt tttggggtga tagtggaaaa      840
gttgacagat aagtcaccct tactgccact ctacagaacc gtacatgaga ttttcacctc      900
atacggctcc tcgttcaatt ctttcgaatt cattggatcc tttccgcgtt cgagaatccc      960
ccccttcttc cactccgccc cgaagagtaa ctaggaccaa tttagtcacg ttttcatgtt     1020
ccaattgaac actgtccatt tttgattatt ctcaaaggat aagattattc tctttaccaa     1080
acatatgcgg atccaatcac gatcttatat ataagaagaa caaaagatct ttcttgatca     1140 atcccttttgc ccctcattct tcaagaataa ggaagatcct tttcaagttt gaatttgttc    1200
atttggaatc tgggttcttc tacttcatat ttatttaata tgaatatttt ccctctcttt     1260 ttttatatc attccttaag tcccataggt ttgatcctgt agaatttgac ccattttctc      1320
attgaacgaa aggtacgaaa taaatcagat tgataaaagt accatgtgaa atcttcggtt     1380
tttccccttc ctcgatccct atcccatagg ttaggtacag tgtttgaatc aatagagaac     1440
cttttcttct gtatgaatcg atattattcc attccaaatc cttcccgata cctcccaagg     1500
aaaatctcga atttggatcc caaattgacg ggttagtgtg agcttatcca tgcggttatg     1560
cactctttga ataggaatcc gttttctgaa agatcctggc tttcgtactt tggtgggtct     1620
ccgagatcct ttcgatgacc tatgttgaag ggatatctat ctaatccgat cgattgcgta     1680
aagcccgcgg tagcaacgga accggggaaa gtatacagaa aagacagttc ttttctatta     1740
tattagtatt ttctattata ttagatatat tagactatta tattagatta gtattagtta     1800
gtgatcccga cttagtgagt ctgatgaatt gttggcacca gtcctacatt ttgtctctgt     1860
ggaccgagga gaaagggggc tcggcgggaa gaggagtgta ccatgagaga agcaaggagg     1920
tcaacctctt tcaaatatac aacatggatt ctggcaatgt agttggactc tcatgtcgat     1980
ccgaatgaat catcctttcc acggaggtaa atctttgcct gctaggcaag aggatagcaa     2040
gttccaaatt ctgtctcggt aggacatgta tttctattac tatgaaattc ataaatgaag     2100
tagttaatgg tagggttacc attatccttt ttgtagtgac gaatcttgta tgtgttccta     2160
agaaaaggaa tttgtccatt tttcggggtc tcaaaggggc gtggaaacgc ataagaactc     2220
ttgaatggaa aagagatgta actccagttc cttcggaatc ggtagtcaat cctatttccg     2280
ataggggcag ttgacaattg aatccgattt tgaccattat tttcatatcc gtaatagtgc     2340
gaaaagaagg cccggctcca agttgttcaa gaatagtggc gttgagtttc tcgacccttt     2400
gacttaggat tagtcagttc tatttctcga tggggcgggg aagggatata actcagcggt     2460
agagtgtcac cttgacgtgg tggaagtcat cagttcgagc ctgattatcc ctaagcccaa     2520
tgtgagtttt tctagttgga tttgctcccc cgccgtcgtt caatgagaat ggataagagg     2580
ctcgtgggat tgacgtgagg gggcagggat ggctatattt ctgggagcga actccgggcg     2640
aatatgaagc gcatggatac aagttatgcc ttggaatgaa agacaattcc gaatccgctt     2700
tgtctacgaa caaggaagct ataagtaatg caactatgaa tctcatggag agttcgatcc     2760
tggctcagga tgaacgctgg cggcatgctt aacacatgca agtcggacgg aagtggtgt      2820 ttccagtggc ggacgggtga gtaacgcgta agaacctgcc cttgggaggg gaacaacagc     2880
tggaaacggc tgctaatacc ccgtaggctg aggagcaaaa ggaggaatcc gcccgaggag     2940
gggctcgcgt ctgattagct agttggtgag gcaatagctt accaaggcga tgatcagtag     3000
ctggtccgag aggatgatca gccacactgg gactgagaca cggcccagac tcctacggga     3060
ggcagcagtg gggaattttc cgcaatgggc gaaagctgac ggagcaatgc cgcgtggagg     3120
```

```
tagaaggccc acgggtcgtg aacttctttt cccggagaag aagcaatgac ggtatctggg    3180
gaataagcat cggctaactc tgtgccagca gccgcggtaa tacagaggat gcaagcgtta    3240
tccggaatga ttgggcgtaa agcgtctgta ggtggctttt taagtccgcc gtcaaatccc    3300
agggctcaac cctggacagg cggtggaaac taccaagctg gagtacggta ggggcagagg    3360
gaatttccgg tggagcggtg aaatgcgtag agatcggaaa gaacaccaac ggcgaaagca    3420
ctctgctggg ccgacactga cactgagaga cgaaagctag gggagcgaat gggattagat    3480
accccagtag tcctagccgt aaacgatgga tactaggcgc tgtgcgtatc gacccgtgca    3540
gtgctgtagc taacgcgtta agtatcccgc ctggggagta cgttcgcaag aatgaaactc    3600
aaaggaattg acgggggccc gcacaagcgg tggagcatgt ggtttaattc gatgcaaagc    3660
gaagaacctt accagggctt gacatgccgc gaatcctctt gaaagagagg ggtgccttcg    3720
ggaacgcgga cacaggtggt gcatggctgt cgtcagctcg tgccgtaagg tgttgggtta    3780
agtcccgcaa cgagcgcaac cctcgtgttt agttgccatc gttgagtttg gaaccctgaa    3840
cagactgccg gtgataagcc ggaggaaggt gaggatgacg tcaagtcatc atgcccctta    3900
tgccctgggc gacacacgtg ctacaatggc cgggacaaag ggtcgcgatc ccgcgagggt    3960
gagctaaccc caaaaacccg tcctcagttc ggattgcagg ctgcaactcg cctgcatgaa    4020
gccggaatcg ctagtaatcg ccggtcagcc atacggcggt gaattcgttc ccgggccttg    4080
tacacaccgc ccgtcacact atgggagctg ccatgcccg aagtcgttac cttaaccgca    4140
aggaggggga tgccgaaggc agggctagtg actggagtga agtcgtaaca aggtagccgt    4200
actggaaggt gcggctggat cacctccttt tcagggagag ctaatgcttg ttgggtattt    4260
tggtttgaca ctgcttcaca cccccaaaaa aagaagggga gctacgtctg agttaaactt    4320
ggagatggaa gtcttctttc ctttctcgac ggtgaagtaa gaccaag          4367
```

<210> SEQ ID NO 4
<211> LENGTH: 131
<212> TYPE: PRT
<213> ORGANISM: Nicotiana tabacum

<400> SEQUENCE: 4

```
Met Lys Ile Met Val Lys Ile Gly Phe Asn Cys Gln Leu Pro Leu Ser
1               5                   10                  15

Glu Ile Gly Leu Thr Thr Asp Ser Glu Gly Thr Gly Val Thr Ser Leu
                20                  25                  30

Phe His Ser Arg Val Leu Met Arg Phe His Ala Pro Leu Arg Pro Arg
            35                  40                  45

Lys Met Asp Lys Phe Leu Phe Leu Gly Thr His Thr Arg Phe Val Thr
        50                  55                  60

Thr Lys Arg Ile Met Val Thr Leu Pro Leu Thr Thr Ser Phe Met Asn
65                  70                  75                  80

Phe Ile Val Ile Glu Ile His Val Leu Pro Arg Gln Asn Leu Glu Leu
                85                  90                  95

Ala Ile Leu Leu Pro Ser Arg Gln Arg Phe Thr Ser Val Glu Arg Met
            100                 105                 110

Ile His Ser Asp Arg His Glu Ser Pro Thr Thr Leu Pro Glu Ser Met
        115                 120                 125

Leu Tyr Ile
    130
```

<210> SEQ ID NO 5
<211> LENGTH: 70
<212> TYPE: PRT
<213> ORGANISM: Nicotiana tabacum

<400> SEQUENCE: 5

Met Lys Phe Ile Asn Glu Val Val Asn Gly Arg Val Thr Ile Ile Leu
1               5                   10                  15

Phe Val Val Thr Asn Leu Val Cys Val Pro Lys Lys Arg Asn Leu Ser
            20                  25                  30

Ile Phe Arg Gly Leu Lys Gly Ala Trp Lys Arg Ile Arg Thr Leu Glu
        35                  40                  45

Trp Lys Arg Asp Val Thr Pro Val Pro Ser Glu Ser Val Val Asn Pro
    50                  55                  60

Ile Ser Asp Arg Gly Ser
65                  70

<210> SEQ ID NO 6
<211> LENGTH: 28
<212> TYPE: DNA
<213> ORGANISM: Artificial
<220> FEATURE:
<223> OTHER INFORMATION: primer

<400> SEQUENCE: 6
atgagctcgt tcaagaatca gttttctt                                              28

<210> SEQ ID NO 7
<211> LENGTH: 43
<212> TYPE: DNA
<213> ORGANISM: Artificial
<220> FEATURE:
<223> OTHER INFORMATION: primer

<400> SEQUENCE: 7
ggcgcgcctt aattaatctt tttttcgca ctattacgga tat                              43

<210> SEQ ID NO 8
<211> LENGTH: 33
<212> TYPE: DNA
<213> ORGANISM: Artificial
<220> FEATURE:
<223> OTHER INFORMATION: primer

<400> SEQUENCE: 8
ttaattaagg cgcgccaggc ccggccccaa gtt                                        33

<210> SEQ ID NO 9
<211> LENGTH: 30
<212> TYPE: DNA
<213> ORGANISM: Artificial
<220> FEATURE:
<223> OTHER INFORMATION: primer

<400> SEQUENCE: 9
atggtaccct tggtcttact tcactgtcga                                            30

<210> SEQ ID NO 10
<211> LENGTH: 2252
<212> TYPE: DNA
<213> ORGANISM: Lactuca sativa

<400> SEQUENCE: 10
tcgacagtga agtaagacca agctcatgag cttattatct caggtcggaa caagttgata          60

-continued

```
ggatccccct ttttacgtcc ccatgccccc tgtgtggcga catggggggcg aaaaaaggaa      120 agagagagat ggggtttctc tcgcttttgg catagtgggc ccccagtggg gggctcgcac      180
gacgggctat tagctcagtg ggtagagcgc gcccctgata attgcgtcgt tgtgcctggg      240
ctgtgagggc tctcagccac atggatagtt caatgtgctc atcggcgcct gaccctgaga      300
tgtggatcat ccaaggcaca ttagcatggc gtactcctcc tgttcgaacc ggggtttgaa      360
accaaacttc tcctcaggag gatagatggg gcgattcagg tgagatccaa tgtagatcca      420
actttcgatt cactcgtggg atccggggcg tccgggggggg accaccatgg ctcctctctt      480
ctcgagaatc catacatccc ttatcagtgt atggacagct atctctcgag cacaggttta      540
ggttcggcct caatgggaaa ataaaatgga gcacctaaca acgcatcttc acagaccaag      600
aactacgaga tcaccccttt cattctgggg tgacggaggg atcataccat tcgagccttt      660
ttttttcatg cttttcccg aggtctggag aaagctgaaa tcataggat ttccctaatc      720 ctcccttacc gaaaggaaga gcgtgaaatt ctttttcctt tccgcaggga ccaggagatt      780
ggatctagcc gtaagaagaa tgcttggtat aaataactca cttcttggtc ttcgaccccc      840
gcagtcacta cgaacgcccc cgatcagtgc aatgggatgt gtctatttat ctatctcttg      900
actcgaaatg ggagcaggtt tgaaaaagga tcttagagtg tctagggttg gccaggagg      960 gtctcttaac gccttctttt ttcttctcat cggagttatt tcacaaagac ttgccatggt     1020
aaggaagaag gggggaacag gcacacttgg agagcgcagt acaacggaga gttgtatgct     1080
gcgttcggga aggatgaatc gctcccgaaa aggaatctat tgattctctc ccaattggtt     1140
ggaccgtagg tgcgatgatt tacttcacgg gcgaggtctc tggttcaagt ccaggatggc     1200
ccagctgcgc caggaaaaag aatagaagaa gcgtcagact attaattaag gcgcgcccat     1260
gcatgctcca cttggctcgg ggggatatag ctcagttggt agagctccgc tcttgcaatt     1320
gggtcgttgc gattacgggt tggatgtcta attgtccagg cggtaatgat agtatcttgt     1380
acctgaaccg gtggctcact ttttctaagt aatggggaag aggaccgaaa catgccactg     1440
aaagactcta ctgagacaaa gatgggctgt caagaacgtc aagaacgtag aggaggtagg     1500
atgggcagtt ggtcagatct agtatggatc gtacatggac ggtagttgga gtcggcggct     1560
ctcctagggt tcccttatcg gggatccctg gggaagagga tcaagttggc ccttgcgaac     1620
agcttgatgc actatctccc ttcaacccct tgagcgaaat gcggcaaaag gaaggaaaat     1680
ccatggaccg accccatcat ctccaccccg taggaactac gagattaccc caaggacgcc     1740
ttcggcatcc agggtcacg gaccgaccat agaaccctgt tcaataagtg gaacgcatta     1800
gctgtccgct ctcaggttgg gcagtaaggg tcggagaagg gcaatcactc attcttaaaa     1860
ccagcgttct taaggccaaa gagtcggcgg aaaaggggg aaagctctcc gttcctggtt     1920
tcctgtagct ggatcctccg gaaccacaag aatccttagt tagaatggga ttccaactca     1980
gcaccttttg agtgagattt tgagaagagt tgctctttgg agagcacagt acgatgaaag     2040
ttgtaagctg tgttcggggg ggagttattg tctatcgttg gcctctatgg tagaatcagt     2100
cgggggacct gagaggcggt ggtttacct gcggcggatg tcagcggttc gagtccgctt     2160
atctccaact cgtgaactta gccgatacaa agctatatga cagcacccaa ttttccgat      2220 ttggcggttc gatctatgat ttatcattca tg                                   2252
```

<210> SEQ ID NO 11
<211> LENGTH: 2253
<212> TYPE: DNA

<213> ORGANISM: Lactuca sativa

<400> SEQUENCE: 11

```
tcgacagtga agtaagacca agctcatgag cttattatct caggtcggaa caagttgata      60
ggatccccct ttttacgtcc ccatgccccc tgtgtggcga catggggcg aaaaaaggaa     120
agagagagat ggggtttctc tcgcttttgg catagtgggc ccccagtggg gggctcgcac    180
gacgggctat tagctcagtg ggtagagcgc gcccctgata attgcgtcgt tgtgcctggg    240
ctgtgagggc tctcagccac atggatagtt caatgtgctc atcggcgcct gaccctgaga    300
tgtggatcat ccaaggcaca ttagcatggc gtactcctcc tgttcgaacc ggggtttgaa    360
accaaacttc tcctcaggag gatagatggg gcgattcagg tgagatccaa tgtagatcca    420
actttcgatt cactcgtggg atccggcg tccgggggg accaccatgg ctcctctctt       480
ctcgagaatc catacatccc ttatcagtgt atggacagct atctctcgag cacaggttta    540
ggttcggcct caatgggaaa ataaaatgga gcacctaaca acgcatcttc acagaccaag    600
aactacgaga tcacccctt cattctgggg tgacggaggg atcataccat tcgagccttt     660
ttttttcatg ctttccccg aggtctggag aaagctgaaa tcaataggat ttccctaatc     720
ctcccttacc gaaaggaaga gcgtgaaatt cttttccctt tccgcaggga ccaggagatt    780
ggatctagcc gtaagaagaa tgcttggtat aaataactca cttcttggtc ttcgaccccc    840
gcagtcacta cgaacgcccc cgatcagtgc aatgggatgt gtctatttat ctatctcttg    900
actcgaaatg ggagcaggtt tgaaaaagga tcttagagtg tctagggttg gccaggagg     960
gtctcttaac gccttctttt ttcttctcat cggagttatt tcacaaagac ttgccatggt   1020
aaggaagaag gggggaacag gcacacttgg agagcgcagt acaacggaga gttgtatgct   1080
gcgttcggga aggatgaatc gctcccgaaa aggaatctat tgattctctc ccaattggtt   1140
ggaccgtagg tgcgatgatt tacttcacgg gcgaggtctc tggttcaagt ccaggatggc   1200
ccagctgcgc cagggaaaag aatagaagaa gcgtcagact ccttaattaa ggcgcgccca   1260
tgcatgctcc acttggctcg gggggatata gctcagttgg tagagctccg ctcttgcaat   1320
tgggtcgttg cgattacggg ttggatgtct aattgtccag gcggtaatga tagtatcttg   1380
tacctgaacc ggtggctcac ttttctaag taatggggaa gaggaccgaa acatgccact   1440
gaaagactct actgagacaa agatgggctg tcaagaacgt caagaacgta gaggaggtag   1500
gatgggcagt tggtcagatc tagtatggat cgtacatgga cggtagttgg agtcggcggc   1560
tctcctaggg ttcccttatc ggggatcct ggggaagagg atcaagttgg cccttgcgaa    1620
cagcttgatg cactatctcc cttcaaccct ttgagcgaaa tgcggcaaaa ggaaggaaaa   1680
tccatgacc gaccccatca tctccacccc gtaggaacta cgagattacc ccaaggacgc    1740
cttcggcatc caggggtcac ggaccgacca tagaaccctg ttcaataagt ggaacgcatt   1800
agctgtccgc tctcaggttg ggcagtaagg gtcgagaag gcaatcact cattcttaaa     1860
accagcgttc ttaaggccaa agagtcggcg gaaaaggggg gaaagctctc cgttcctggt   1920
ttcctgtagc tggatcctcc ggaaccacaa gaatccttag ttagaatggg attccaactc   1980
agcacctttt gagtgagatt ttgagaagag ttgctctttg gagagcacag tacgatgaaa   2040
gttgtaagct gtgttcgggg gggagttatt gtctatcgtt ggcctctatg gtagaatcag   2100
tcgggggacc tgagaggcgg tggtttaccc tgcggcggat gtcagcggtt cgagtccgct   2160
tatctccaac tcgtgaactt agccgataca aagctatatg acagcaccca attttttccga  2220
tttggcggtt cgatctatga tttatcattc atg                                 2253
```

<210> SEQ ID NO 12
<211> LENGTH: 1895
<212> TYPE: DNA
<213> ORGANISM: Nicotiana tabacum

<400> SEQUENCE: 12

| | | | | | |
|---|---|---|---|---|---|
| tcgacggtga | agtaagacca | agctcatgag | cttattatcc | taggtcggaa | caagttgata | 60 |
| ggaccccctt | ttttacgtcc | ccatgttccc | cccgtgtggc | gacatggggg | cgaaaaaagg | 120 |
| aaagagaggg | atggggtttc | tctcgctttt | ggcatagcgg | gcccccagtg | ggaggctcgc | 180 |
| acgacgggct | attagctcag | tggtagagcg | cgcccctgat | aattgcgtcg | ttgtgcctgg | 240 |
| gctgtgaggc | ctctcagcca | catggatagt | tcaatgtgct | catcggcgcc | tgaccctgag | 300 |
| atgtggatca | tccaaggcac | attagcatgg | cgtactcctc | ctgttcgaac | cggggtttga | 360 |
| aaccaaactc | ctcctcagga | ggatagatgg | ggcgattcgg | gtgagatcca | atgtagatcc | 420 |
| aactttcgat | tcactcgtgg | gatccgggcg | gtccgggggg | gaccaccacg | gctcctctct | 480 |
| tctcgagaat | ccatacatcc | cttatcagtg | tatggacagc | tatctctcga | gcacaggttt | 540 |
| agcaatggga | aaataaaatg | gagcacctaa | caacgcatct | tcacagacca | agaactacga | 600 |
| gatcgcccct | tcattctggg | ggtgacggag | ggatcgtacc | attcgagccg | ttttttttctt | 660 |
| gactcgaaat | gggagcaggt | ttgaaaaagg | atcttagagt | gtctagggtt | gggccaggag | 720 |
| ggtctcttaa | cgccttcttt | tttcttctca | tcggagttat | ttcacaaaga | cttgccaggg | 780 |
| taaggaagaa | gggggggaaca | agcacacttg | gagagcgcag | tacaacggag | agttgtatgc | 840 |
| tgcgttcggg | aaggatgaat | cgctcccgaa | aaggaatcta | ttgattctct | cccaattggt | 900 |
| tggaccgtag | gtgcgatgat | ttacttcacg | ggcgaggtct | ctggttcaag | tccaggatgg | 960 |
| cccagctgcg | ccagggaaaa | gaatagaaga | agcatctgac | tacttcatgc | atgctccact | 1020 |
| tggctcgggg | ggatatagct | cagttggtag | agctccgctc | ttgcaattgg | gtcgttgcga | 1080 |
| ttacggggttg | gatgtctaat | tgtccaggcg | gtaatgatag | tatcttgtac | ctgaaccggt | 1140 |
| ggctcacttt | ttctaagtaa | tggggaagag | gaccgaaacg | tgccactgaa | agactctact | 1200 |
| gagacaaaga | tgggctgtca | agaacgtaga | ggaggtagga | tgggcagttg | gtcagatcta | 1260 |
| gtatggatcg | tacatggacg | gtagttggag | tcggcggctc | tcccagggtt | ccctcatctg | 1320 |
| agatctctgg | ggaagaggat | caagttggcc | cttgcgaaca | gcttgatgca | ctatctccct | 1380 |
| tcaacccttt | gagcgaaatg | cggcaaaaga | aaaggaagga | aaatccatgg | accgaccccca | 1440 |
| tcatctccac | cccgtaggaa | ctacgagatc | accccaagga | cgccttcggc | atccaggggt | 1500 |
| cacggaccga | ccatagaacc | ctgttcaata | agtggaacgc | attagctgtc | cgctctcagg | 1560 |
| ttgggcagtc | agggtcggag | aagggcaatg | actcattctt | agttagaatg | ggattccaac | 1620 |
| tcagcaccctt | tgagtgaga | ttttgagaag | agttgctctt | tggagagcac | agtacgatga | 1680 |
| aagttgtaag | ctgtgttcgg | gggggagtta | ttgtctatcg | ttggcctcta | tggtagaatc | 1740 |
| agtcggggga | cctgagaggc | ggtggtttac | cctgcggcgg | atgtcagcgg | ttcgagtccg | 1800 |
| cttatctcca | actcgtgaac | ttagccgata | caaagcttta | tgatagcacc | caattttttcc | 1860 |
| gattcggcgg | ttcgatctat | gatttatcat | tcatg | | | 1895 |

<210> SEQ ID NO 13
<211> LENGTH: 22
<212> TYPE: DNA
<213> ORGANISM: Artificial
<220> FEATURE:

<223> OTHER INFORMATION: primer

<400> SEQUENCE: 13
tcgacagtga agtaagacca ag                                        22

<210> SEQ ID NO 14
<211> LENGTH: 39
<212> TYPE: DNA
<213> ORGANISM: Artificial
<220> FEATURE:
<223> OTHER INFORMATION: primer

<400> SEQUENCE: 14
ggcgcgcctt aattaaggag tcagacgctt cttctattc                      39

<210> SEQ ID NO 15
<211> LENGTH: 39
<212> TYPE: DNA
<213> ORGANISM: Artificial
<220> FEATURE:
<223> OTHER INFORMATION: primer

<400> SEQUENCE: 15
ttaattaagg cgcgcccatg catgctccac ttggctcgg                      39

<210> SEQ ID NO 16
<211> LENGTH: 26
<212> TYPE: DNA
<213> ORGANISM: Artificial
<220> FEATURE:
<223> OTHER INFORMATION: primer

<400> SEQUENCE: 16
catgaatgat aaatcataga tcgaac                                    26

<210> SEQ ID NO 17
<211> LENGTH: 20
<212> TYPE: DNA
<213> ORGANISM: Artificial
<220> FEATURE:
<223> OTHER INFORMATION: primer

<400> SEQUENCE: 17
actggaaggt gcggctggat                                           20

<210> SEQ ID NO 18
<211> LENGTH: 35
<212> TYPE: DNA
<213> ORGANISM: Artificial
<220> FEATURE:
<223> OTHER INFORMATION: primer

<400> SEQUENCE: 18
acgagccgga tgattaattg tcaattaatt aacta                          35

<210> SEQ ID NO 19
<211> LENGTH: 21
<212> TYPE: DNA
<213> ORGANISM: Artificial
<220> FEATURE:
<223> OTHER INFORMATION: primer

<400> SEQUENCE: 19
aagtcaccat tgttgtgcac g                                            21

<210> SEQ ID NO 20
<211> LENGTH: 20
<212> TYPE: DNA
<213> ORGANISM: Artificial
<220> FEATURE:
<223> OTHER INFORMATION: primer

<400> SEQUENCE: 20
ctcgccctta attttaaggc                                              20

<210> SEQ ID NO 21
<211> LENGTH: 1416
<212> TYPE: DNA
<213> ORGANISM: Lactuca sativa

<400> SEQUENCE: 21
actggaaggt gcggctggat cacctccttt tcagggagag ctaatgcttg ttgggtattt    60
tggtttgaca ctgcttcaca cccaaaaaag aagggagcta cgtctgagtt aaacttggag   120
atggaagtct tcatttcgtt tctcgacagt gaagtaagac caagctcatg agcttattat   180
ctcaggtcgg aacaagttga taggatcccc cttttttacgt ccccatgccc cctgtgtggc   240
gacatggggg cgaaaaaagg aaagagagag atggggtttc tctcgctttt ggcatagtgg   300
gcccccagtg gggggctcgc acgacgggct attagctcag tgggtagagc gcgcccctga   360
taattgcgtc gttgtgcctg gctgtgaggc gctctcagcc acatggatag ttcaatgtgc   420
tcatcggcgc ctgaccctga gatgtggatc atccaaggca cattagcatg cgtactcct    480 cctgttcgaa ccggggtttg aaaccaaact tctcctcagg aggatagatg gggcgattca   540
ggtgagatcc aatgtagatc caactttcga ttcactcgtg ggatccgggc ggtccggggg   600
ggaccaccat ggctcctctc ttctcgagaa tccatacatc ccttatcagt gtatggacag   660
ctatctctcg agcacaggtt taggttcggc ctcaatggga aaataaaatg gagcacctaa   720
caacgcatct tcacagacca agaactacga gatcacccct ttcattctgg ggtgacggag   780
ggatcatacc attcgagcct ttttttttca tgcttttccc cgaggtctgg agaaagctga   840
aatcaatagg atttccctaa tcctccctta ccgaaaggaa gagcgtgaaa ttcttttttcc   900 tttccgcagg gaccaggaga ttggatctag ccgtaagaag aatgcttggt ataaataact   960
cacttcttgg tcttcgaccc ccgcagtcac tacgaacgcc cccgatcagt gcaatgggat  1020
gtgtctattt atctatctct tgactcgaaa tgggagcagg tttgaaaaag gatcttagag  1080
tgtctagggt tgggccagga gggtctctta acgccttctt ttttcttctc atcggagtta  1140
tttcacaaag acttgccatg gtaaggaaga agggggggaac aggcacactt ggagagcgca  1200
gtacaacgga gagttgtatg ctgcgttcgg gaaggatgaa tcgctcccga aaaggaatct  1260
attgattctc tcccaattgg ttggaccgta ggtgcgatga tttacttcac gggcgaggtc  1320
tctggttcaa gtccaggatg gcccagctgc gccaggaaa agaatagaag aagcgtctga  1380
ctccttaatt aattgacaat taatcatccg gctcgt                            1416

<210> SEQ ID NO 22
<211> LENGTH: 2006
<212> TYPE: DNA

<213> ORGANISM: Lactuca sativa

<400> SEQUENCE: 22

```
aagtcaccat tgttgtgcac gacgacatca ttccgtggcg ttatccagct aagcgcgaac      60
tgcaatttgg agaatggcag cgcaatgaca ttcttgcagg tatcttcgag ccagccacga     120
tcgacattga tctggctatc ttgctgacaa aagcaagaga acatagcgtt gccttggtag     180
gtccagcggc ggaggaactc tttgatccgg ttcctgaaca ggatctattt gaggcgctaa     240
atgaaacctt aacgctatgg aactcgccgc ccgactgggc tggcgatgag cgaaatgtag     300
tgcttacgtt gtcccgcatt tggtacagcg cagtaaccgg caaaatcgcg ccgaaggatg     360
tcgctgccga ctgggcaatg agcgcctgc cggcccagta tcagcccgtc atacttgaag      420
ctagacaggc ttatcttgga caagaagaag atcgcttggc ctcgcgcgca gatcagttgg     480
aagaatttgt ccactacgtg aaaggcgaga tcaccaaggt agtcggcaaa taatgtctag     540
agcgatcctg gcctagtcta taggaggttt tgaaaagaaa ggagcagtaa tcattttctt     600
gttctatcaa gagggtgcta ttgctccttt cttttttctt tttatttat ttactagtat      660
tttacttaca tagactttt tgtttacatt atagaaaaag aaggagaggt tattttcttg      720
catttattca tgattgagta ttctattttg attttgtatt tgtttaaaat tgtagaaata     780
gaacttgttt ctcttcttgc taatgttact atatctttt gatttttttt tccaaaaaaa      840
aaatcaaatt ttgacttctt cttatctctt atctttgaat atctcttatc tttgaaataa     900
taatatcatt gaaataagaa agaagagcta tattcgaggc gcgcccatgc atgctccact     960
tggctcgggg ggatatagct cagttggtag agctccgctc ttgcaattgg gtcgttgcga    1020
ttacgggttg gatgtctaat tgtccaggcg gtaatgatag tatcttgtac ctgaaccggt    1080
ggctcacttt ttctaagtaa tggggaagag gaccgaaaca tgccactgaa agactctact    1140
gagacaaaga tgggctgtca agaacgtcaa gaacgtagag gaggtaggat gggcagttgg    1200
tcagatctag tatggatcgt acatggacgg tagttggagt cggcggctct cctagggttc    1260
ccttatcggg gatccctggg gaagaggatc aagttggccc ttgcgaacag cttgatgcac    1320
tatctcccct caacccttg agcgaaatgc ggcaaaagga aggaaaatcc atggaccgac    1380
cccatcatct ccaccccgta ggaactacga gattacccca aggacgcctt cggcatccag    1440
gggtcacgga ccgaccatag aaccctgttc aataagtgga acgcattagc tgtccgctct    1500
caggttgggc agtaagggtc ggagaagggc aatcactcat tcttaaaacc agcgttctta    1560
aggccaaaga gtcggcggaa aagggggaa agctctccgt tcctggtttc ctgtagctgg    1620
atcctccgga accacaagaa tccttagtta gaatgggatt ccaactcagc acctttgag    1680
tgagattttg agaagagttg ctctttggag agcacagtac gatgaaagtt gtaagctgtg    1740
ttcgggggg agttattgtc tatcgttggc ctctatggta gaatcagtcg ggggacctga    1800
gaggcggtgg tttaccctgc ggcggatgtc agcggttcga gtccgcttat ctccaactcg    1860
tgaacttagc cgatacaaag ctatatgaca gcacccaatt tttccgattt ggcggttcga    1920
tctatgattt atcattcatg gacgttgata agatccatcc atttagcagc accttaggat    1980
ggcatagcct taaaattaag ggcgag                                          2006
```

<210> SEQ ID NO 23
<211> LENGTH: 43
<212> TYPE: DNA
<213> ORGANISM: Artificial
<220> FEATURE:
<223> OTHER INFORMATION: primer

```
<400> SEQUENCE: 23
tcgagctctt aattaagcta ccccgccgtg attgaatgag aat                    43

<210> SEQ ID NO 24
<211> LENGTH: 41
<212> TYPE: DNA
<213> ORGANISM: Artificial
<220> FEATURE:
<223> OTHER INFORMATION: primer

<400> SEQUENCE: 24
aaatccctcc ctacaactgt atccaagcgc ttcgtattcg c                      41

<210> SEQ ID NO 25
<211> LENGTH: 41
<212> TYPE: DNA
<213> ORGANISM: Artificial
<220> FEATURE:
<223> OTHER INFORMATION: primer

<400> SEQUENCE: 25
gttgtaggga gggatttatg gcagaagcgg tgatcgccga a                      41

<210> SEQ ID NO 26
<211> LENGTH: 34
<212> TYPE: DNA
<213> ORGANISM: Artificial
<220> FEATURE:
<223> OTHER INFORMATION: primer

<400> SEQUENCE: 26
tcgcggccgc ttatttgccg actaccttgg tgat                              34

<210> SEQ ID NO 27
<211> LENGTH: 54
<212> TYPE: DNA
<213> ORGANISM: Artificial
<220> FEATURE:
<223> OTHER INFORMATION: primer

<400> SEQUENCE: 27
tcgcggccgc agttgtaggg agggatttat gcaaaaactt cccggaaatg acaa        54

<210> SEQ ID NO 28
<211> LENGTH: 30
<212> TYPE: DNA
<213> ORGANISM: Artificial
<220> FEATURE:
<223> OTHER INFORMATION: primer

<400> SEQUENCE: 28
ggatccttag tatcctgact tcagctcaac                                   30

<210> SEQ ID NO 29
<211> LENGTH: 42
<212> TYPE: DNA
<213> ORGANISM: Artificial
<220> FEATURE:
<223> OTHER INFORMATION: primer

<400> SEQUENCE: 29
aacatttaag gatccgactt tggtcttatt gtaattgtat ag                     42

<210> SEQ ID NO 30
```

```
<211> LENGTH: 36
<212> TYPE: DNA
<213> ORGANISM: Artificial
<220> FEATURE:
<223> OTHER INFORMATION: primer

<400> SEQUENCE: 30
atctgcaggg cggccatcca cttggctaca tccgcc                    36

<210> SEQ ID NO 31
<211> LENGTH: 35
<212> TYPE: DNA
<213> ORGANISM: Artificial
<220> FEATURE:
<223> OTHER INFORMATION: primer

<400> SEQUENCE: 31
tagttaatta attgacaatt aatcatccgg ctcgt                     35

<210> SEQ ID NO 32
<211> LENGTH: 34
<212> TYPE: DNA
<213> ORGANISM: Artificial
<220> FEATURE:
<223> OTHER INFORMATION: primer

<400> SEQUENCE: 32
tagggcgcgc ctcgaatata gctcttcttt ctta                      34

<210> SEQ ID NO 33
<211> LENGTH: 21
<212> TYPE: DNA
<213> ORGANISM: Artificial
<220> FEATURE:
<223> OTHER INFORMATION: primer

<400> SEQUENCE: 33
actaatagtg gacaaattgg c                                    21

<210> SEQ ID NO 34
<211> LENGTH: 21
<212> TYPE: DNA
<213> ORGANISM: Artificial
<220> FEATURE:
<223> OTHER INFORMATION: primer

<400> SEQUENCE: 34
ttgcttgatt gtatttactc g                                    21

<210> SEQ ID NO 35
<211> LENGTH: 21
<212> TYPE: DNA
<213> ORGANISM: Artificial
<220> FEATURE:
<223> OTHER INFORMATION: primer

<400> SEQUENCE: 35
aagtcaccat tgttgtgcac g                                    21

<210> SEQ ID NO 36
<211> LENGTH: 21
<212> TYPE: DNA
<213> ORGANISM: Artificial
<220> FEATURE:
<223> OTHER INFORMATION: primer

<400> SEQUENCE: 36
```

```
tatgacgggc tgatactggg c                                              21
```

<210> SEQ ID NO 37
<211> LENGTH: 20
<212> TYPE: DNA
<213> ORGANISM: Artificial
<220> FEATURE:
<223> OTHER INFORMATION: primer

<400> SEQUENCE: 37

```
actggaaggt gcggctggat                                                20
```

<210> SEQ ID NO 38
<211> LENGTH: 21
<212> TYPE: DNA
<213> ORGANISM: Artificial
<220> FEATURE:
<223> OTHER INFORMATION: primer

<400> SEQUENCE: 38

```
tatgacgggc tgatactggg c                                              21
```

<210> SEQ ID NO 39
<211> LENGTH: 21
<212> TYPE: DNA
<213> ORGANISM: Artificial
<220> FEATURE:
<223> OTHER INFORMATION: primer

<400> SEQUENCE: 39

```
atgcaaaaac ttcccggaaa t                                              21
```

<210> SEQ ID NO 40
<211> LENGTH: 20
<212> TYPE: DNA
<213> ORGANISM: Artificial
<220> FEATURE:
<223> OTHER INFORMATION: primer

<400> SEQUENCE: 40

```
ctcgccctta attttaaggc                                                20
```

<210> SEQ ID NO 41
<211> LENGTH: 85
<212> TYPE: PRT
<213> ORGANISM: Nicotiana tabacum

<400> SEQUENCE: 41

```
Thr Ile Thr Pro Lys Lys Pro Asn Ser Ala Leu Arg Lys Val Ala Arg
 1               5                  10                  15

Val Arg Leu Thr Ser Gly Phe Glu Ile Thr Ala Tyr Ile Pro Gly Ile
            20                  25                  30

Gly His Asn Leu Gln Glu His Ser Val Val Leu Val Arg Gly Gly Arg
        35                  40                  45

Val Lys Asp Leu Pro Gly Val Arg Tyr His Ile Val Arg Gly Thr Leu
    50                  55                  60

Asp Ala Val Gly Val Lys Asp Arg Gln Gln Gly Arg Ser Lys Tyr Gly
65                  70                  75                  80

Val Lys Lys Pro Lys
            85
```